United States Patent [19]
Kim

[11] Patent Number: 5,906,873
[45] Date of Patent: May 25, 1999

[54] PUNCTURE, PIERCE, AND CUT RESISTANT FABRIC

[75] Inventor: Young Hwa Kim, Woodbury, Minn.

[73] Assignee: Higher Dimension Medical, Inc., St. Paul, Minn.

[21] Appl. No.: 08/862,997

[22] Filed: May 27, 1997

Related U.S. Application Data

[63] Continuation-in-part of application No. 08/778,372, Jan. 2, 1997, Pat. No. 5,853,863, which is a continuation-in-part of application No. 08/675,146, Jul. 3, 1996.

[51] Int. Cl.⁶ ................................................. B32B 3/00
[52] U.S. Cl. .................................. 428/57; 2/2.5; 2/161.7; 2/167; 428/68; 428/131; 428/192; 428/223; 428/582; 428/911; 442/1
[58] Field of Search ........................... 428/223, 192, 428/44.52, 33, 57, 68, 131, 582, 911; 2/2.5, 161.7, 167; 442/1

[56] References Cited

U.S. PATENT DOCUMENTS

| | | | |
|---|---|---|---|
| 3,813,281 | 5/1974 | Burgess et al. | 161/159 |
| 4,442,150 | 4/1984 | Greiner et al. | 428/53 |
| 5,306,532 | 4/1994 | Tsien et al. | 428/33 |
| 5,601,895 | 2/1997 | Cunningham | 428/66.6 |

FOREIGN PATENT DOCUMENTS

| | | | |
|---|---|---|---|
| 0 657 110 A1 | 6/1995 | European Pat. Off. | F41D 13/10 |
| WO 95/07033 | 3/1995 | France . | |
| 2 287 639 | 9/1995 | United Kingdom | F41H 1/02 |
| 2 302 794 | 2/1997 | United Kingdom | F41H 1/02 |
| WO 92/08094 | 5/1992 | WIPO | F41H 1/02 |
| WO93/21492 | 10/1993 | WIPO | F41H 1/02 |

*Primary Examiner*—James J. Bell
*Attorney, Agent, or Firm*—Gray Plant Mooty Mooty & Bennett, P.A.; Malcolm D. Reid, Esq.

[57] ABSTRACT

A puncture, pierce, and cut resistant fabric comprised of a plurality of sheets of solid objects arranged in a repeating pattern. The solid objects are connected so that they are slideable relative to one another. Each sheet is in a stacked arrangement with the other sheets and are slideably interconnected to one another. Rivets are placed through apertures formed in or between the solid objects to hold the fabric together and to provide the slideable interconnection between the sheets. An interconnecting material interconnects the sheets of solid objects. An interconnecting material of elastomer returns the sheets from a stretched position to a compressed position. The fabric is formed with a means for limiting the movement of the solid objects relative to one another a predetermined amount, such as an elastomeric material inherently stretchable to a predetermined limit. The fabric is twistable, bendable, and stretchable. It is constructed of material that will withstand cutting, puncture, and piercing forces encountered in medical or other environments.

66 Claims, 53 Drawing Sheets

PUNCTURE, PIERCE, AND CUT RESISTANT FABRIC

This application is a continuation-in-part of application Ser. No. 778,372, filed Jan. 2, 1997 U.S. Pat. No. 5,853,863, entitled Puncture, Pierce, and Cut Resistant Fabric, which is a continuation-in-part of application Ser. No. 08/675,146, filed Jul. 3, 1996, entitled Puncture and Cut Resistant Fabric. Both of these preceding applications are incorporated herein by reference.

FIELD OF THE INVENTION

This invention relates generally to a puncture, pierce, and cut resistant fabric. More particularly, this invention relates to a fabric consisting of an array of loosely interconnected solid objects forming a flexible web suitable for use in garments, such as gloves and other garments worn in a medical, dental, or other environment where sharp instruments are prevalent and body armor garments worn to resist piercing by bullets and piercing and cutting by knives.

BACKGROUND OF THE INVENTION

With the prevalence of AIDS it has become increasingly clear that there is a strong need for materials that will resist puncture and cuts during medical and dental procedures, which generally expose personnel to sharp objects such as scalpels, needles for suturing and for injecting fluids, and drills for dental and orthopedic procedures. Although, AIDS has been the primary force behind the search for protection from blood borne infections, there is a host of such infections. Hepatitis and the Ebola infections are just two more examples of serious life threatening blood borne infections.

With rising numbers of gun shot and knife wounds, it has also become increasingly clear that there is a strong need for effective and user comfortable body armor to resist body piercing and/or cutting projectiles.

Surgical gloves are fabricated of an elastomeric polymeric material to act as a barrier to fluid flow and bacterial transmission between the patient and the care giver. They are most generally made from a thin layer of latex. Latex gloves allow the surgeon to retain a very high level of tactile sensitivity and ease of finger manipulation, but are easily cut by a scalpel or pierced or punctured by a needle.

Body armor is fabricated of non porous and, therefore, non breathing materials such as Kevlar or Spectra. These materials have proven effective at stopping body piercing projectiles, such as bullets, but ineffective at resisting knife wounds. Currently available body armor suffers from the additional drawback that it is often not worn due to the inability of such materials to allow perspiration to be evaporated from the wearer's skin.

There have been numerous attempts to fabricate garments such as surgical gloves that are cut, pierce, and puncture resistant and yet retain characteristics necessary to perform delicate surgical procedures. In particular, such a glove must allow the wearer to feel the surface on which he or she is working. In other words, it must preserve tactile sensitivity. The glove must also be stretchable, bendable, and twistable. It is useful that it also be elastic so that once stretched, bent, or twisted, the glove returns to its original configuration. The universally used latex glove has all of these properties, except the property of cut and puncture resistance.

Various approaches have been tried to provide the surgical glove with today's additional requirement of cut, pierce, and puncture resistance. For example, U.S. Pat. No. 4,742,578, to Seid, issued May 10, 1988 reinforces a surgical glove with an overlay of thin pliable material composed of a large number of tightly interlaced fibers or filaments of high strength. While this reportedly provides increased resistance to penetration, the margin of safety is far too low when faced with blood borne infections. U.S. Pat. No. 4,833,733, to Welch, issued May 30, 1989 incorporates a web of interwoven synthetic fibers such as nylon and aramid to provide some level of cut resistance, but due to the inherent porosity of the weave, it offers no puncture resistance. U.S. Pat. No. 4,864,661, to Gimbel, issued Sep. 12, 1989 purports to offer puncture resistance, but not cut resistance. Gimbel uses a woven fabric placed at high risk areas of the glove such as portions of the fingers. A woven fabric presents the possibility that a needle will be able to penetrate the fabric through the interstices formed by the intersecting fibers. U.S. Pat. No. 5,070,540, to Bettcher, issued Dec. 10, 1991 provides cut resistance using bundles of wire and fiber strands. The strands are situated throughout the entire glove. Bettcher does not purport to provide puncture resistance. The wire and fiber strands limit flexibility of the glove, a major requirement of a surgeon. U.S. Pat. No. 5,317,759, to Pierce, issued Jun. 7, 1994 is a glove with pillars extending perpendicular to the plane of the glove between outer and interior glove layers of a latex type material. The pillars reduce the chance of a suture needle piercing the glove, since, as the suture angles through the glove, it will most likely contact a pillar. This glove design suffers from the inability to stop a hypodermic needle piercing the glove at an angle close to perpendicular to the plane of the glove material. It also is not cut resistant and the rigid embedded pillars substantially reduce flexibility of the glove. U.S. Pat. No. 5,368,930, to Samples, issued Nov. 29, 1994 is an elastomeric sheet material with enhanced puncture resistance. Imbedded in the material are plate-like non-elastomeric particles. This material suffers from at least two deficiencies. It is not cut proof and the embedded plates make the material very stiff. U.S. Pat. No. 5,407,612, to Gould, issued Apr. 18, 1995 is similar to the Samples material. It has flat plates oriented parallel to the elastomeric glove material and embedded in the glove material. This has the unfortunate effect of acting like reinforcing rods in cement. The glove as a result becomes inflexible. While there have been other attempts to make a cut proof or a puncture proof surgical glove, they also fail to meet the unique combination of characteristics required by the surgical process.

As pointed out in this section by the review of certain patented gloves and glove material, there have been attempts to solve the major need of an effective and reliable barrier material to body fluid transmission between the health professional and the patient. Yet, this need must be met while maintaining the health professional's ability to carry on his or her task of surgery, drawing bodily fluids, or other such activity. Each of the currently available gloves or barrier material lacks one or more of the necessary properties for an effective surgical barrier. The properties include: (1) cut resistance, (2) puncture and pierce resistance, (3) flexibility, (4) bendability, (5) twistability, (6) elasticity, (7) stretchability, (8) ability to maintain the user's tactile sensitivity, and (9) an effective barrier to transmission of body fluids.

The object of this invention is to provide an effective cut, pierce, and puncture resistant barrier, for use in conjunction with conventional fluid barrier materials, that has all of the necessary properties for use in the medical, dental, and other fields where the transmission of body fluids between the care-giver and the patient must be eliminated.

It is a further object of this invention to provide an effective cut, pierce and puncture resistant barrier to body piercing projectiles, such as bullets and knives, combined with the ability of the barrier to allow the evaporation of the wearer's perspiration.

SUMMARY OF THE INVENTION

According to the present invention, the foregoing object and other objects and advantages are attained by provision of a fabric of a cut, pierce, and puncture resistant material. The fabric retains the necessary properties of flexibility, bendability, stretchability, twistability and elasticity by an array of loosely coupled solid objects held together to form a two dimensional sheet of fabric.

One form of solid object is a platelet as shown in FIGS. 2A through 2F. Other forms of solid objects are also efficacious for achieving the properties of the fabric and are described herein under the section entitled, "Detailed Description of the Preferred Embodiments".

The base of each platelet is a very thin wafer having a thickness much less than its outer dimensions. The platelets are constructed of a hard and strong material that is not brittle. The material type and its thickness will differ for body armor and other uses depending upon the level of force that must be resisted. In one embodiment of the invention, the width of the tab is less than the length of the edge of the base of the platelet.

Another aspect of the invention is a platelet with four equal sides, although other equal sided polygons will also result in a suitable fabric.

In a preferred embodiment tabs are an integral part of the platelet and are used to hook the platelets together The tabs extend from each of the platelet edges and tabs of adjacent platelets loosely interconnect. The tab extends from the edge of the base of the platelet in the same plane as the base of the platelet. At the end of the tab distal from the base of the platelet, the tab terminates in a hook extending away from the plane of the base of the platelet.

To provide a fabric suitable for economic manufacturability, all of the platelets are identical and they have integral tabs depending from each edge of the base of each platelet. However, the present invention can be practiced using a platelet having tabs that are separate from the base of the platelet. In such a case the tabs are interconnected to the edges of the base of the platelet by any suitable conventional means. The tabs may be connected to the edges of the base of the platelet in a flexible or a rigid manner, whichever best suits the application.

In accordance with another aspect of the invention, a plurality of rivets are inserted into an aperture, which is formed by the interconnected tabs of adjacent platelets. The rivets are inserted at a right angle to the plane of the fabric. In one embodiment the rivets completely cover the void surrounded by the interconnected tabs so that a virtually solid fabric is created, which blocks the path of a puncturing or piercing object such as a hypodermic needle, suture, or bullet.

In another embodiment, the platelets are held together with an elastomeric material bonded to the platelets or to rivets interposed through the plane of the fabric. In this embodiment, the hooks on the distal ends of the tabs may be eliminated depending upon the application.

In another embodiment, the fabric is assembled by connecting the hooks of the tabs of each platelet to the hooks of the tabs of adjacent platelets, which adjacent platelets have the plane of its base rotated 180 degrees about an axis parallel to and through the plane of the adjacent platelet. Thus every platelet in the array of platelets that make up the fabric has the hooks of its tabs reversed from those of its adjacent platelets. That is, the top of each adjacent platelet is flipped over so that the top is facing down instead of up. The fabric created is an array having platelets with tops up alternating with platelets with tops down in both rows and columns.

A fabric comprising platelets not having hooks referred to as planar platelets, is assembled in the same manner as set forth above, except the hooked connection between planar platelets is absent and reliance is placed upon elastomeric material affixed to the rivets or the planar platelets to hold the loosely interconnected platelets together. To avoid overstretching of the fabric where reliance is placed upon the elastomeric material to hold the fabric together rather than the hooks, a means for limiting the degree of stretch is employed. If the fabric overstretches, gaps may be opened between the planar platelets. Overstretching may also cause the rivets, if they are used, to be displaced out of position from their aperture. Several means for limiting stretch are available. A non-stretchable fiber may be affixed to the elastomeric fabric in such a way that in the fabric's unstretched state, the fiber has slack. As the fabric is stretched, the slack is taken up and at the end point where no more slack exists, further stretch is prevented.

Using the elastomeric material to allow stretchability in conjunction with a means for limiting the amount of stretch, allows for construction of a fabric using solid objects other than platelets with tabs. A layer of solid objects, referred to as plates, with elastomeric material and a means for limiting the amount of stretch affixed to the plates will provide a fabric that is suitable for resisting the piercing force of a bullet if the appropriate strength and size material is chosen for the plates. Using appropriate materials, this embodiment is also suitable for surgical gloves.

The fabric of the invention, comprising a two dimensional sheet of platelets having tabs on each edge of the base of the platelet for loose interconnection of the platelets, when combined between two elastomeric layers forms a cut and puncture resistant material suitable for fabrication of surgical or dental gloves and other wearing apparel for use in an operating room and for other purposes where a barrier to transmission of bodily fluids is required, and the risk of puncture or cuts is high.

The fabric of the invention, when manufactured of materials of suitable strength and size, and worn on the body forms a cut, puncture, and pierce resistant fabric suitable for resisting the force of certain ballistic projectiles and knives.

Still other objects and advantages of the present invention will become readily apparent to those skilled in this art from the following detailed description. To illustrate the invention, the Detailed Description of the Preferred Embodiments shows and describes only the preferred embodiments of the invention. However, as will be realized, the invention is capable of modification in various obvious respects, without departing from the invention. For example various permutations of the fabric may be constructed using solid objects in the form of platelets, planar platelets, or plates. The fabric may be constructed using rivets or without rivets. The tabs may be designed in various configurations to meet specific design needs. The fabric may be constructed using multiple layers of solid objects or a single layer. All the solid objects of the fabric may be identical or some may differ. For example, alternate layers of solid objects may have platelets with tabs that are inserted into slots on adjacent plates. Instead of inserting rivets at the corners of platelets, rivets may be inserted into apertures at the center of the base edges of plates. Accordingly, the drawings and detailed description are to be regarded as illustrative in nature, and not as restrictive.

DETAILED DESCRIPTION OF THE PREFERRED EMBODIMENTS

The following description of a cut, pierce, and puncture resistant fabric for apparel is provided to enable any person skilled in the art to make and use the invention and sets forth the best modes contemplated by the inventor for carrying out the invention. Various modifications, however, will remain readily apparent to those skilled in the art, since the generic principles of the present invention have been defined herein.

Figure 1A:
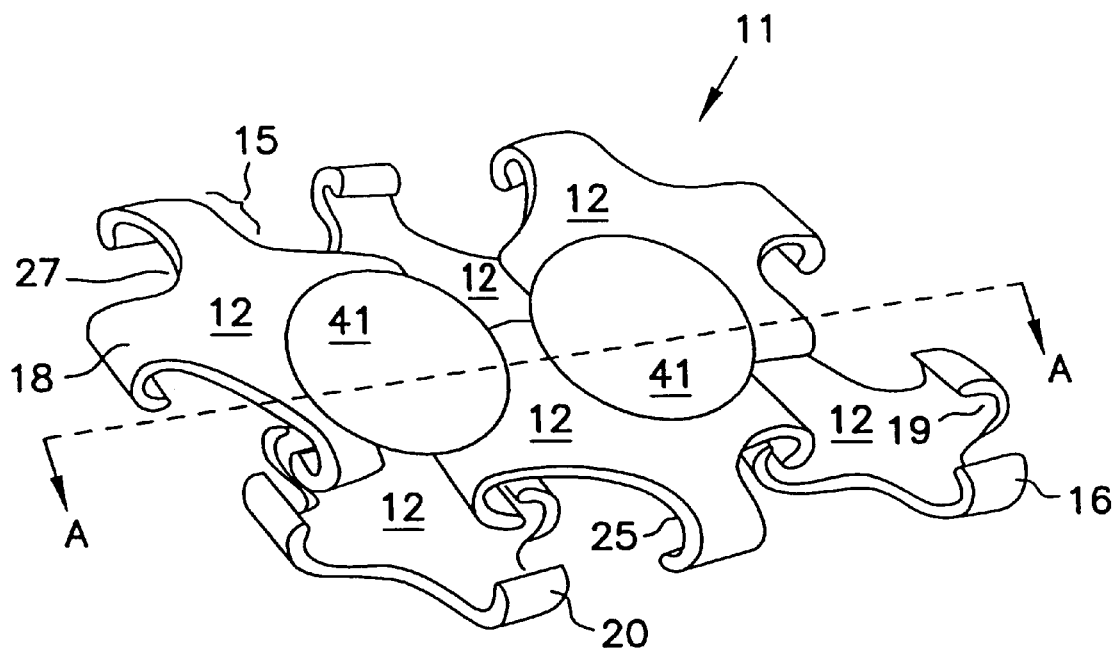
FIG. 1A is a perspective view of the fabric of the invention.
Figure 1B:
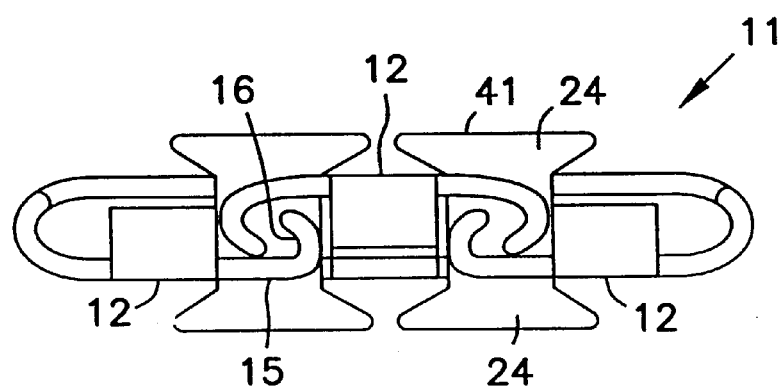
FIG. 1B is a cut-away side view along line A—A of FIG. 1A.
Figure 1C:
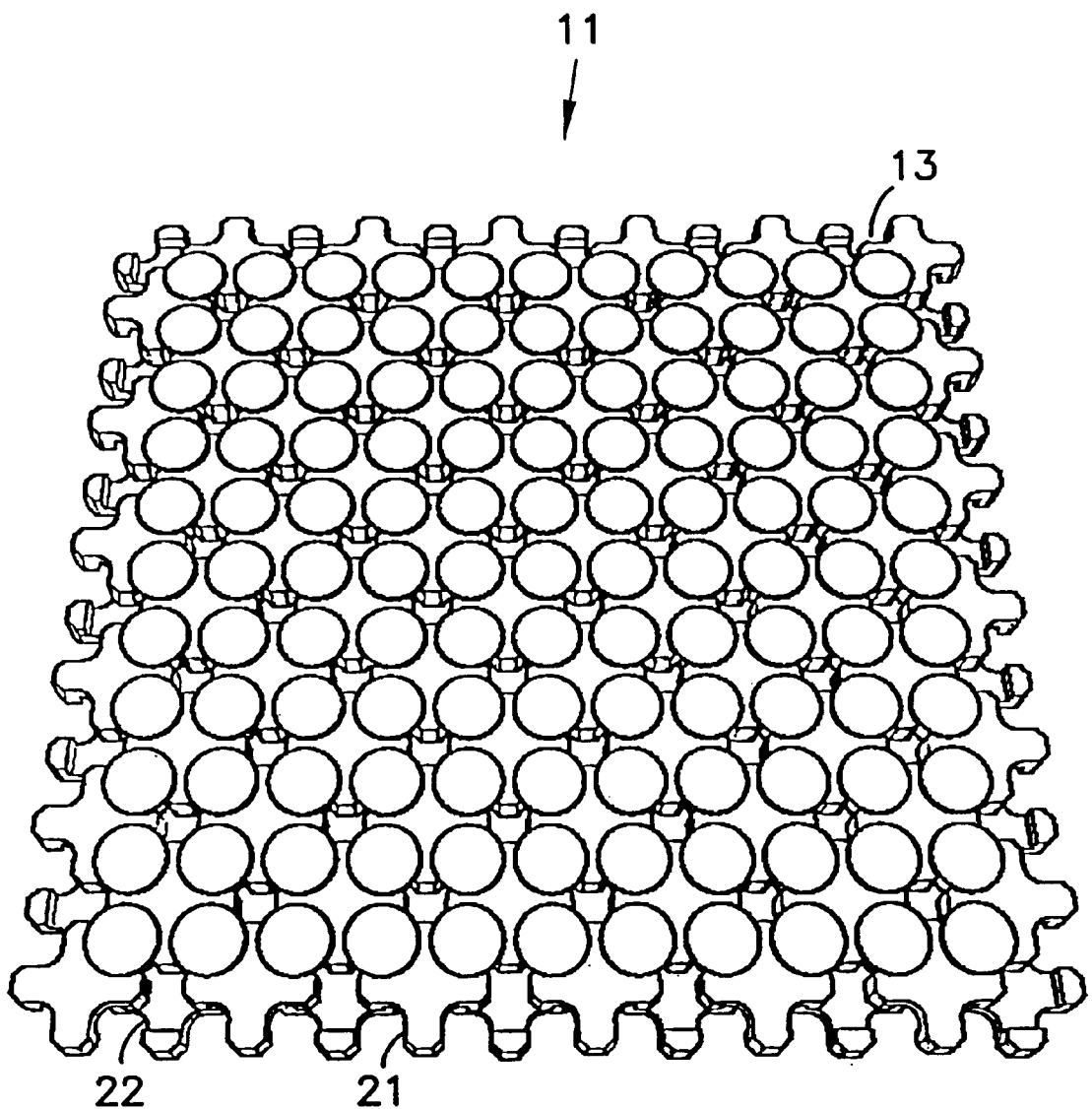
FIG. 1C depicts a large array of fabric.
Figure 8A:
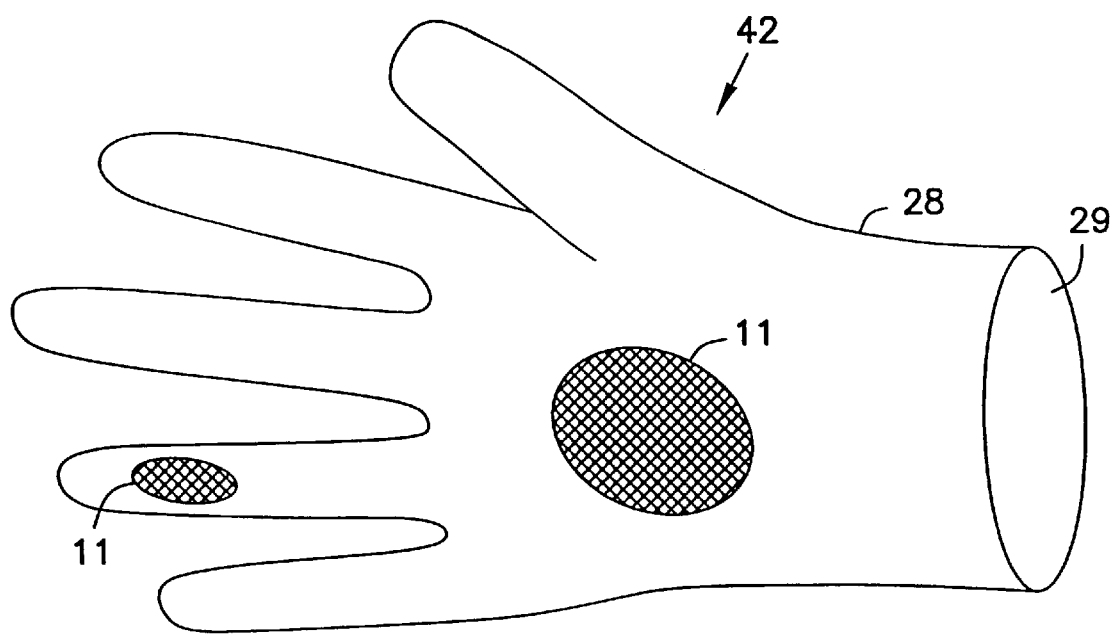
FIG. 8A is a perspective view of a surgical glove fabricated using the fabric with sections of the top layer of material cut-away to show the fabric.
Figure 8B:
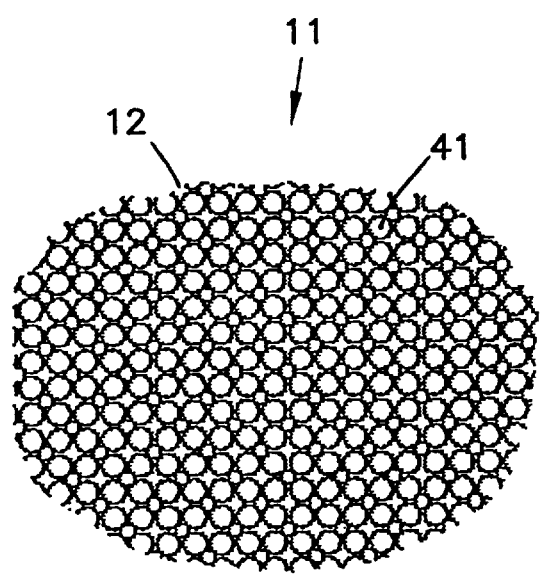
FIG. 8B is an enlargement of the detail shown in the cut-away of FIG. 8A.

FIG. 1A depicts a perspective view of an embodiment of the fabric 11 of the present invention. FIG. 1B is a cut-away side view along line A—A of FIG. 1A. FIG. 1C depicts a large array of the fabric 11 comprised of platelets 12, alternately with their bottoms 22 up and their tops 21 up, and rivets 13. The fabric 11 is constructed of very thin rigid platelets 12 and rivets 13, which are chosen to resist a puncture or piercing force equivalent to that exerted by a hypodermic needle in a medical environment or certain ballistic projectiles and knives. As can be seen from FIG. 1A, B, and C and the other figures illustrating this embodiment of the invention in this specification, there is no area of the fabric 11 that is not covered by either a rivet 13 or a platelet 12, thereby, foreclosing the penetration of a needle or other projectile striking the fabric 11. Specifying a material that will resist a needle puncture also results in a material that will resist cuts from instruments encountered in a medical setting, such as scalpels. For medical or dental applications, the fabric 11 of the invention is intended to be sandwiched between an upper and lower layer 28 and 29 of material that acts as a barrier to transmission of bodily fluids, as shown by the surgical glove in FIG. 8A. FIG. 8B shows an enlargement of the detail of FIG. 8A. An example of such a material is an elastomeric polymer such as latex. It is not necessary that the upper layer 28 be a fluid barrier, although it is preferable. Latex for gloves is approximately 0.1 millimeters or less thick, which is thick enough to cover the fabric 11 with an upper or lower layer 28 or 29. The fabric 11 is sandwiched between the upper and lower layers 28 and 29 with minimal or no attachments to those layers to allow the fabric free movement in all directions. To further promote free movement of the fabric 11 independent of the upper and lower layers 28 and 29, the surfaces of the fabric 11 and the sides of the upper and lower layers 28 and 29 in contact with the fabric 11 are lubricated with, for example, silicone. The silicone serves two functions. It assists the fabric 11 to freely bend, stretch, and twist and it decouples the fabric from the upper and lower layers 28 and 29 by imparting the fabric 11 with an anti-adhering property. While attachment of the fabric 11 to the upper and lower layers 28 and 29 must be kept at a minimum, attachment around the cuff, at the ends of the fingers, at one point on the back of the hand, and at one point on the palm prevents slippage of the fabric 11 relative to the upper and lower layers 28 and 29. The fabric is a useful component in other medical wearing apparel such as sleeves and aprons.

The fabric also has application for protective garments such as body armor or for individuals working in occupations such as a machinist or butcher. Garments for these other occupations as well as for applications in the medical and dental fields will require differing material type and thickness and dimensions of the platelets 12 and rivets 13, since the forces which come to bear upon the material will vary. The material type and dimensions for body armor will vary more drastically than for other applications, since the forces brought to bear on the fabric are several orders of magnitude greater than in other applications.

Even in the case of surgical gloves 42, the material sizes and type may vary since surgery and routine drawing of blood, for example, are performed under different conditions. And, it may not be necessary to fortify the entire glove 42 with the fabric 11. The fabric 11 may be placed strategically at only high risk zones. The size of a platelet 12 for a medical glove 42 application would be approximately one square millimeter. The diameter of the rivet 13 head 33 is approximately 0.7 millimeters.

The fabric of the present invention is not dependent upon a specific material type or dimensions. The fabric is scaleable to meet the widely varying uses to which it may be put. The choice of materials and dimensions are dependent upon the application and are determinable by routine engineering calculations The rigid material for manufacturing the platelets 12 and rivets 13 is currently available as off-the-shelf goods. The material can be metal (such as stainless steel or titanium), metal alloys, ceramic, plastic (such as Teflon, Kevlar, or Spectra), high strength composite materials (such as carbon fiber or glass composites), or any other material that resists the specified puncture, piercing, and cutting forces at the chosen thickness necessary to achieve the characteristics desired for the application. Any material should preferably not be brittle.

The process of assembling the rivets 13 and platelets 12 into the fabric 11 is performed by currently available production technology.

Figure 2A:
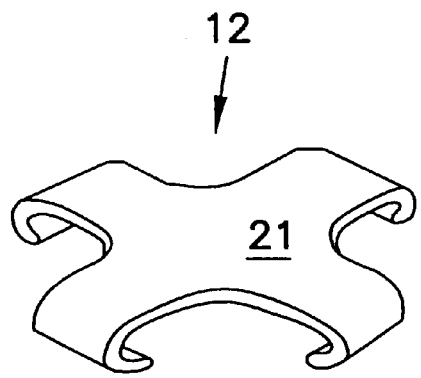
FIG. 2A is a perspective view of the top of the platelet.
Figure 2B:
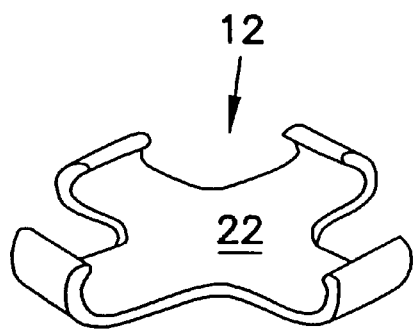
FIG. 2B is a perspective view of the bottom of the platelet.
Figure 2C:
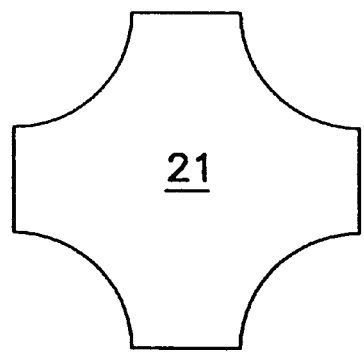
FIG. 2C is a plan view of the top of a platelet.
Figure 2D:
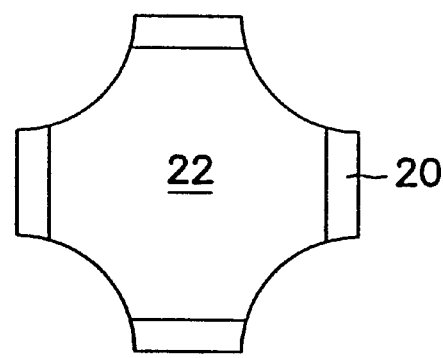
FIG. 2D is a plan view of the bottom of a platelet.
Figure 2E:
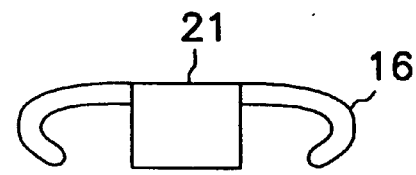
FIG. 2E is an elevation view of a platelet with the hooks down.
Figure 2F:
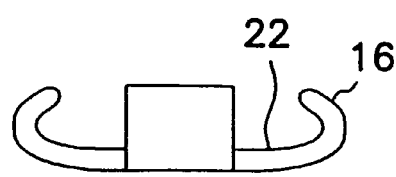
FIG. 2F is an elevation view of a platelet with the hooks up.

FIGS. 2A through 2F are various views and orientations of an embodiment of a platelet 12, the basic building block of the fabric 11. FIG. 2A is a top perspective view of the platelet 12. FIG. 2B is a bottom perspective view. FIG. 2C is a top plan view and FIG. 2D is a bottom plan view. FIG. 2E and 2F are side views of the platelet 12, respectively. FIGS. 2A through F depict the platelet as having an integral tab 15 (as more definitively shown in FIG. 4). However, other embodiments of the invention have tabs as a separate part of the platelet. Such tabs are connected to the base (as more definitively shown in FIG. 4) of the platelet by any suitable means.

Figure 3A:
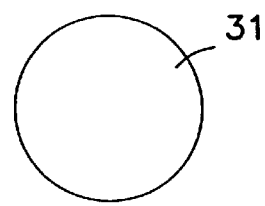
FIG. 3A is a plan view of one embodiment of a rivet.
Figure 3D:
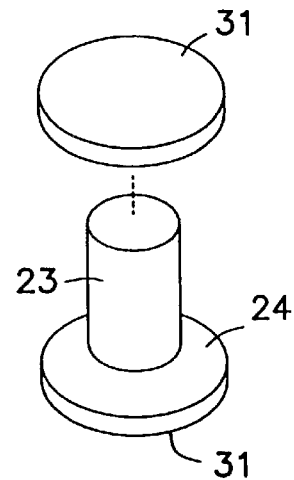
FIG. 3D is a perspective view of the rivet of FIG. 3A with one of the truncated cones separated.
Figure 3B:
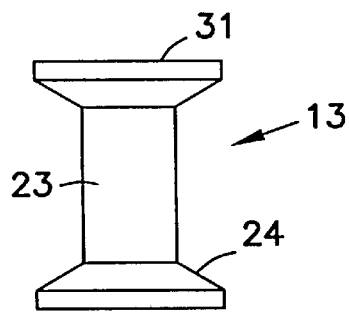
FIG. 3B is an elevation view of the rivet of FIG. 3A.
Figure 3E:
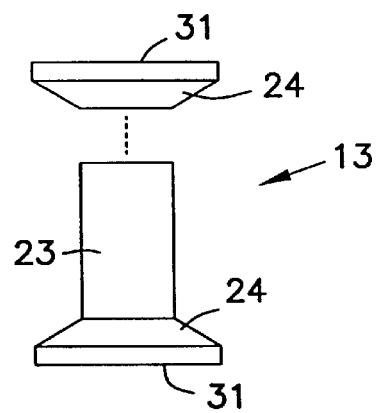
FIG. 3E is an elevational view of the rivet with one of the truncated cones separated.
Figure 3C:
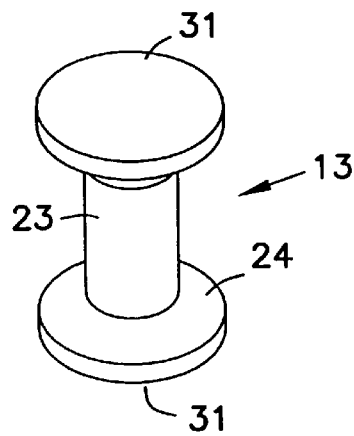
FIG. 3C is a perspective of the rivet of FIG. 3A.
Figure 3F:
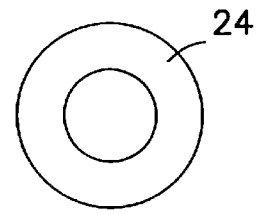
FIG. 3F is a plan view of the separated truncated cone shown in FIG. 3D from the truncated cone end.

FIG. 3A through 3D are views of an embodiment of a rivet 13, the only other building block of the fabric 11. FIG. 3A is a top view of the rivet 13, which consists of a pin 23 and two truncated cone heads 24 at each end of the pin 23. FIG. 3F shows where the top of the pin 23 of the rivet 13 is connected as a circle concentric with the top of the truncated cone head 24. One method of assembling fabric 11 employs a rivet 13 with one of the truncated cone heads 24 separated from the rivet 13, as shown in FIG. 3D. A pin 23 with one of the truncated cone heads 24 remaining attached is inserted through the aperture 26, shown in FIGS. 7A and 7B, until further movement is stopped by the attached truncated cone head 24 and the separated truncated cone head 24 is fused onto the other end of the pin 23 by welding or some other process.

Figures 4A, 4B:
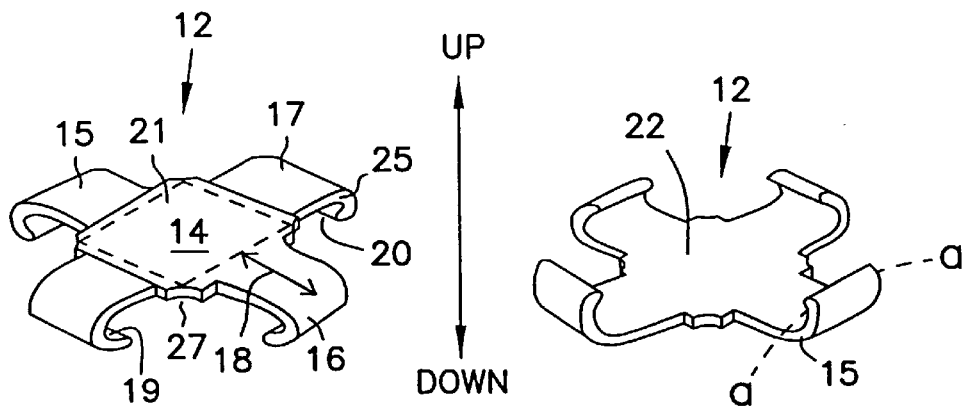
FIG. 4A is an enlarged perspective of the top of a platelet.
FIG. 4B is an enlarged perspective view of the bottom of a platelet.

FIGS. 4A and 4B, enlarged views of one embodiment of a platelet 12, illustrate the nomenclature used to identify the various portions of the platelet 12. The figures also arbitrarily establish the up and down direction for purposes of discussion in this specification. FIG. 4A is a view of the top 21 and FIG. 4B is a view of the bottom 22 of platelet 12. The area within the dotted lines is referred to as the base 14 of the platelet 12. The base 14 is a planar surface. The portions of the platelet 12 depending from a platelet base edge 17 is the tab 15. The tab 15 portion is more clearly indicated in FIG. 4B by the portion of FIG. 4B lying towards the right of line a—a. In the embodiment shown in FIGS. 4A and B, the tab terminates at the end distal to the base 17 in arc 19, which extends away from, and perpendicular to, the plane of the base 14 of the platelet 12. The arc 19 of the tab 15 is aligned with the arm 18 portion of the tab 15 as shown in FIG. 2A through 2F. The hook 16 of the platelet 12 is formed by the arc 19 and reverse tab portion 20. The reverse tab portion 20 is the portion of the hook 16 that reverses back towards the base edge 17 of the platelet 12. The arm 18 of the tab 15 is a planar surface and is in the same plane as the base 14 of the platelet 12. The width of the tab 15 is less than the length of the base edge 17 of the platelet 12. As previously noted, the tab 15 may be separate from the base 14 of the platelet 12 rather than an integral part of the platelet 12 as shown in FIG. 4 and the other figures of the specification. A separate tab 15 may be connected to the base 14 by either a rigid or a flexible connection depending on the needs of the application. In the preferred embodiment, the base 14 of the platelet 12 is a polygon having four equal sides. Other figures in this specification illustrate alternative embodiments of the platelet 12, one with a different hook 16 configuration and another with no hooks 16. The no hook 16 embodiment platelet 12 is referred to as a planar platelet 46. Fabric assembled with planar platelets 46 is loosely interconnected using an elastomeric material in place of the interconnected hooks 16. An elastomeric material may also be used in combination with a fabric 11 constructed with platelets 12. Such a combination adds, among other attributes, elasticity. Elasticity will aid the fabric 11 to return to its compressed state upon removal of a stretching force. Also illustrated in this specification is a fabric 11 assembled with a square shaped solid object instead of a solid object configured as a platelet 12 or a planar platelet 46. The square shaped solid object is referred to as a plate 65.

Figure 5:
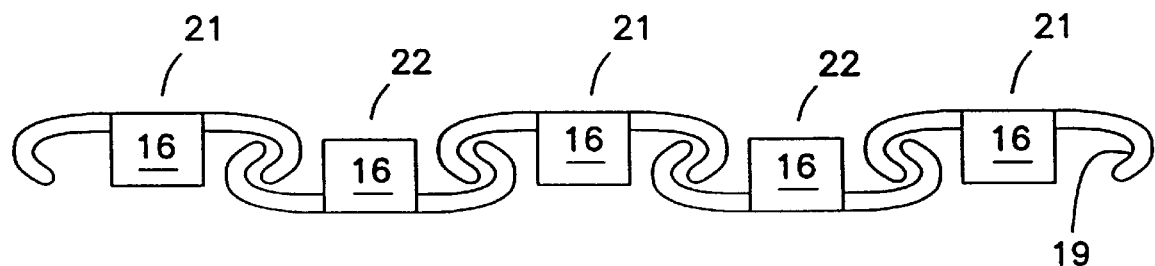
FIG. 5 is a cut-away view of a one dimensional chain of loosely interconnected platelets.

A continuous two dimensional sheet of fabric 11 of any length or width is assembled by interconnecting multiple platelets 12 and rivets 13 in an array as shown in FIGS. 1A and 1B and 6A through 6C. Each of the platelets 12 and rivets 13 that make up the fabric are identical. The orientation of adjacent platelets 12 are reversed so that the hooks 16 of each platelet 12 are interconnected as shown in FIG. 5. FIG. 5 shows a one dimensional string of platelets 12 viewed in cut-away from the side. In the actual fabric 11 as shown in FIGS. 1A, 1B, and 6A through 6C, the tabs 15 of each adjacent platelet 12 are interconnected on four sides by mating the opposing hooks 16 of the adjacent platelets 12 having their bottoms 22 up with those of the platelets 12 having their tops 21 up. The orientation of the adjacent platelets 12 differs only in that adjacent platelet 12 is rotated so that the bottom 22 of the adjacent platelet 12 faces upward as illustrated in FIGS. 1, 5, and 6.

Figure 6A:
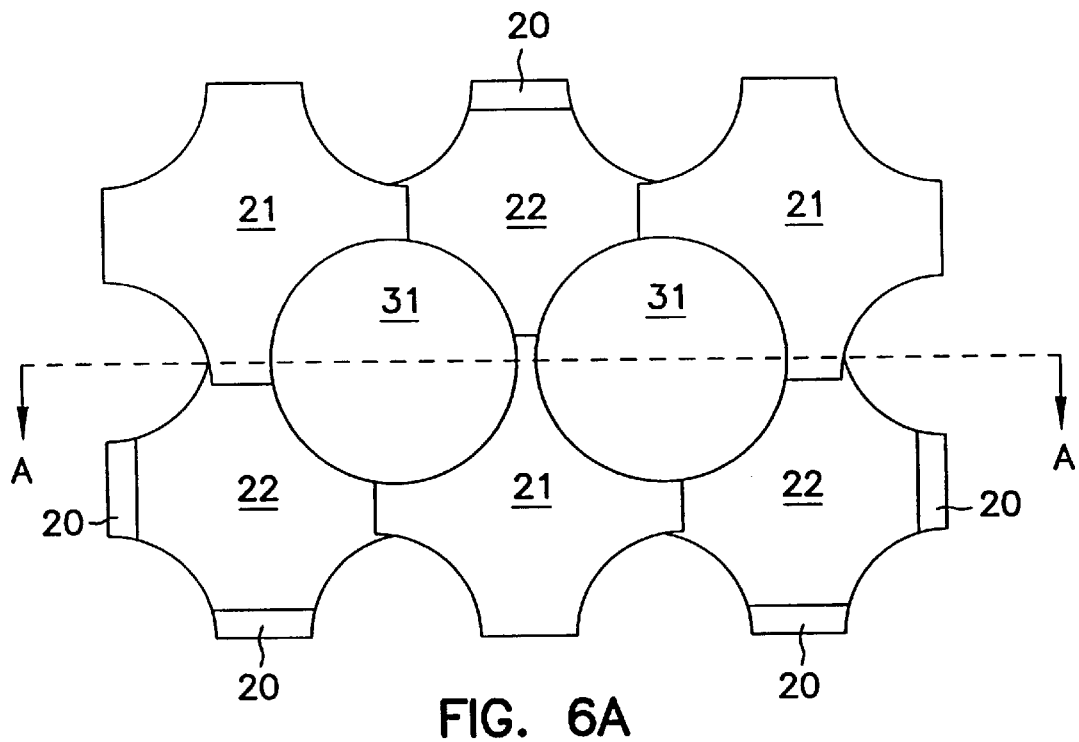
FIG. 6A is a plan view of the fabric, wherein dotted line A—A represents an imaginary plane that cuts the fabric into two pieces.
Figure 6B:
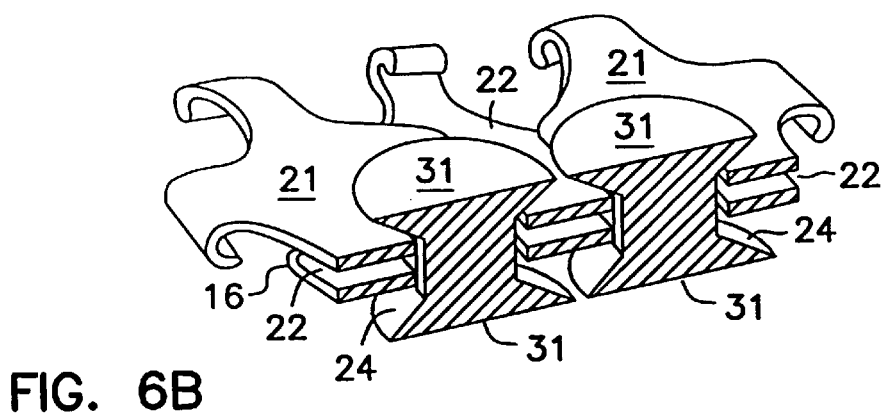
FIG. 6B is a perspective view of a segment of the fabric of the invention cut through the fabric by a plane normal to the fabric along line A—A of FIG. 6A.
Figure 6C:
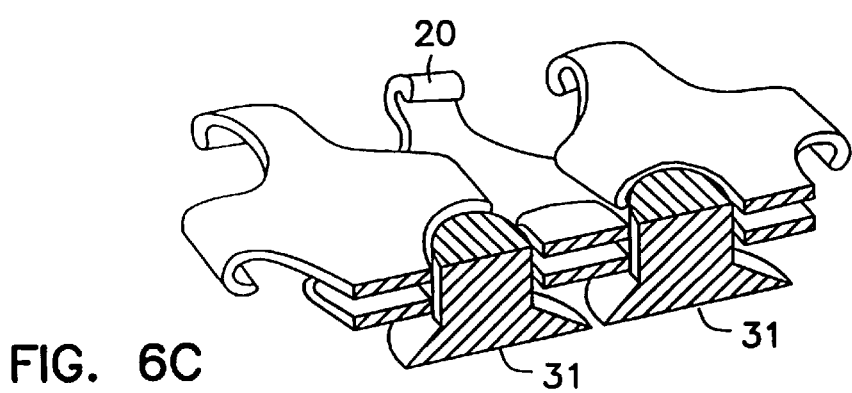
FIG. 6C is another perspective view of a segment of the fabric cut through the fabric by a plane normal to the fabric along a line A—A of FIG. 6A with the truncated cone of one side of the rivets cut off.
Figure 7A:
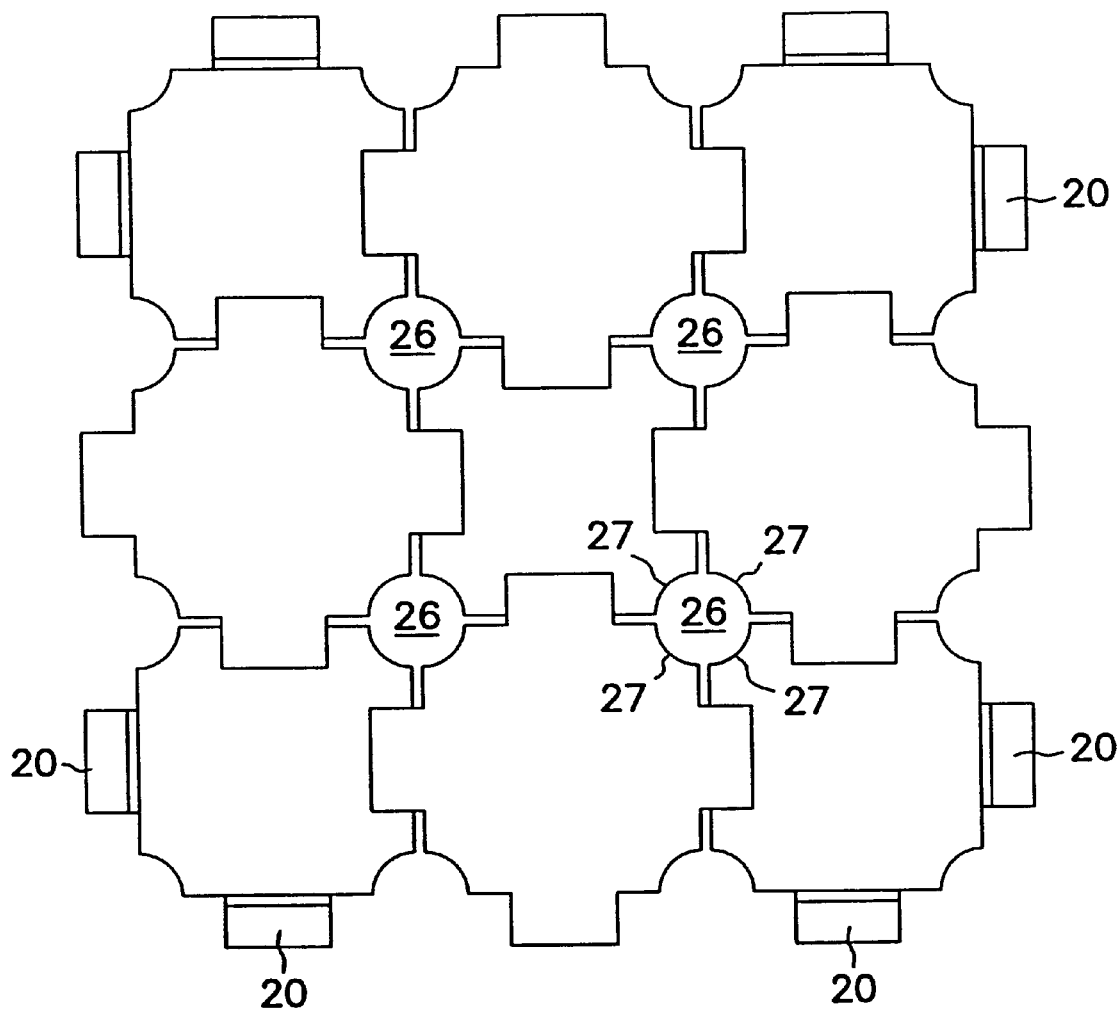
FIG. 7A is a plan view of the fabric, without rivets, with the platelets in a fully compressed configuration with minimum surface area.
Figure 7B:
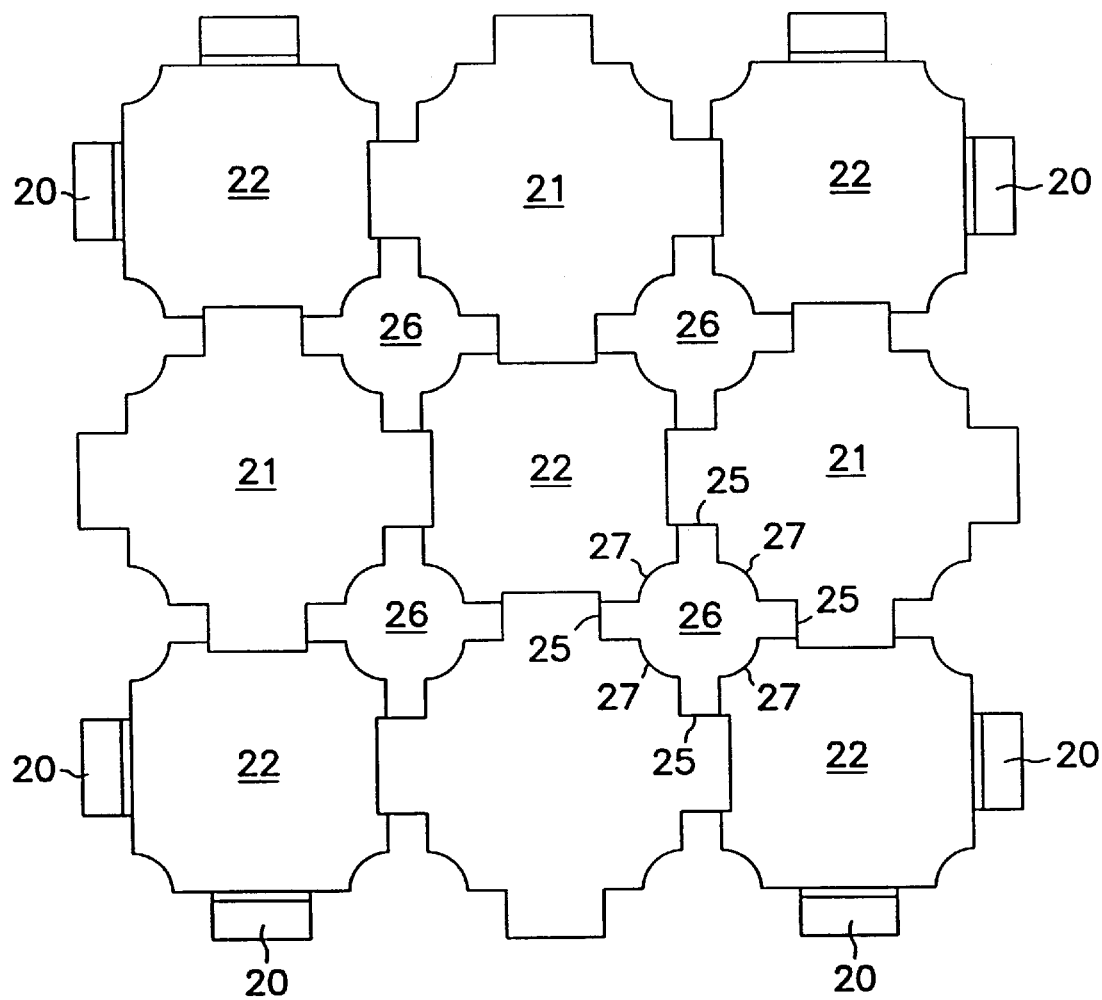
FIG. 7B is a plan view of the fabric, without rivets, with the platelets in a fully stretched configuration with the maximum surface area.

The pins 23 of rivets 13 are inserted perpendicular to the plane of the fabric 11 through the apertures 26, shown in FIGS. 7A and 7B, formed by the tab edges 25 and the concave arc 27 that forms the intersection of adjacent base edges 17 of the platelet 12 and the tab edges 25 and the concave arc 27 of adjacent interconnected platelets 12. The rivets 13 are locked into the fabric 11 perpendicular to its plane by the truncated cone 24 ends as shown in FIGS. 6A, 6B, and 6C. The pin 23 is of a length that allows a slight movement of the rivet perpendicular to the fabric. The pin 23 length is also chosen to allow movement of the tabs 15 upwardly and downwardly relative to the plane of the fabric 11. The diameter of the pin 23 is almost the same as the diameter of the aperture 26 when the fabric 11 is fully compressed as shown in FIG. 7A to form what is commonly referred to as a push fit between the pin 23 and the aperture 26. The push fit of the rivet 13, even when the fabric 11 is in its fully compressed state, allows for flexibility of the fabric 11 as well as transmission of tactile forces through the fabric 11 so that the wearer retains an ability to feel or sense surgical procedures.

To allow for flexibility, which includes the properties of stretchability, bendability, and twistability, the hooks 16 must be dimensioned appropriately relative to adjacent hooks 16. The rivets 13 must also be dimensioned appropriately relative to the aperture 26 in which it is inserted. Although, the meaning of the terms stretchability, bendability, and twistability is generally appreciated, reference to FIGS. 9, 10, 11, and 12 are helpful to understand the unique means by which this fabric 11 is able to achieve these requirements and the importance of the dimensions of the hooks and the rivets in relation to the aperture.

Figure 9A:
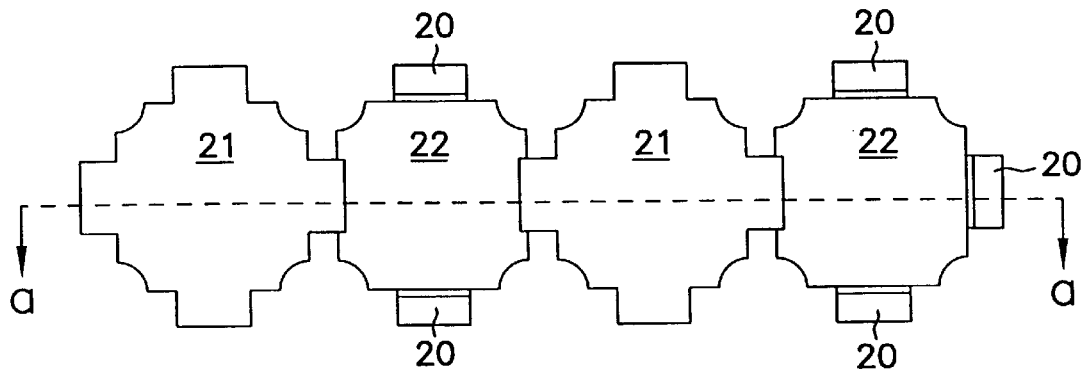
FIG. 9A is a plan view of a line of platelets fully stretched.
Figure 9B:
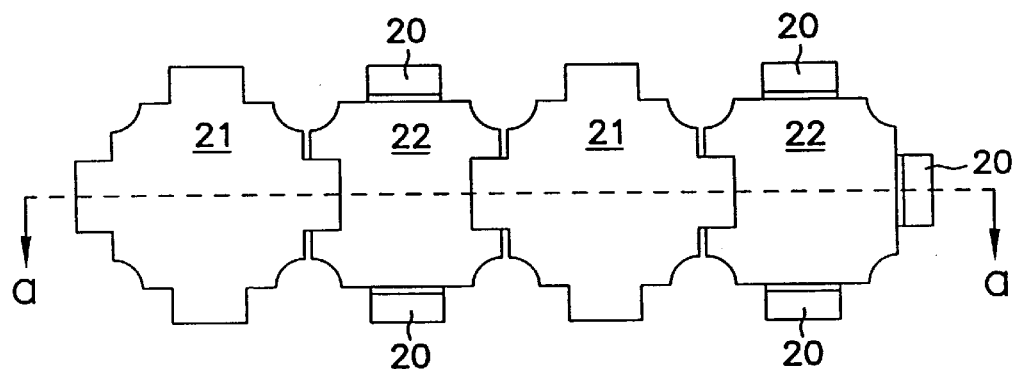
FIG. 9B is a plan view of a line of platelets fully compressed.
Figure 9C:
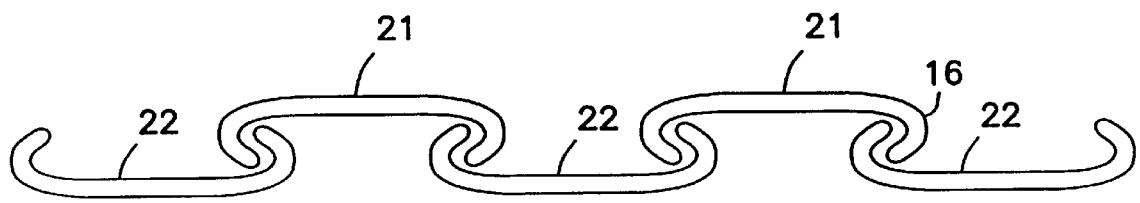
FIG. 9C is a cross section of the line of platelets of FIG. 9A.
Figure 9D:
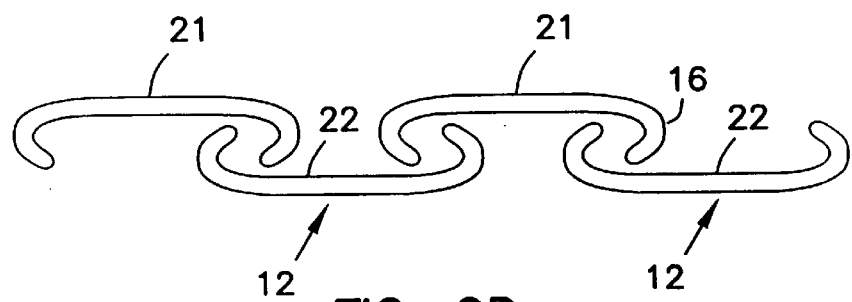
FIG. 9D is a cross section of the line of platelets of FIG. 9B.

FIG. 9A illustrates a line of platelets 12 connected in accordance with the invention. FIG. 9A shows the platelets 12 in a configuration of maximum separation. FIG. 9B illustrates the platelets in a configuration of minimum separation. FIG. 9C is a cross-section taken along line a—a of FIG. 9A. FIG. 9C illustrates how the hooks 16 can be pulled to their outer extremities and yet not separate due to the positive engagement of the hooks 16. The hook 16 of each platelet 12 slides along the bottom of its matingly engaged platelet 12 until the maximum stretch, or length, of the string of platelets 12 is achieved. FIG. 9D is a cross-section taken along line a—a of FIG. 9B. FIG. 9D illustrates how the hooks 16 can slide towards the center of each platelet 12 to arrive at the point of least stretch, or length. The ability of the hooks 16 to slide towards the center of each platelet 12 results in a slideable interconnection of the platelets 12.

Figure 10A:
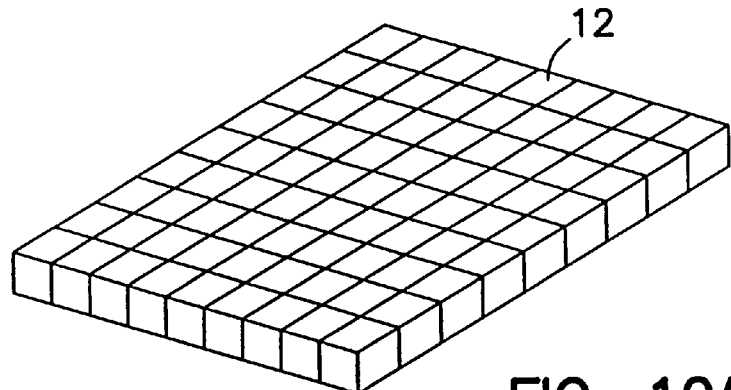
FIG. 10A and B illustrate bendability of the fabric of the invention.
Figure 10B:
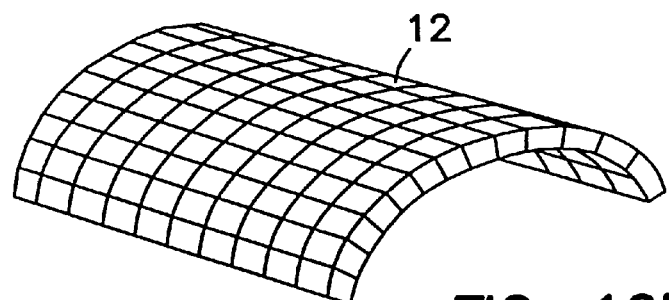

Bendability of the fabric 11 is illustrated in FIGS. 10A and B where each block denotes one platelet 12. FIG. 10A shows the fabric 11 as a flat array of platelets. FIG. 10B shows the fabric 11 bent in a curve. The property of bendability is the result of the hooks 16 allowing for arcuate movement of one platelet 12 relative to another. The arc 19 of the hook 16 facilitates this radial movement, but a planar hook 38 with a finger 30, as shown in FIG. 24 projecting downward from the distal end of the arm 18 of the tab 15 also allows adequate arcuate movement.

Figure 11:
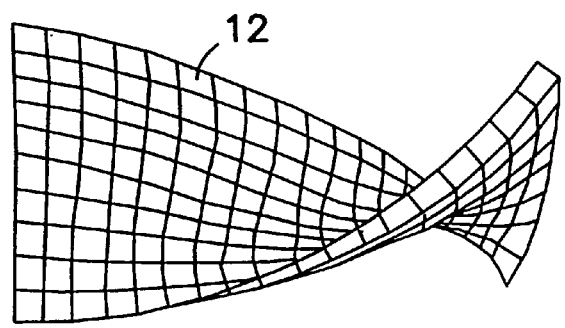
FIG. 11 shows the property of twistability of the fabric of the invention.
Figure 12A:
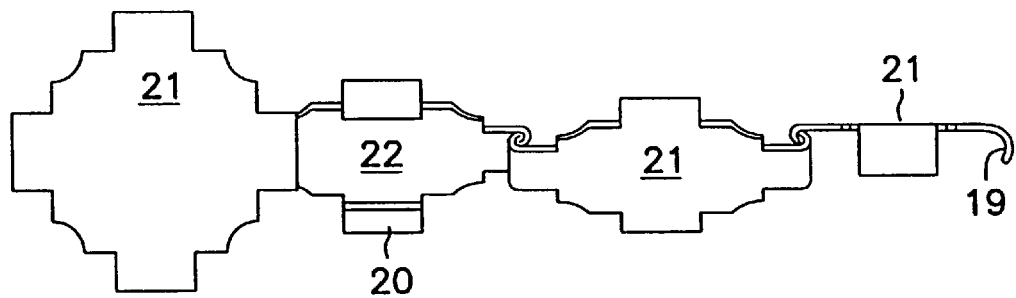
FIGS. 12A and B depict twistability of the invention showing actual platelets in a twisted condition.
Figure 12B:
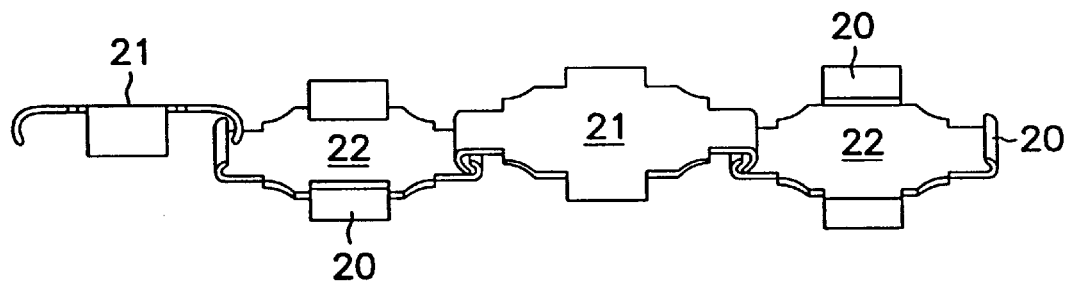

FIG. 11 shows a twisted fabric 11, where each block also represents a platelet 12. FIGS. 12A and B illustrate twisting of the fabric 11 as shown by actual depictions of the platelets 12.

Figure 25:
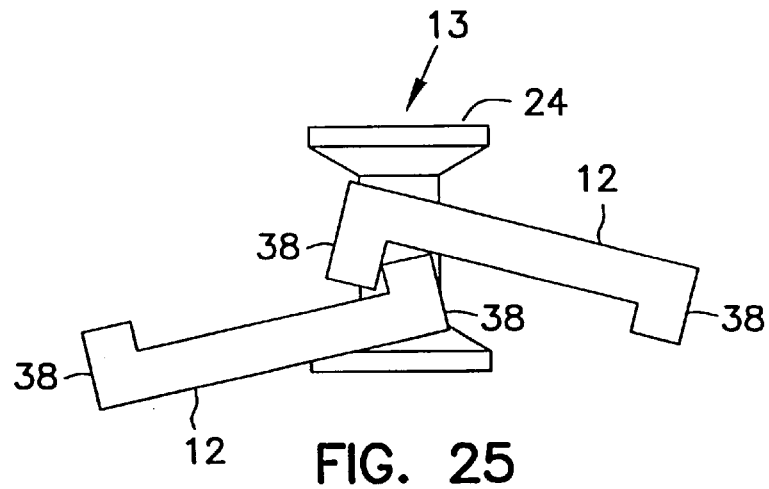
FIG. 25 shows the bending action facilitated by the truncated cone.

The hooks 16 by the nature of their construction and the mating engagement allow for movement of one platelet 12 with its top 21 up relative to each adjacent platelet 12 with its bottom 22 up. The mating engagement results in a loose coupling or slideable interconnection of the platelets 12. It is the slideable interconnection that allows the fabric 11 to approximate the flexibility characteristic of an elastomeric material. The hooks 16 allow for sliding movement of the platelets 12 relative to one another in a direction along a line in the plane of the platelet 12 and substantially parallel to the tabs 15. To allow the platelets 12 to slideably move relative to one another in a direction away from each other, the reverse tab portion 20 is of a length that is less than the length of the arm 18 of the tab 15. The hooks 16 also allow movement in a downward and upward direction relative to the plane of the platelet 12, as shown in FIG. 25, which is a cross-section of a platelet 12 restrained by a rivet 13 as in the fabric of the present invention. FIG. 25 illustrates a platelet 12 with a planar hook 38, an alternative embodiment platelet 12. Movement in this direction is a function of the length of the rivet 13. The hook 16 also allows movement transverse to the tab 15. However, movement in the transverse direction is checked by the tab edge 25 contacting the rivet 13. The rivet 13 pin 23 in the compressed state of the fabric all but fills the aperture, thereby allowing virtually no transverse movement. Were it not for contact with the rivet 13 in both the compressed and the stretched configuration of the fabric 11, the mating hooks 16 would disengage and the fabric 11 would have the equivalent of a tear or a hole. However, there is a greater range of transverse movement of the platelets 12 relative to one another when the fabric 11 is stretched, because the area of the aperture 26 is greater in the stretched configuration then when compressed. This is illustrated by a comparison of FIGS. 7A, the compressed state, to 7B, the stretched state. And since the diameter of the pin 23 of the rivet 13 is a constant, the platelet 12 hooks 16 are allowed to move to fill the additional space in the aperture 26.

Figure 13A:
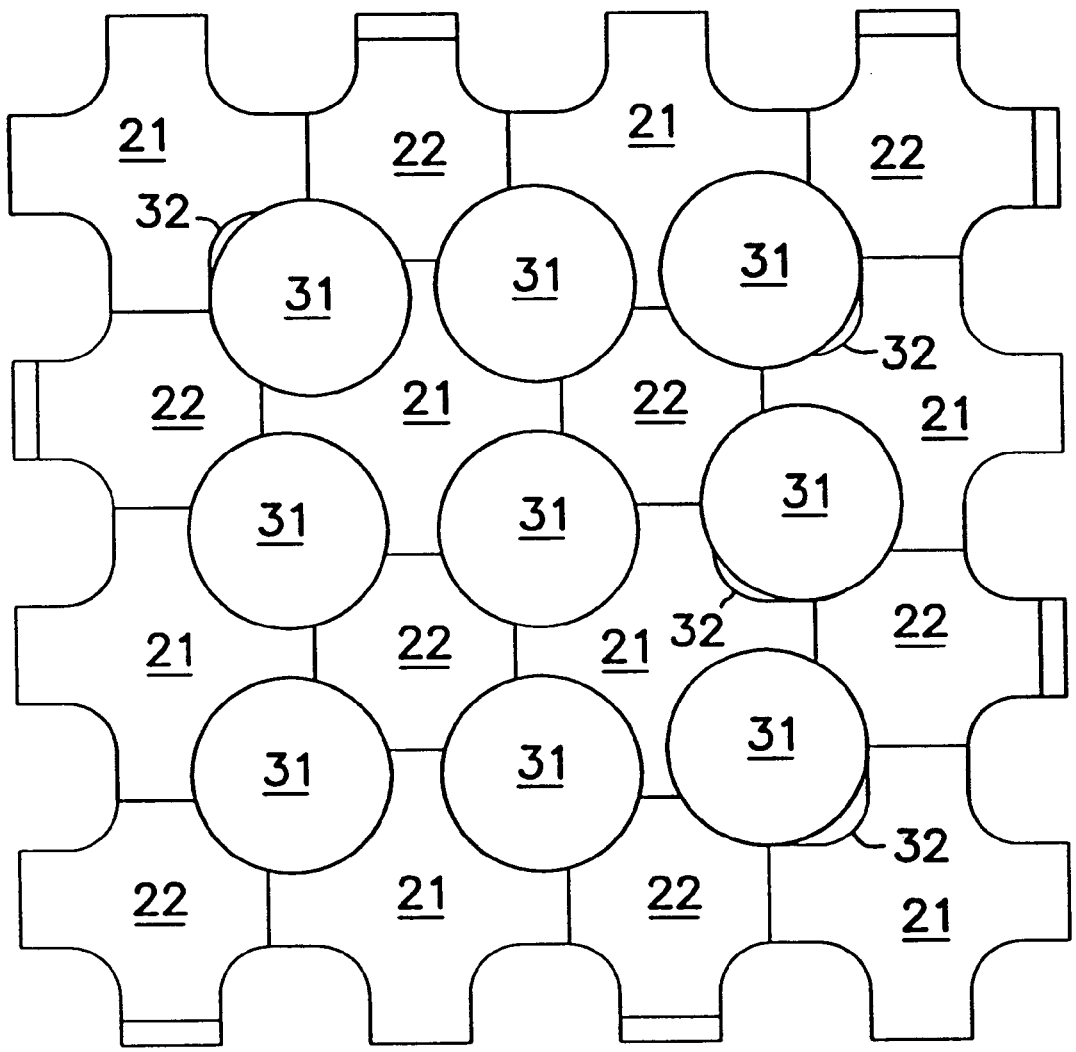
FIG. 13A depicts a fabric with the tops of the rivets too small to cover all of the apertures in a fully stretched configuration.
Figure 13B:
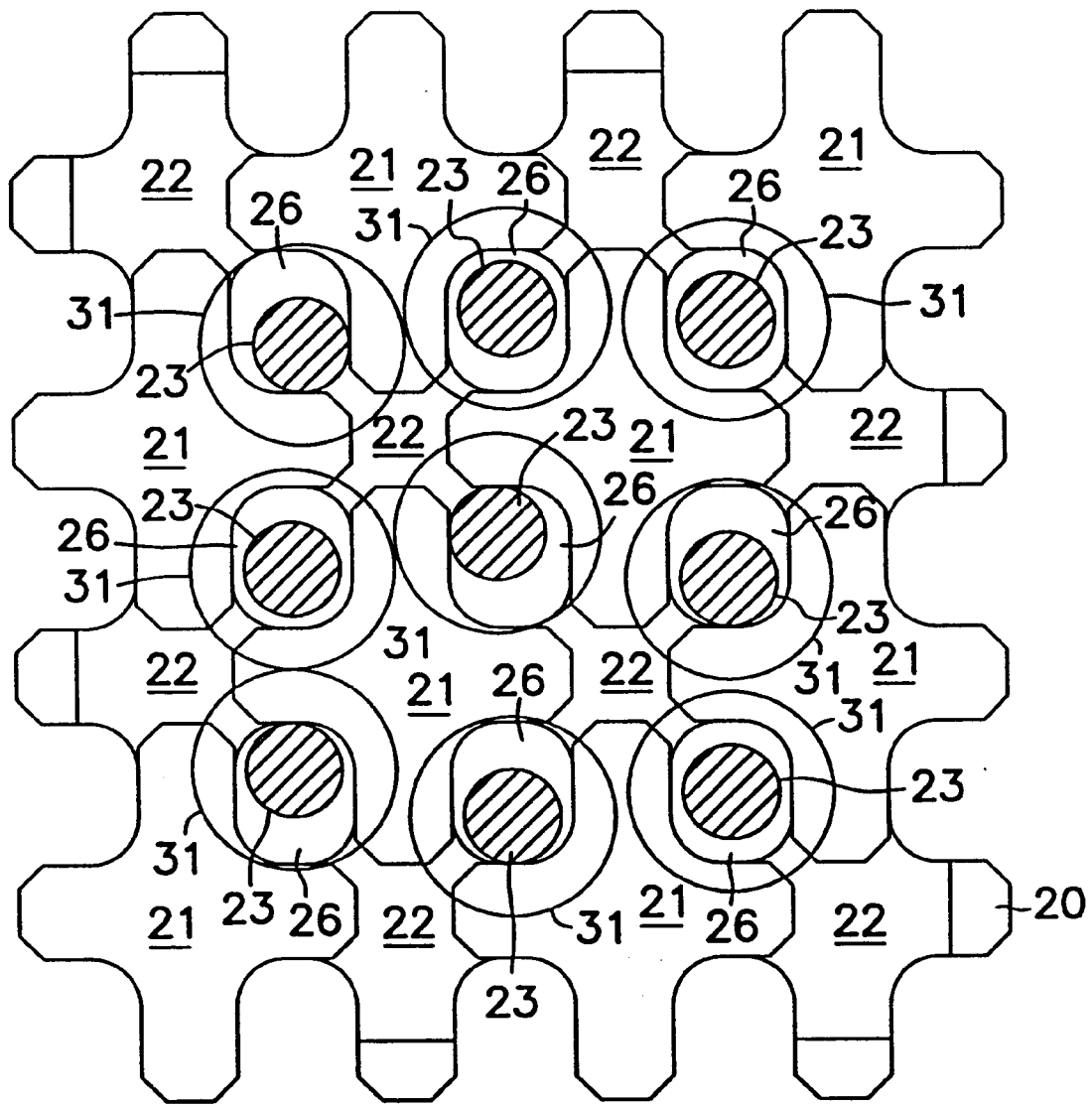
FIG. 13B is a plan view of the fabric with rivets at different locations in the aperture with heads that cover the aperture in each case.

Were it not for the top 31 of the truncated cone 24, the space between the aperture 26 and the pin 23 could be large enough that a needle or other projectile could penetrate the fabric 11. The top 31 of the truncated cone 24, shown in FIG. 3B, must, therefore, be of a diameter that is large enough that when the fabric 11 is fully stretched and pin 23 is in its worst case of having moved to the wall of the aperture 26, the top 31 covers the entire area of the aperture 26 or at least covers the area of the aperture to the extent that the uncovered area is small enough that the projectile for which the fabric is designed to resist can not penetrate. In the best case when the fabric 11 is fully stretched, the pins 23 would all be positioned in the center of the aperture 26. In this case the diameter of the top 31 of the truncated cone 24 would only need to be slightly larger than the diameter of the aperture 26. However, this configuration virtually never occurs. In practice the pins 23 assume a random distribution in the apertures 26. FIG. 13A illustrates a fabric 11 fully stretched. In FIG. 13A the tops 31 of four of the truncated cones 24 are of a diameter that is not large enough to completely cover spaces 32 between some of the rivets 13 and the apertures 26. The tops 31 of the other rivets 13 completely cover the apertures 26. After the fabric 11 is compressed and stretched again the new random distribution of the pins 23 in the apertures 26 will result in a new pattern of open spaces 32 between the apertures 26 and the pins 23. To correct the situation in FIG. 13A, the diameter of the tops must be increased. FIG. 13B illustrates different locations of the rivet 13 in the aperture 26 of a fully stretched fabric 11. The top 31 of the rivet 13 pin 23 has been made large enough that it always covers the aperture 26, regardless of where the pin 23 of the rivet 13 is located in the aperture 26. The size of the rivet 13 top 31 is constrained by the requirement that when the fabric is fully compressed, the tops 31 must not overlap each other. In turn the size of the aperture 26 when the fabric 11 is fully stretched depends upon the extent of stretchability of the fabric 11, which is a function of the length of the tab 15 arms 18. The diameter of the pin 23 of the rivet 13 also has an affect upon the size of the top 31 of the rivet 13 necessary to cover the aperture 26. The smaller the pin 23 cross-section, the larger the top 31 must be to cover the aperture 26.

Figure 14A:
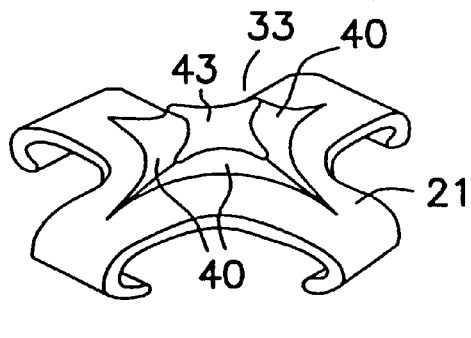
FIG. 14A through F depicts a platelet with a head and plug of an alternate embodiment in perspective, plan, and side views.
Figure 15:
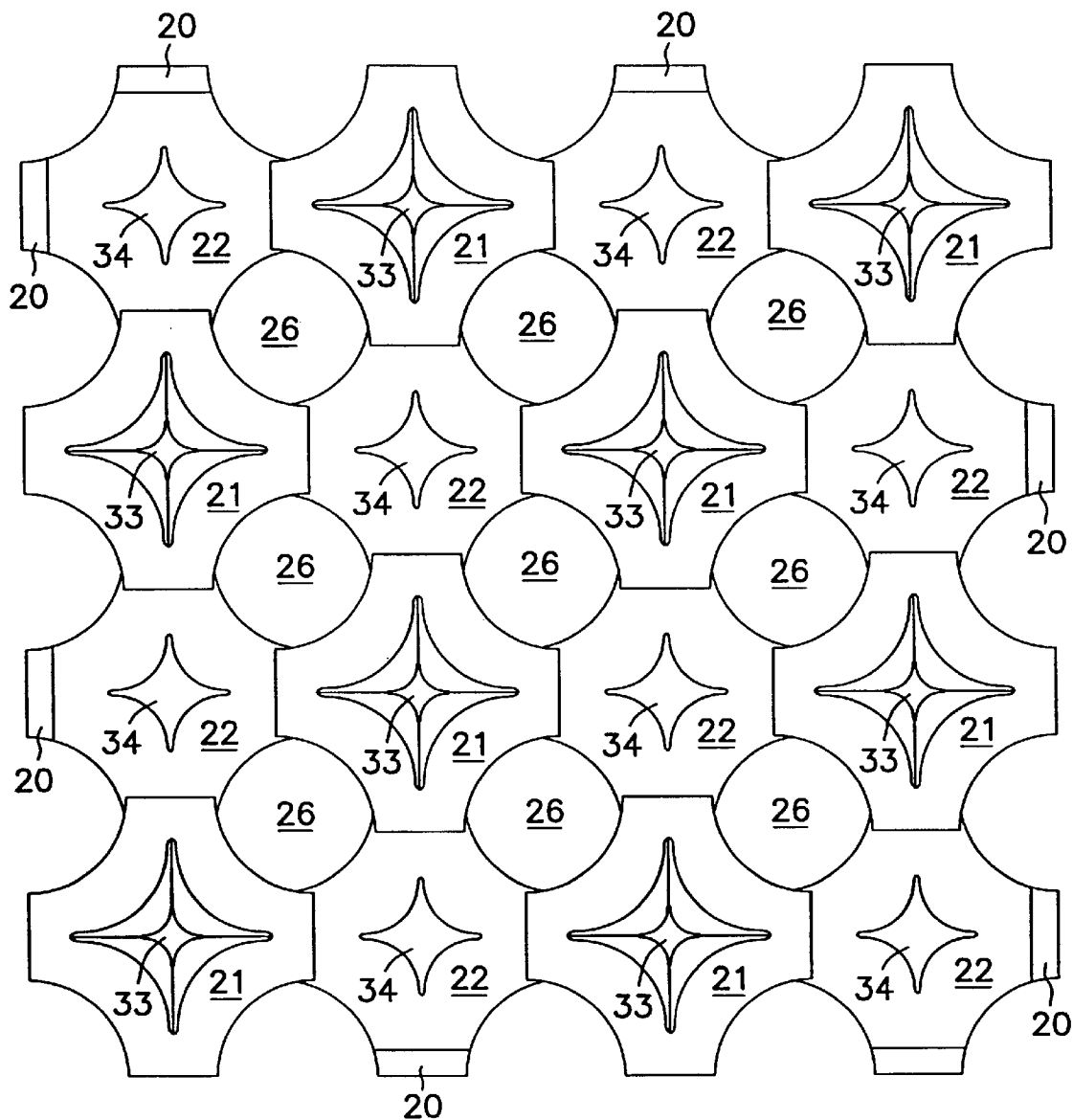
FIG. 15 illustrates the fabric of an alternative embodiment of the invention having heads and plugs with the rivets removed.
Figure 16:
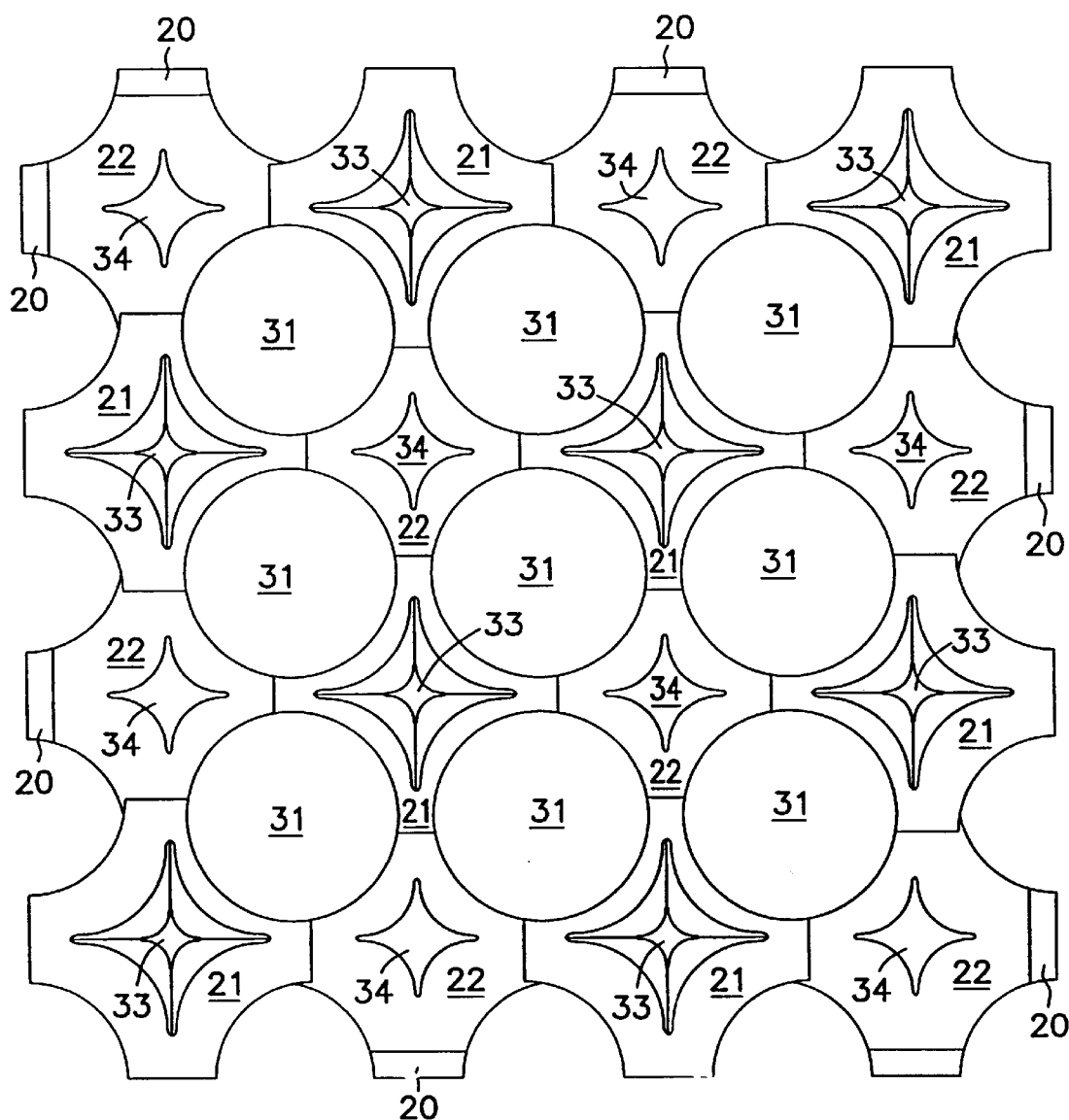
FIG. 16 illustrates the fabric of the alternative embodiment of the invention having heads and plugs with the rivets in place.

The fabric 11 assembled as shown in FIG. 1B in cross-section and in FIG. 1A in a perspective view from the top 21 of the platelet 12 presents an uneven surface, which for some applications may not be optimal. To alleviate the uneven surface, platelets 12, as shown in FIGS. 14, 15, and 16, have a head 33 extending upward from the top 21 of the base 14 portion of the platelet 12 and a plug 34 extending downward from the bottom 22 of the platelet 12. The head, shown in perspective in FIG. 14A is axially aligned with the center of the base 14. Its faces 40 are defined by intersecting cone shapes, which mate with the truncated cone 24 portion of the rivet 13. The top 43 surface of the head 33 is planer and in a plane parallel with the plane of the base 14 of the platelet 12. The height of the head 33 above the platelet 12 base 14 is the same as the height that the truncated cone 24 portion of the rivet 13 rises above the plane of the base 14 of the platelet 12. FIGS. 14B and C further illustrate the shape of the head 33.

Figure 14D:
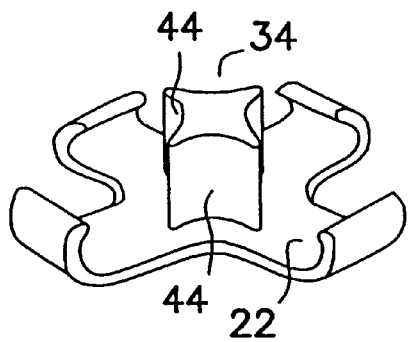
Figure 14B:
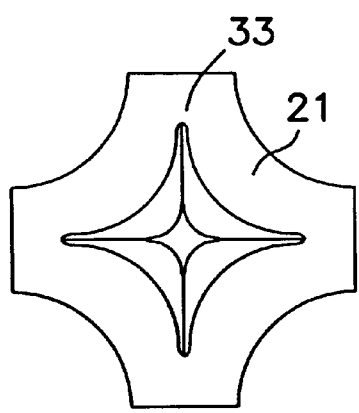
Figure 14E:
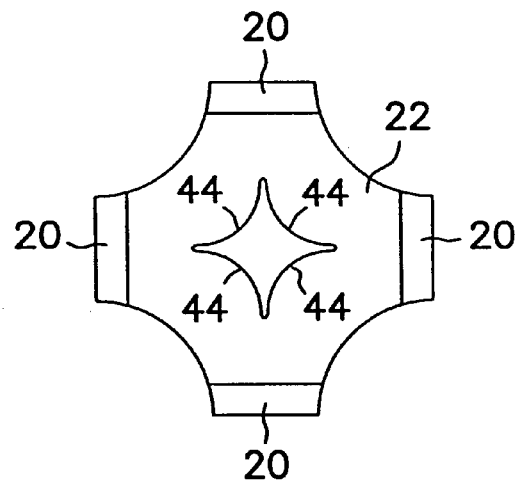
Figure 14C:
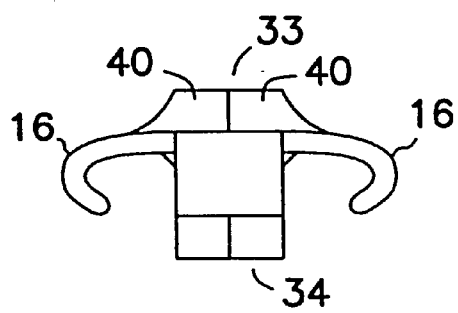
Figure 14F:
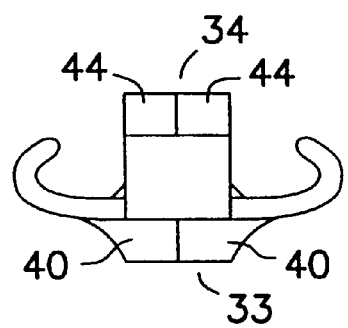

The plug 34, shown in perspective in FIG. 14D, is axially aligned with the center of the bottom 22 of the base 14 of the platelet 12. Its faces 44 are defined by a radius equivalent to the radius of the top 31 of the truncated cone 24 for loose mating engagement with the top 31 of the truncated cone 24 when the fabric 11 is fully compressed. FIGS. 14C and F show the head 33 and the plug 34, respectively, affixed to the top 21 and the bottom 22 surface of the platelet 12 from the side.

FIGS. 15 and 16 depict the alternate embodiment of the fabric 11 with the heads 33 and the plugs 34. FIG. 15 has the truncated cones 24 of the rivets 13 removed to better illustrate the spatial relationship of the rivets 13, heads 33, and the plugs 34. FIG. 16 shows the rivets 13 with the top 31 of the truncated cones 24 in place. This figure shows how the tops 31 of the truncated cones 24 loosely mate with the heads 33 and with the plugs 34 to allow movement relative to one another, for example rotational movement of the rivets, and also close packing density when the fabric 11 is at its fully compressed position as it is shown in FIGS. 15 and 16. As illustrated in FIG. 16, the flat top surfaces of the heads 33, which rise to the same level as the tops 31 of the truncated cones 24 gives a more overall even surface to the fabric 11. There remains some texture to the fabric 11 since the heads 33 and the plugs 34 do not completely infill the fabric 11, especially when the fabric 11 is fully stretched. However, the depressed surface area is largely relieved, which satisfies even the most demanding applications.

The invention has been described with a platelet 12 having tabs 15 extending from its base 14. This shape is a preferred embodiment, but the fabric of the invention may also be constructed of solid objects of different shapes. For example, an equal sided triangular shape also results in a fabric 11 that possesses the desired flexibility, bendability, and twistability. With the use of a modified rivet, such a fabric may also be constructed without gaps so that a needle or other projectile is stopped from penetrating the fabric 11.

Another embodiment of the invention is illustrated in FIGS. 17 through 23. FIG. 17A depicts a fabric 11 constructed from a modified platelet 12 and a modified rivet 13. The modified platelet 12 has bevels 35 at the distal end of the each tab 15 where the tab edge 25 and the distal end of the tab 15 meet. The edges 25 of adjacent tabs 15 of the same platelet 12 are connected by a straight edge 36 having as a point in the straight edge 36 the intersection of the edges 17 of the base 14 of the platelet 12 (shown in dotted lines in FIG. 17A) and terminating at the intersection of the straight edge 36 and the edge 25 of one tab 15 and on the other end of the straight edge 36 at the intersection with the edge 25 of the adjacent tab 15 so that the edges 25 of the tabs 15 in which the straight edge 36 terminates are both of the same length.

Figure 17A:
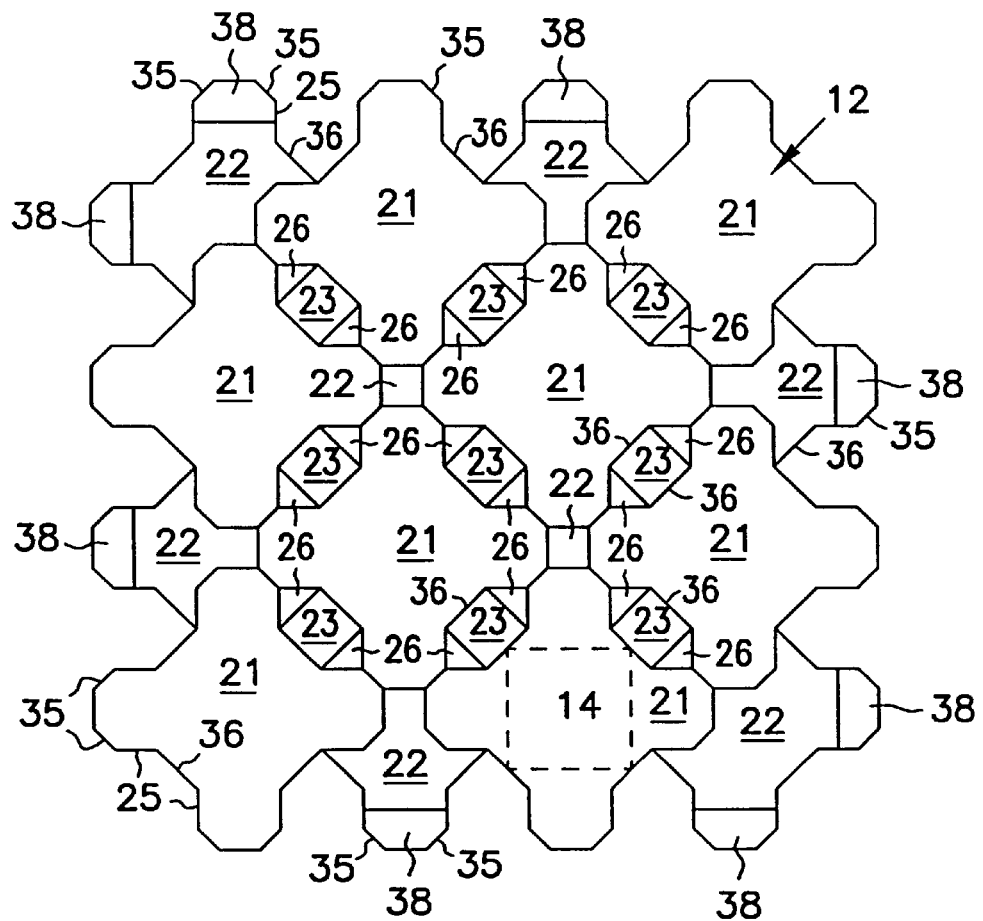
FIG. 17A is a further alternative embodiment of the fabric in the most compressed configuration having beveled edges on the tab distal ends and between tabs, shown without rivets.
Figure 17B:
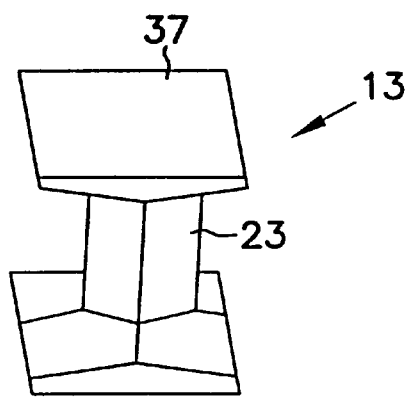
FIG. 17B is a perspective view of the rivet to be used with the embodiment shown in FIG. 17A.

The pin 23 of the rivet 13 instead of being round is square. Each side of the square pin 23 is the same length as the straight edge 36 of the platelet 12. This embodiment allows for an even closer packing of the platelets 12 than the design using round pins 23. In this embodiment, the platelets 12 and the pins 23 nest closer together as shown in FIG. 17 when in the fully compressed configuration. FIG. 17B illustrates the square pin 23 and square plate rivet head 37 of this embodiment.

Figure 18:
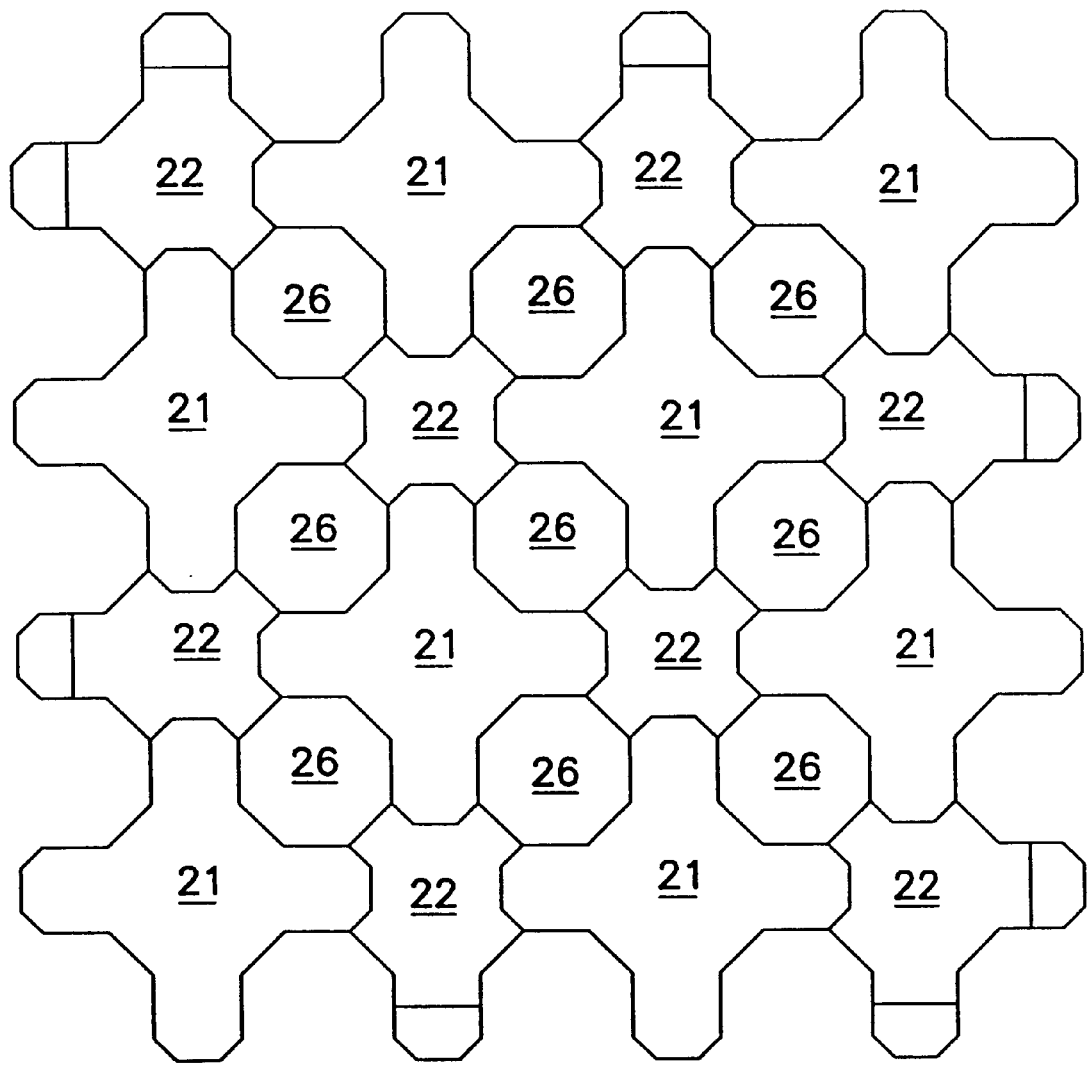
FIG. 18 illustrates the alternative embodiment fabric of FIG. 17 in its most stretched configuration without rivets.
Figure 19:
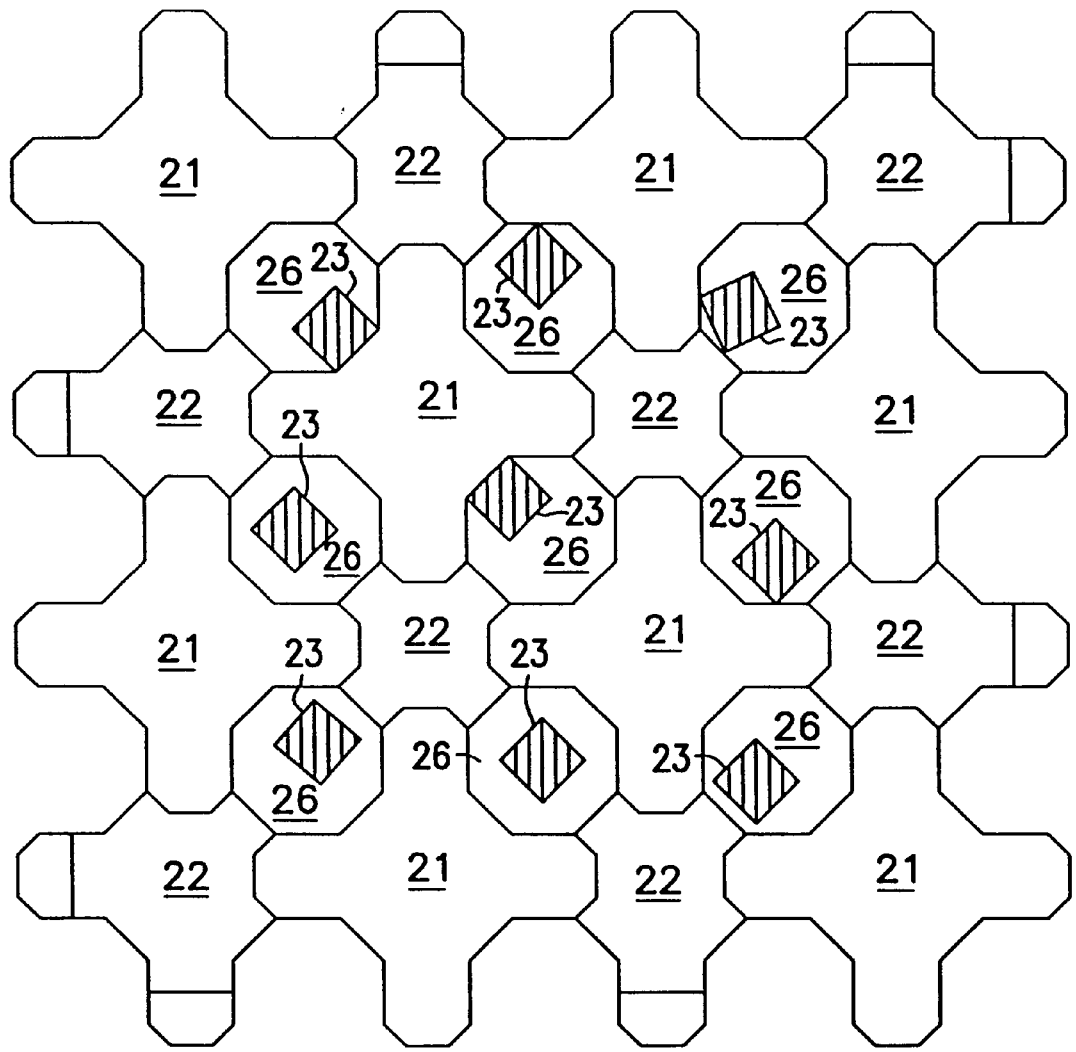
FIG. 19 is the same as FIG. 18 except that square pin portions of alternative embodiment rivets are inserted.
Figure 20:
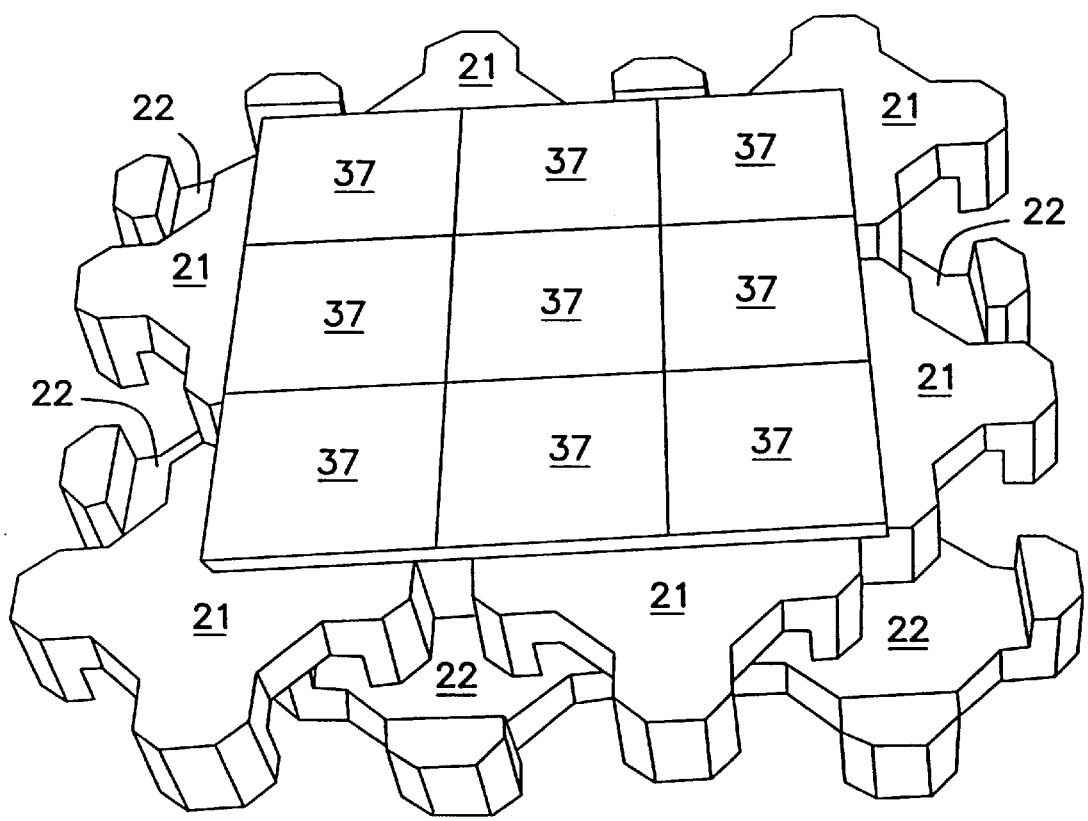
FIG. 20 shows the square plate rivet heads of the alternative embodiment rivet in the fabric shown in FIG. 17 in its compressed state.
Figure 21:
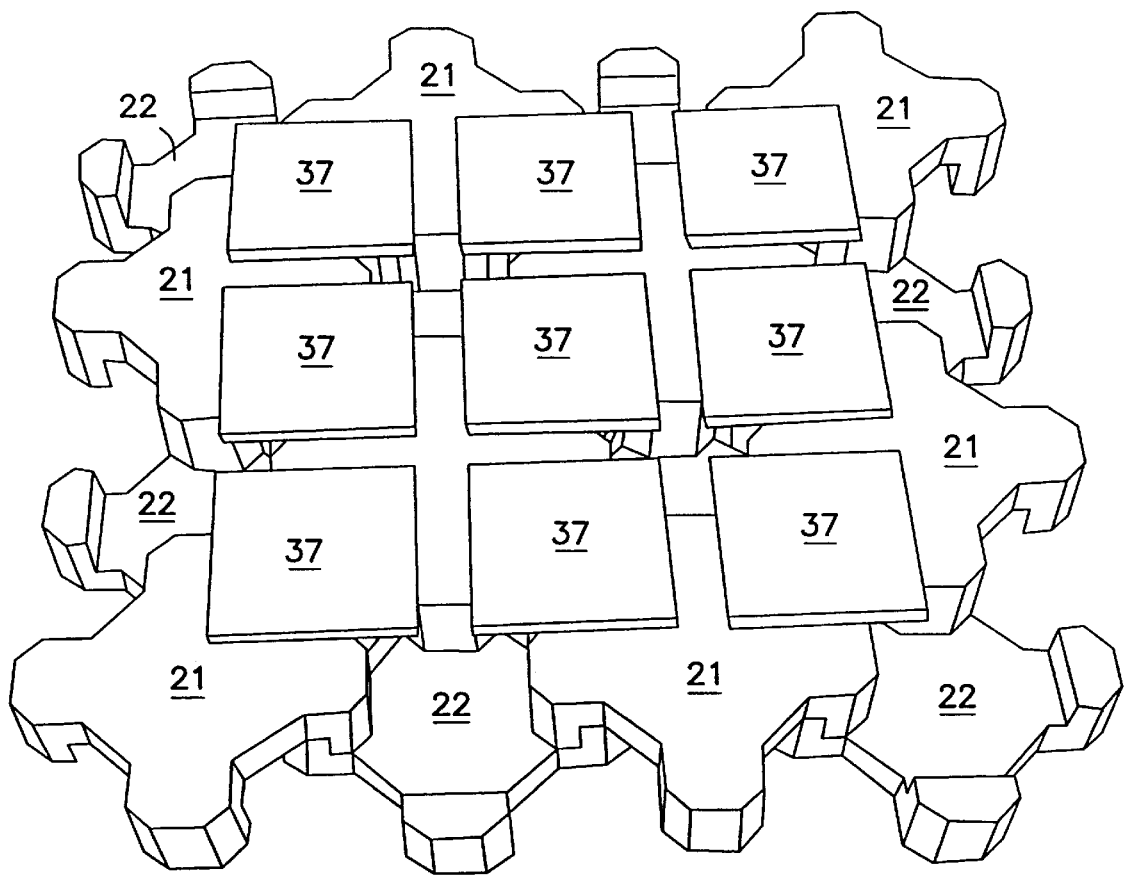
FIG. 21 depicts the fabric of FIG. 20 in a fully stretched state with the square plate rivet heads.
Figure 22:
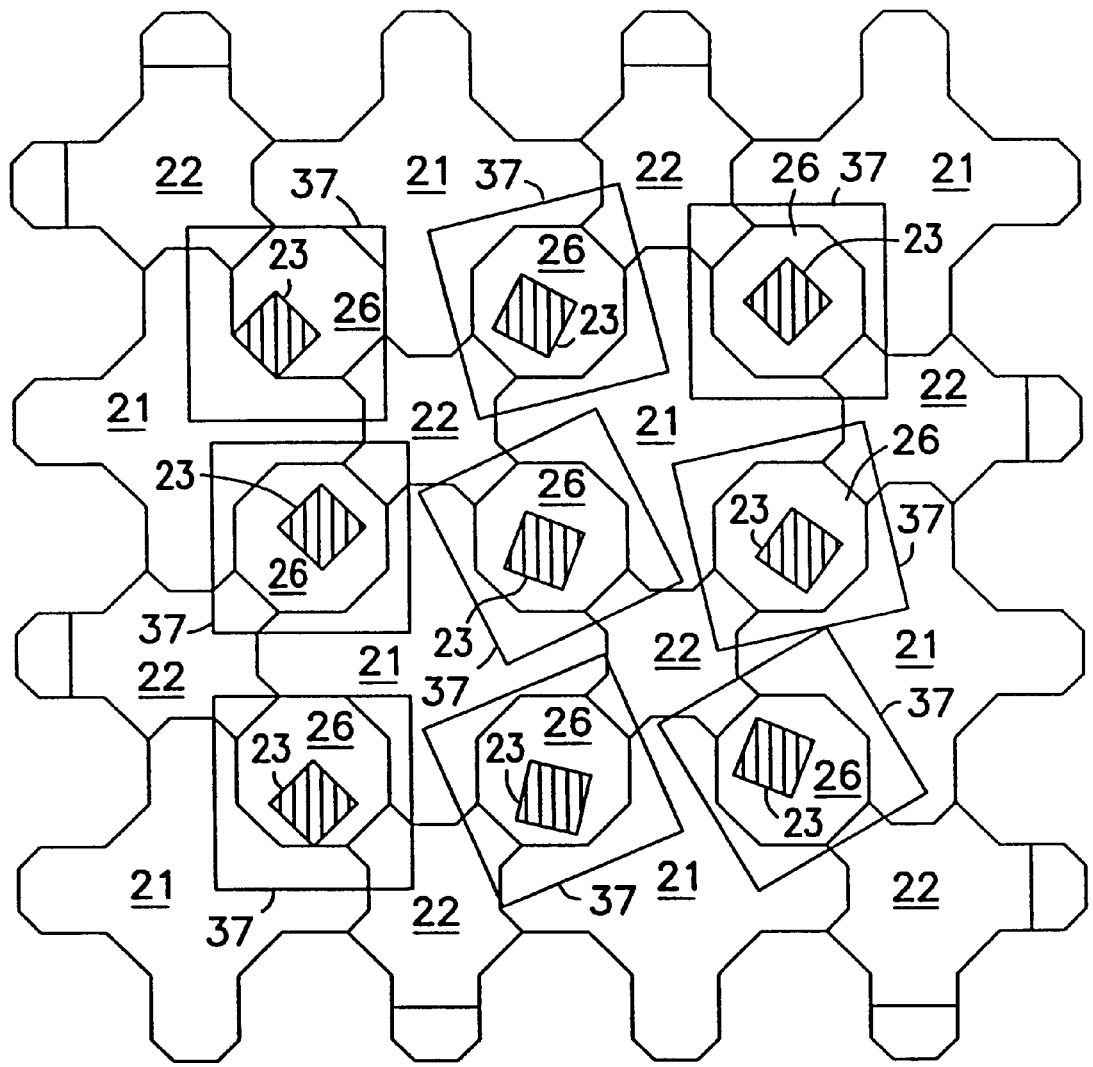
FIG. 22 shows a portion of the fabric of the alternative embodiment with the rivets in place in differing locations with the square plate rivet heads fully covering the apertures.
Figure 23A:
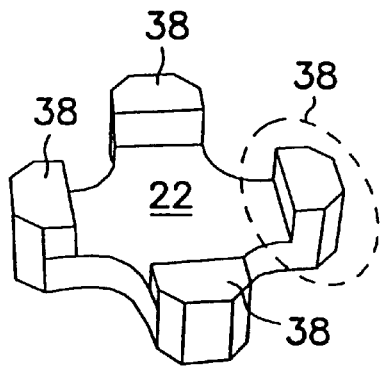
FIG. 23 depicts an alternative embodiment platelet with a planar hook.
Figure 23D:
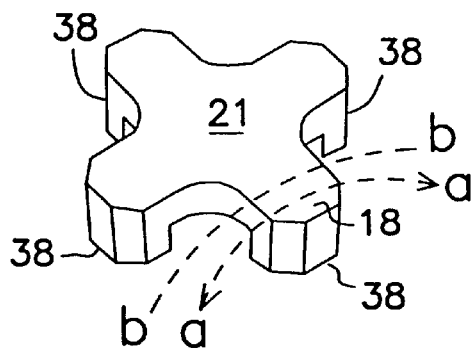
Figure 23B:
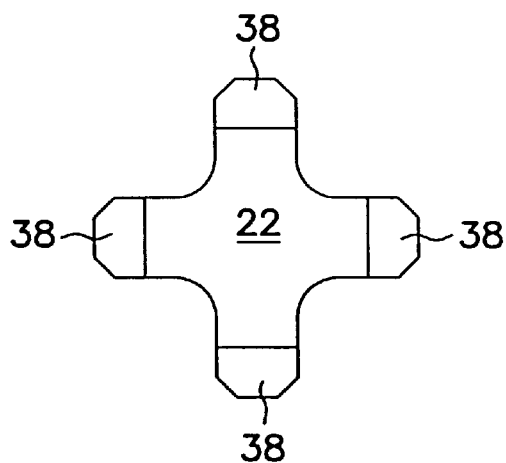
Figure 23E:
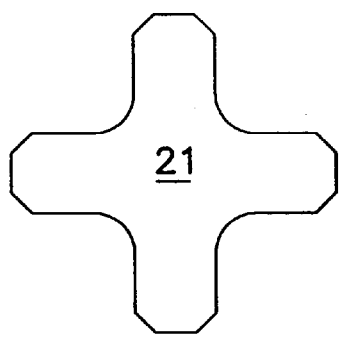
Figure 23C:
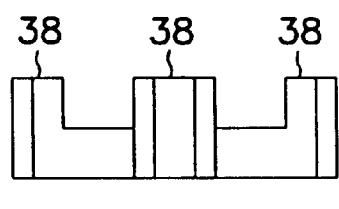
Figure 23F:
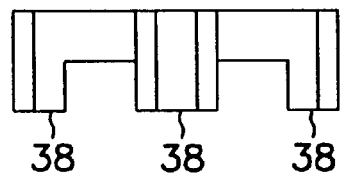

FIG. 18 illustrates the fabric 11 of this embodiment in its fully stretched configuration without the pins 23 inserted. Without the pins 23 inserted it can clearly be seen that the aperture 26 is octagonal in shape. FIG. 19 shows the fabric 11 of this embodiment in its fully stretched configuration with the pins 23, illustrating that the pins 23 of the rivets 13 are loosely fitted into the aperture 26 made by the surrounding adjacent platelets 12. FIG. 20 shows the fabric 11 in its fully compressed configuration. The rivet 13 instead of terminating in a truncated cone 24, terminates in a square plate rivet head 37. When the fabric 11 is fully compressed, the rivets 13 are forced into the rectilinear configuration shown in FIG. 20. This configuration promotes stretchability by allowing for the large surface area of the square plate rivet head 37, which provides maximum coverage of the large aperture 26 formed when the fabric 11 is stretched to the maximum and yet does not retard compression of the fabric 11 because it nests compactly in the rectilinear shape. FIG. 21 shows the fabric 11 in the stretched mode and illustrates the complete coverage of all of the apertures 26, providing a continuous closed web of fabric 11 which will resist penetration. FIG. 22 shows a portion of the fabric 11 of FIG. 21 with the square plate rivet head 37 of the rivet 13 and the square pin 23. The rivet 13 the pin 23 in the upper left hand position of FIG. 22 has moved adjacent to the side of the aperture 26 while the other rivets 13 have moved to other random positions. Even in these randomly diverse positions, the square plate rivet heads 37 cover the apertures 26. The square plate rivet heads 37 cover the apertures 26 even though they are not oriented in a rectilinear configuration, but in a random configuration.

Figure 24A:
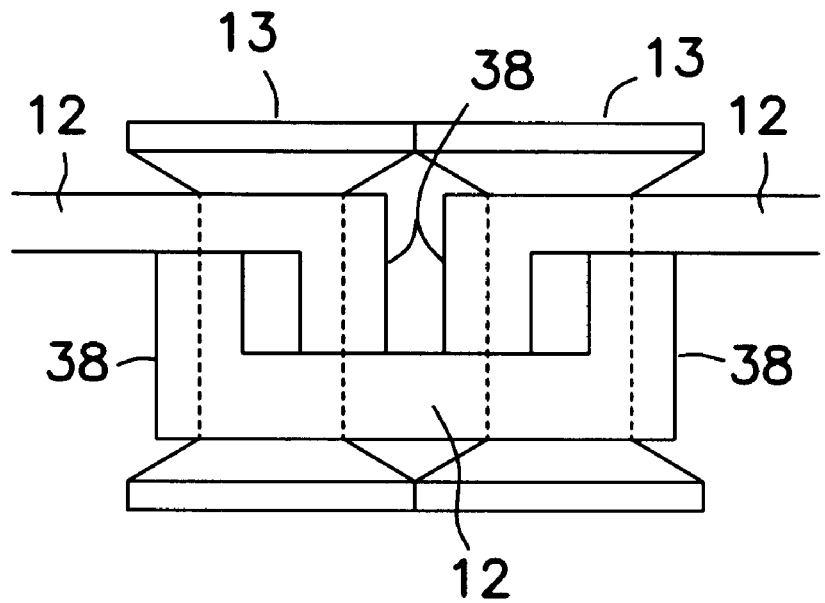
FIG. 24A and 24B shows a cut away elevation view of the invention using the platelet with the planar hook in the compressed and stretched configurations, respectively.
Figure 24B:
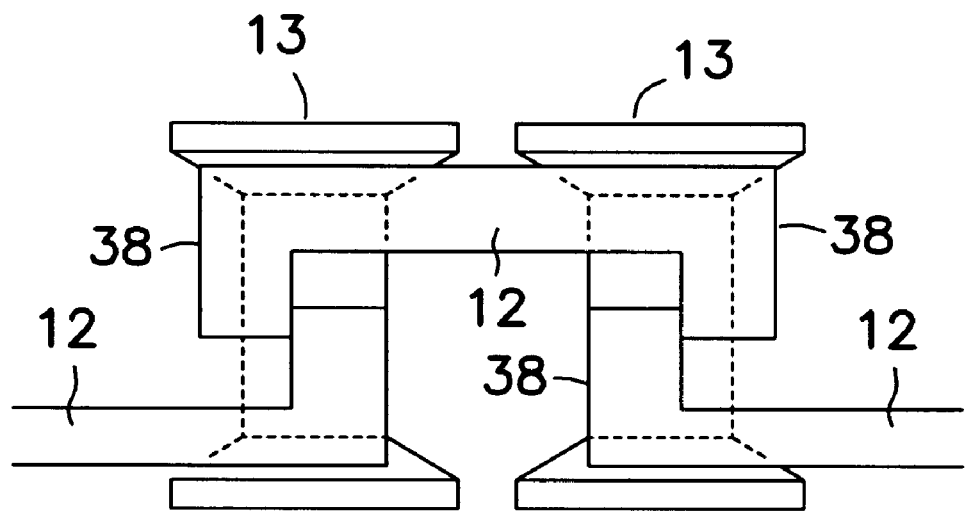

An alternative to the platelet 12 shown in FIG. 2 is depicted in FIG. 23. The arm 18 of the tab 15, which lies between dotted lines a—a and b—b in FIG. 23D, terminates in planar hook 38, shown in the dotted circle 38 in FIG. 23A, depending downward from the plane of the arm 18 and the base of the platelet 12 at a right angle to the plane of the arm 18. FIG. 23A shows the alternative embodiment in a perspective view form the bottom side. The planar hook 38 is shown with a thickness greater than the thickness of the base 14 of the platelet 12. This additional wall thickness may be added for some very demanding applications where tear strength parallel to the plane of the fabric must be high, such as for body armor. Additional wall thickness may increase the cost of manufacturing somewhat. For most applications a wall thickness the same as the base 14 of the platelet 12 is adequate. FIG. 23D shows the platelet 12 from the top. FIGS. 23B through F are plan and elevation views of the alternative embodiment of the platelet. This alternative embodiment platelet 12 configuration lends itself to somewhat lower manufacturing and assembly costs. FIG. 24A shows the alternative embodiment in a cut-away cross section with rivets 13 in a fully compressed state. FIG. 24B illustrates the fully stretched state.

FIG. 25 depicts how the truncated cone 24 facilitates bending of the fabric 11 with the alternative embodiment platelet 12 having the planar hook 38. The truncated cone 24 also facilitates bending with the platelet 12 with the hook 16 with the reverse tab 20.

Figure 26A:
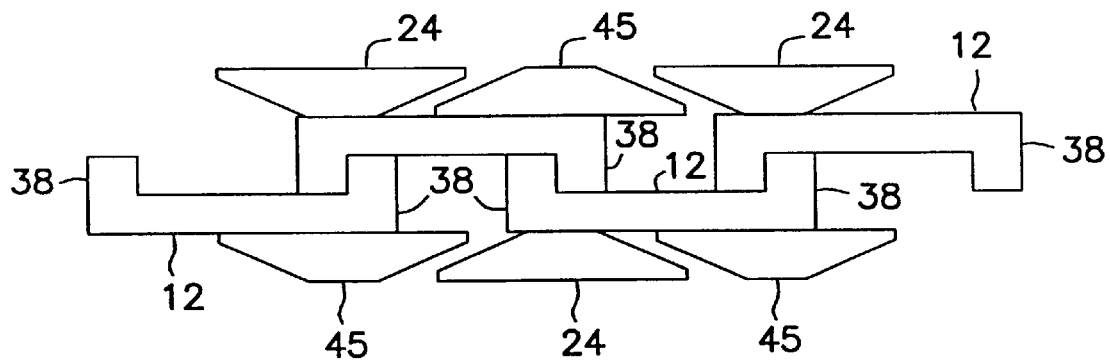
FIGS. 26A and 26B shows elevational views of an alternative embodiment of the fabric incorporating alternate rivets having inverted truncated cones.
Figure 26B:
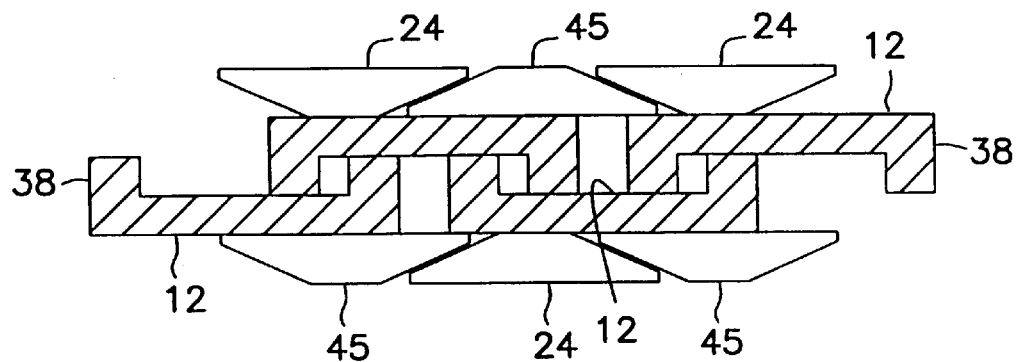
Figure 27A:
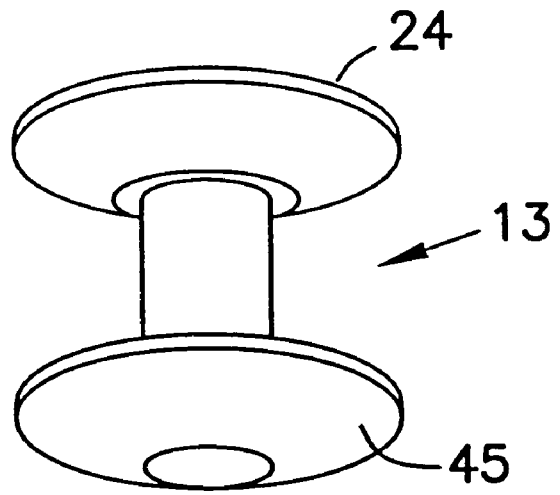
FIG. 27A shows a perspective views of the rivet shown in FIGS. 26A and 26B.
Figure 27B:
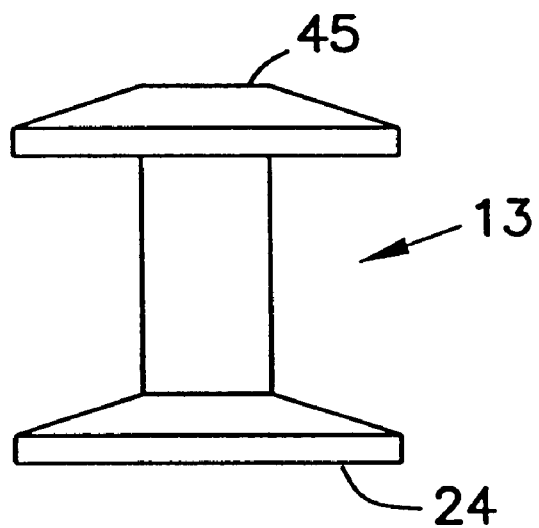
FIG. 27B is an elevational view of the rivet.

FIGS. 26A and B show yet another alternative embodiment fabric 11. In this embodiment, alternate rivets 13 have their truncated cones 24 inverted. When the fabric 11 is stretched, as shown in 26A, the platelets 12 pull apart until they are restrained by the overlapping planar hook 38. If the fabric 11 must bend, the truncated cones 24 and the inverted truncated cones 45 slide upward over each other to allow the bending. When the fabric 11 is compressed, as shown in FIG. 26B, the truncated cones 24 and inverted truncated cones 45 fully nest together. The truncated cones 24 and inverted truncated cones 45, as shown in FIGS. 26A and B, present a solid surface to a puncturing instrument in either the fully compressed state or the fully stretched state. When the fabric 11 is extended, FIG. 26A, the diameter of the truncated cones 24 and inverted truncated cones 45 is large enough that there is overlap to stop the penetration of a projectile or sharp instrument. FIG. 27A is a perspective view and FIG. 27B is an elevational view of a rivet 13 with one of its truncated cones 24 inverted.

Figure 28A:
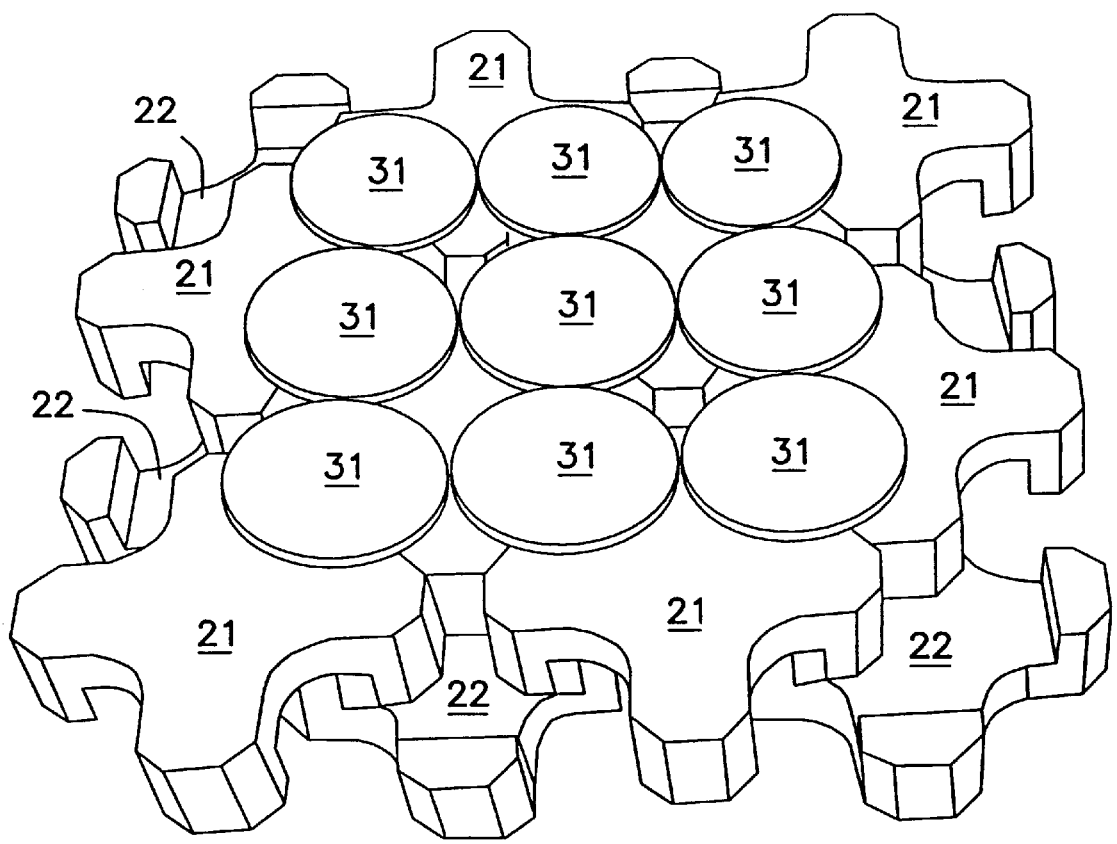
FIG. 28A illustrates a further embodiment of the fabric with platelets having a rounded edge between tabs and beveled distal tab ends in a compressed configuration.
Figure 28B:
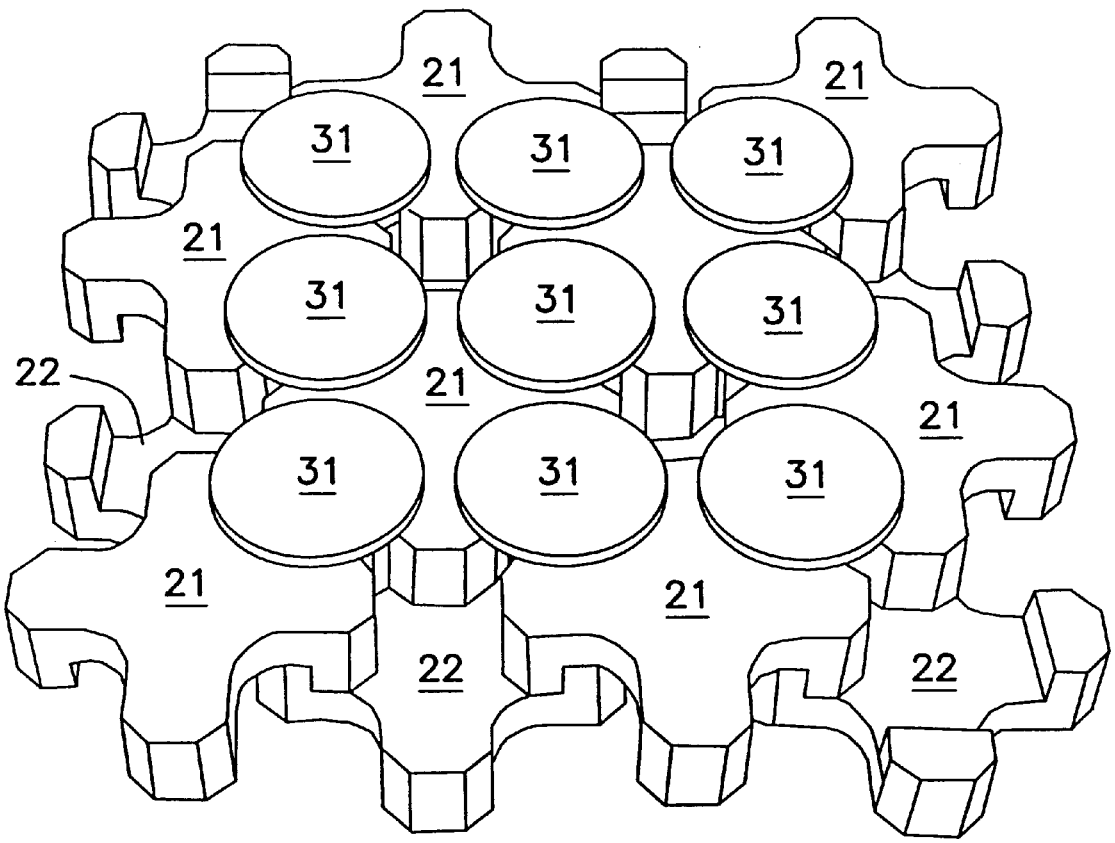
FIG. 28B illustrates the fabric of 28A in a stretched configuration.

FIGS. 28A and 28B illustrate a further embodiment of the fabric 11 with platelets 12 having a rounded edge 25 between tabs 15 and tab bevels 35 on the distal end of the tabs 15 in a compressed and a stretched configuration, respectively.

Figure 29A:
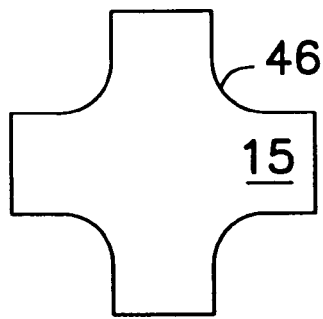
FIG. 29A is a plan view of a planar platelet.
Figure 29B:
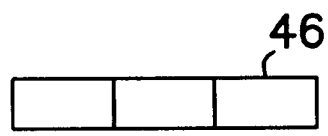
FIG. 29B is a side view of a planar platelet.
Figure 29C:
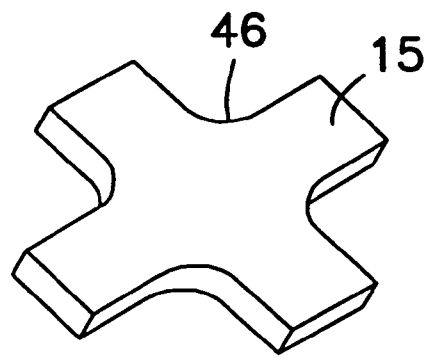
FIG. 29C is a perspective view of a planar platelet.

Another embodiment of the invention uses a planar platelet 46 as illustrated in FIGS. 29A, 29B, and 29C. The planar platelet 46 is a platelet 12 without hooks 16. The configuration of the planar platelet 46 is similar, in other respects, to the platelet 12 illustrated in FIGS. 2, 4, 14, and 23. The fabric 11 is constructed with or without rivets 13, depending upon the application.

Figure 30A:
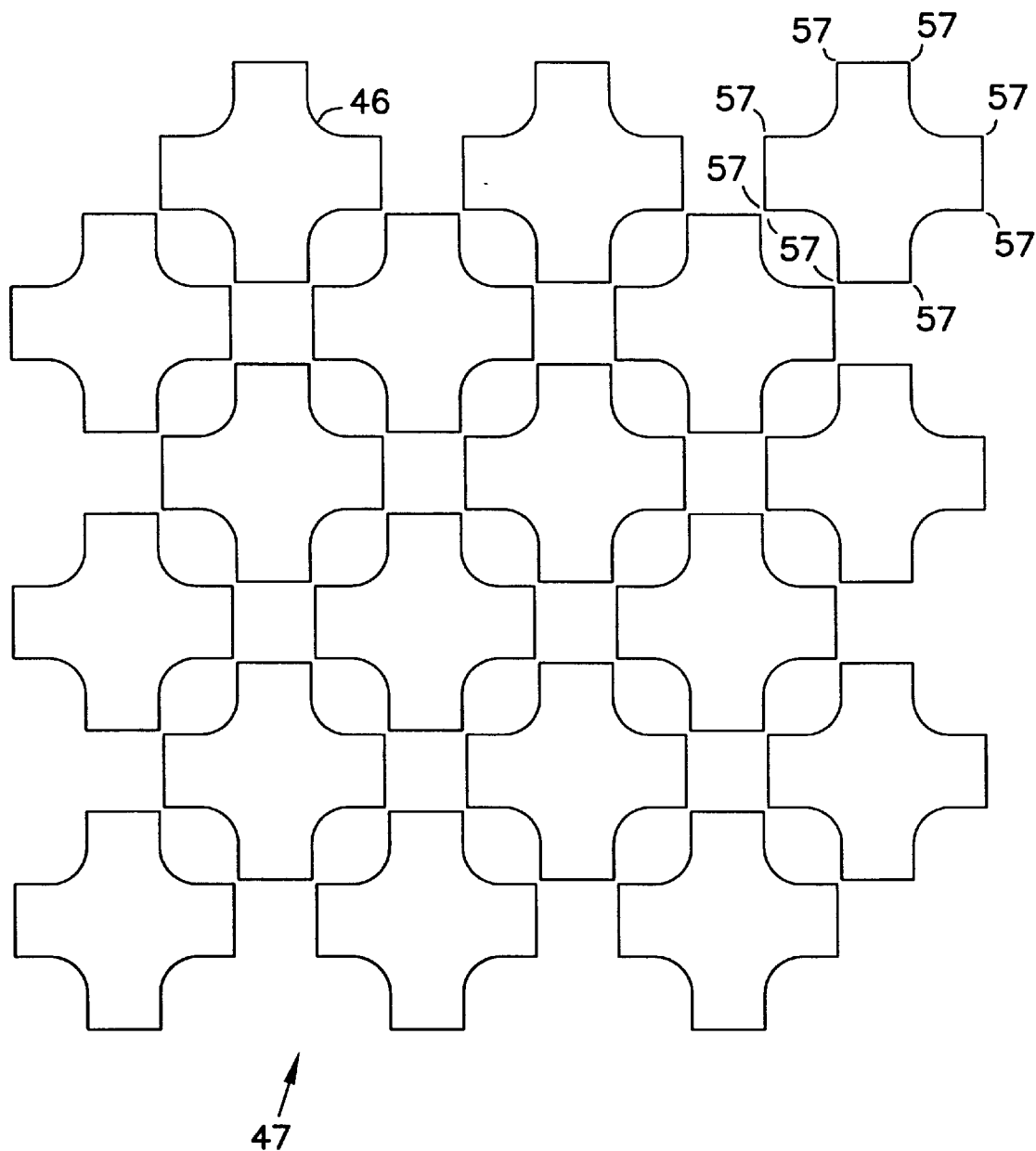
FIG. 30A is a plan view of a sheet of planar platelets in a compressed configuration.
Figure 30B:
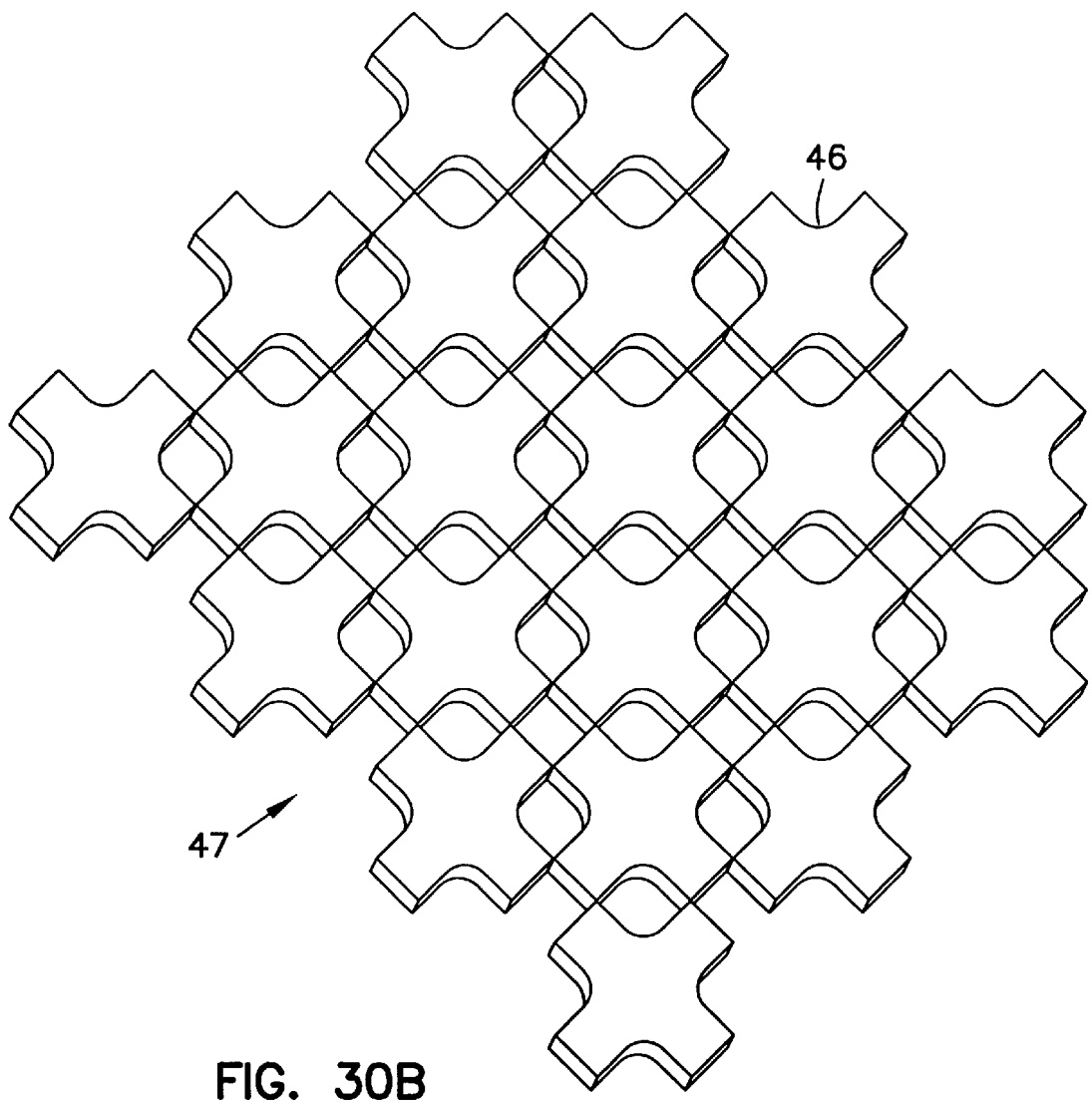
FIG. 30B is a perspective view of a sheet of planar platelets in a compressed configuration.
Figure 31A:
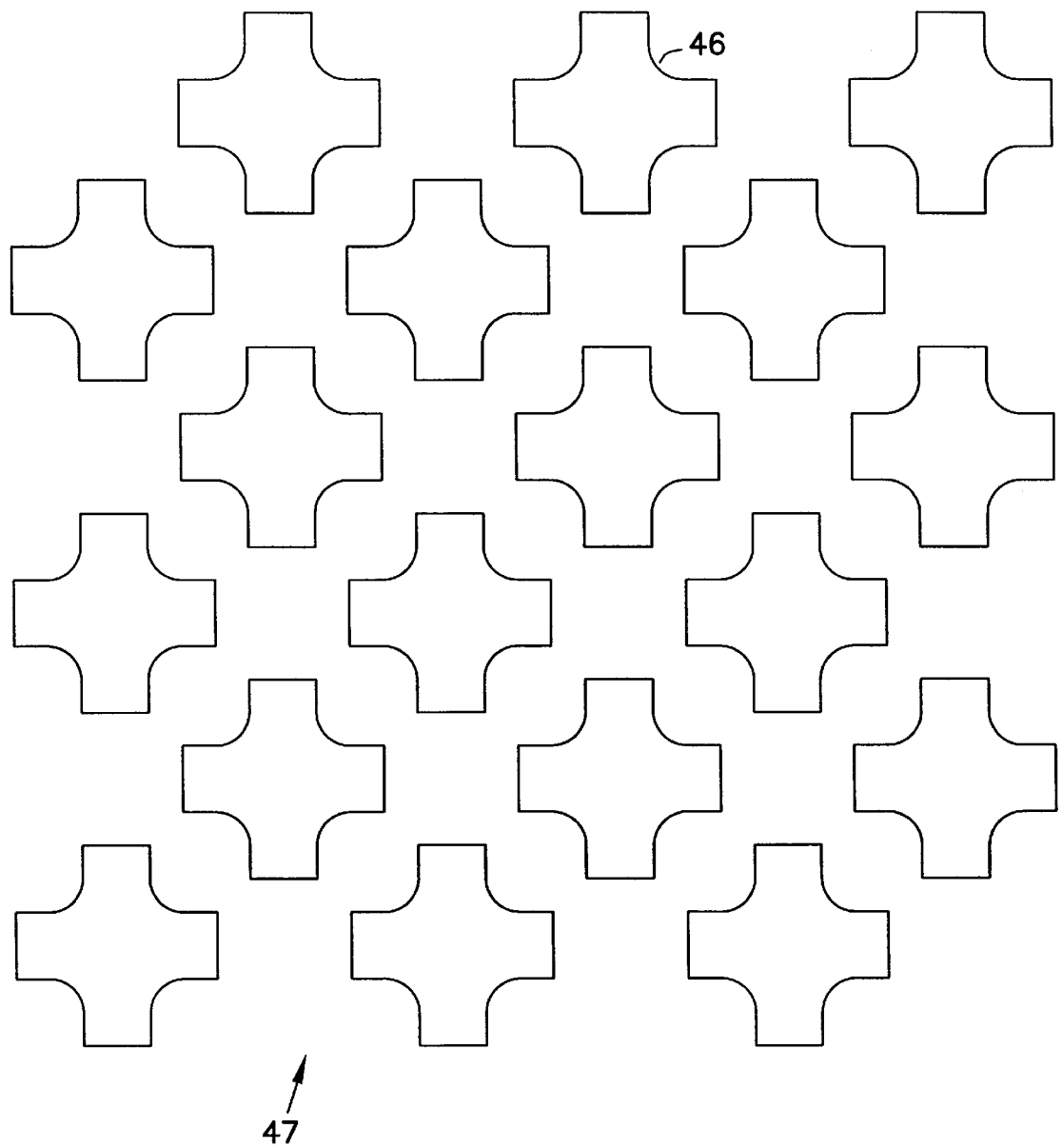
FIG. 31A is a plan view of a sheet of planar platelets in a stretched configuration.
Figure 31B:
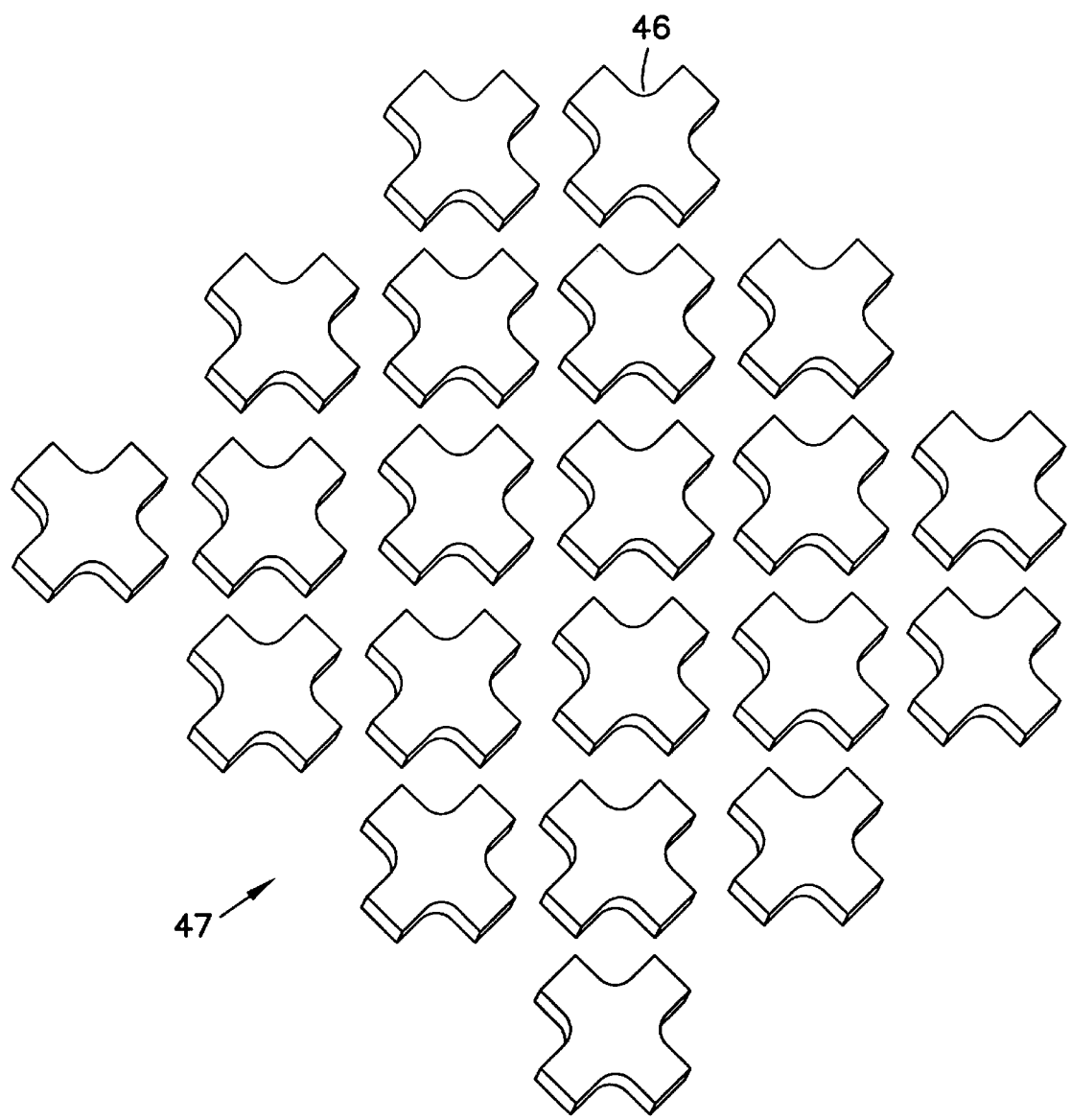
FIG. 31B is a perspective view of a sheet of planar platelets in a stretched configuration.

FIGS. 30A and 30B illustrate a single sheet 47 configuration of the fabric 11 constructed using planar platelets 46. The single sheet 47 is configured in the same layout as the fabric 11 using platelets 12. The sheet of fabric 11 whether constructed of solid objects in the form of plates 65, platelets 12, or planar platelets 46 is arranged in a repeating pattern of the solid objects in a plane. The fabric 11 constructed of planar platelets 46 is arranged in a repeating pattern so that the distal end of each tab 15 forms a right angle with the distal end of adjacent tabs 15 of adjacent planar platelets 46 with a corner 57 of the distal end of each adjacent tab 15 forming the apex of a right angle, as shown in FIG. 30A. FIGS. 30A and 30B illustrate planar platelets 46 in a compressed state. FIGS. 31A and 31B illustrate the fabric 11 with planar platelets 46 in a fully stretched position.

Figure 32A:
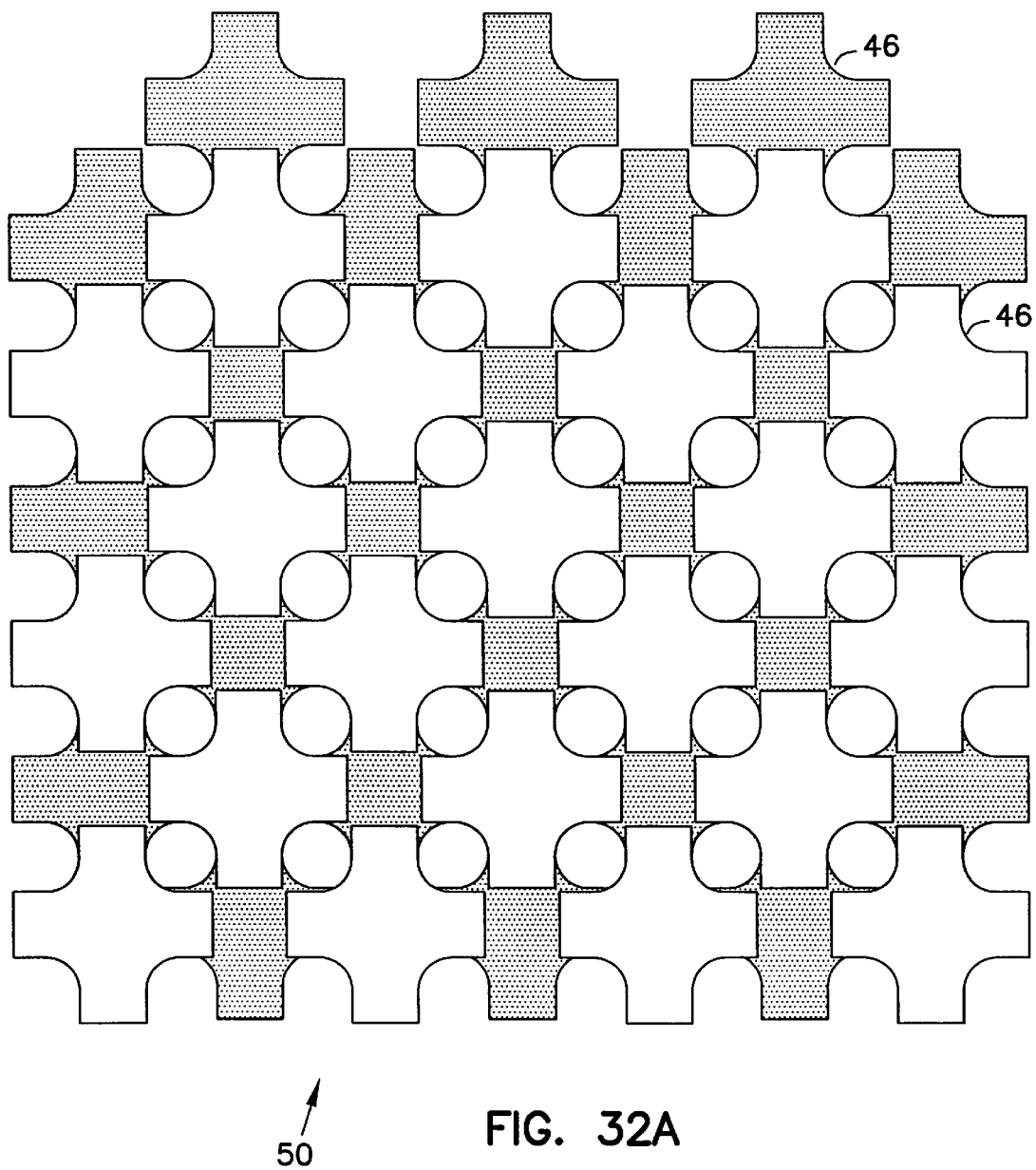
FIG. 32A is a plan view of two sheets of planar platelets arranged in a stack in a compressed configuration.
Figure 32B:
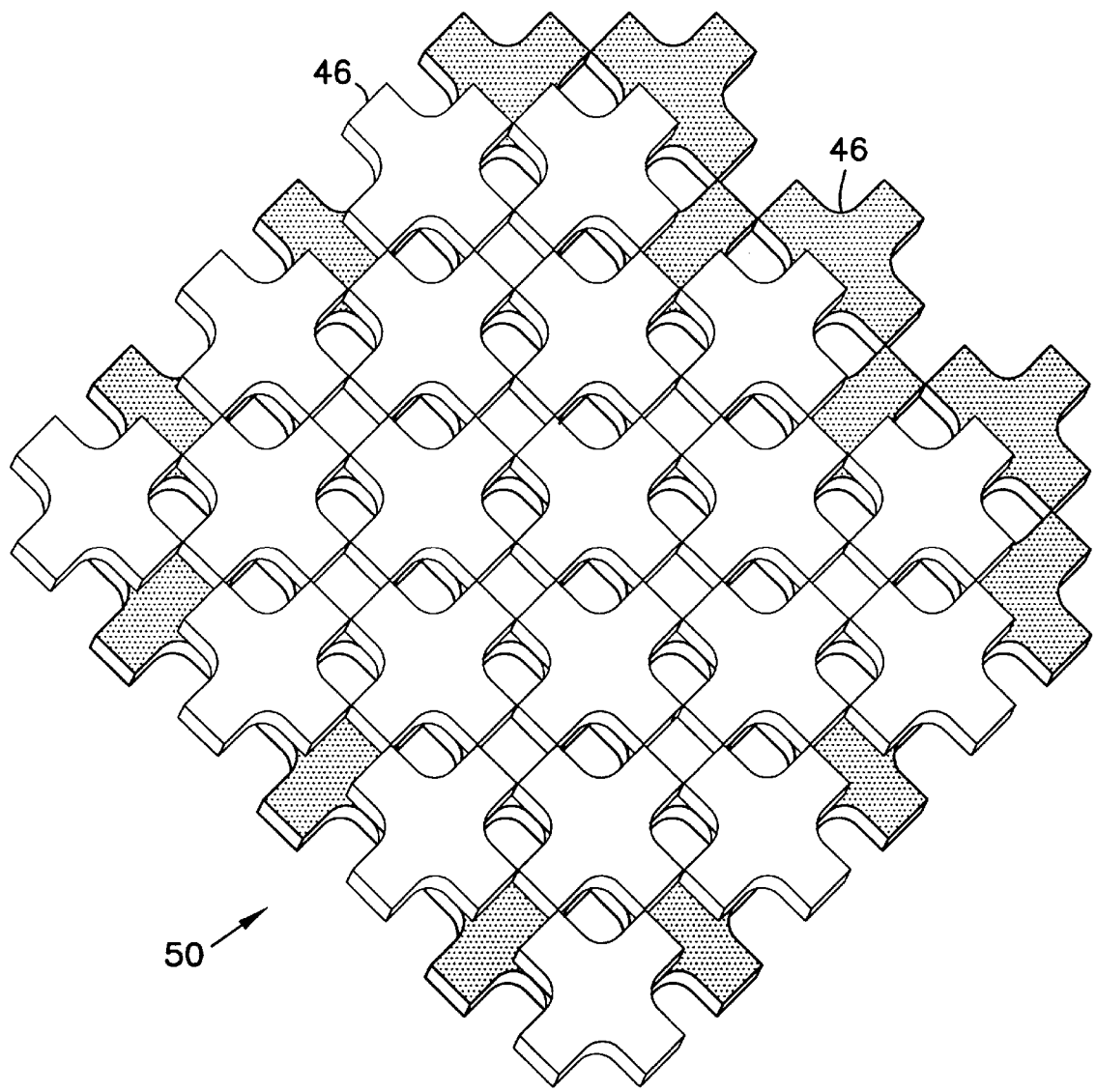
FIG. 32B is a perspective view of two sheets of planar platelets arranged in a stack in a compressed configuration.
Figure 33A:
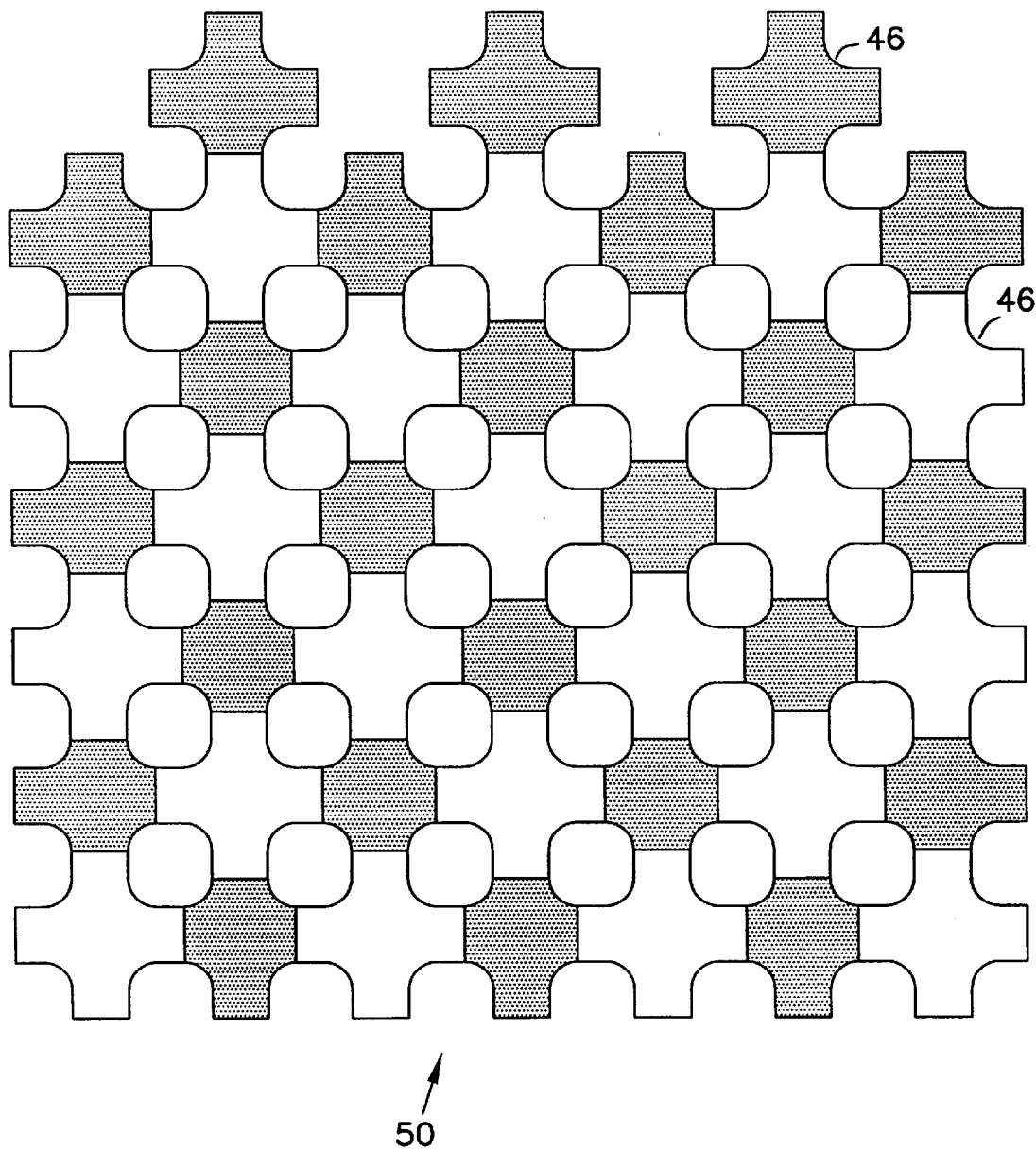
FIG. 33A is a plan view of two sheets of planar platelets arranged in a stack in a stretched configuration.
Figure 33B:
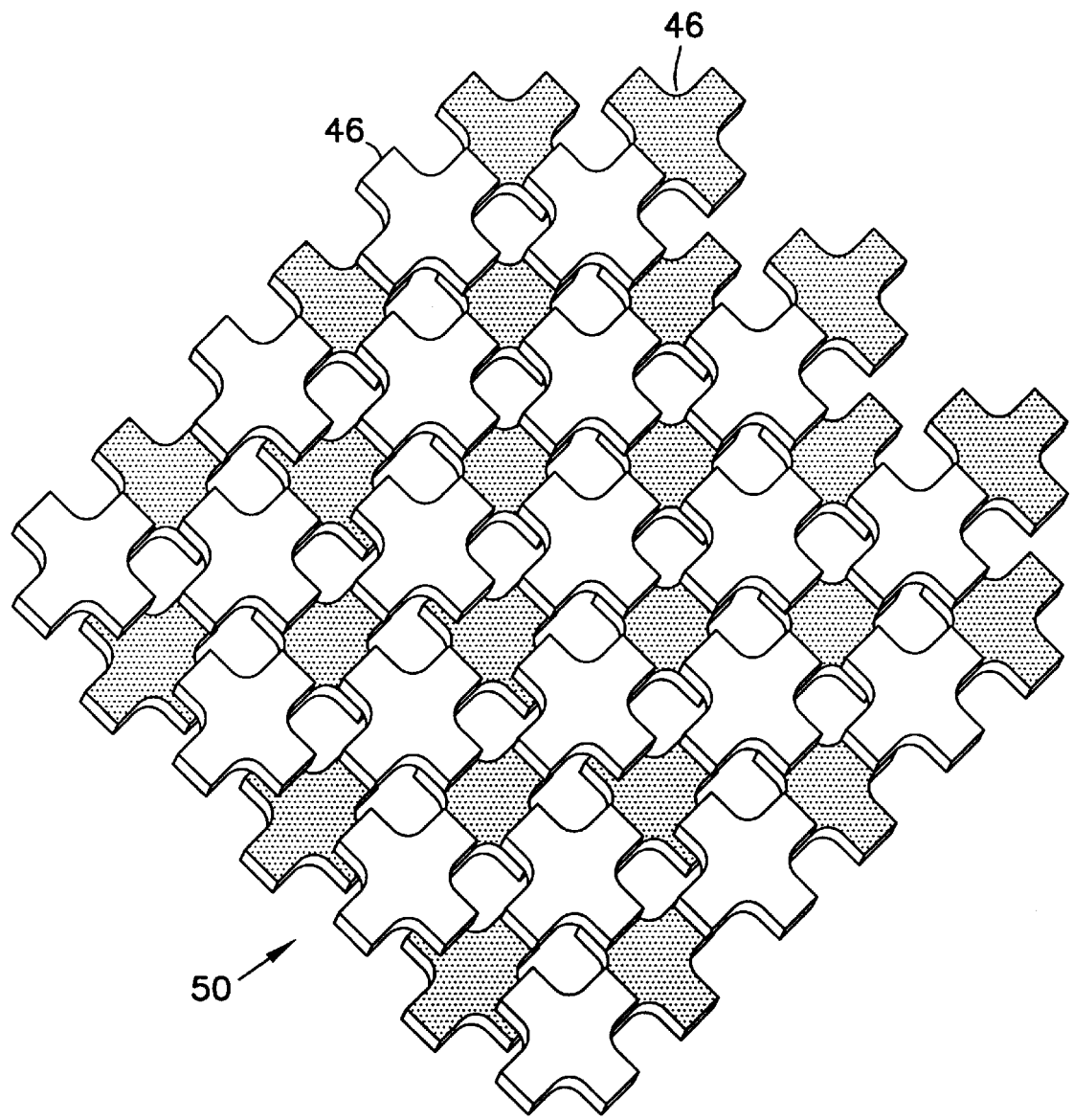
FIG. 33B is a perspective view of two sheets of planar platelets arranged in a stack in a stretched configuration.

FIGS. 32A and 32B illustrate the fabric 11 comprised of two sheets 47 arranged in a stack 50 in a compressed configuration. As shown in FIGS. 32A and 32B, the lighter gray planar platelets 46 make up the upper sheet 47. The black planar platelets 46 make up the lower sheet 47. The fabric 11 may be comprised of a plurality of sheets 47 arranged in a stack 50. As shown in FIGS. 32A and 32B, each sheet 47 in the stack 50 is shifted parallel to the adjacent sheet 47. The adjacent sheets 47 are shifted a distance so that the tab 15 of each planar platelet 46 in one sheet 47 is in line with and overlapping the tab 15 of each planar platelet 46 in the adjacent sheet 47. FIGS. 33A and 33B illustrate a two sheet stack of the fabric 11 of the alternative embodiment using planar platelets 46 in a fully stretched configuration. FIGS. 32A and 32B illustrated the fabric 11 in a compressed state.

Figure 34A:
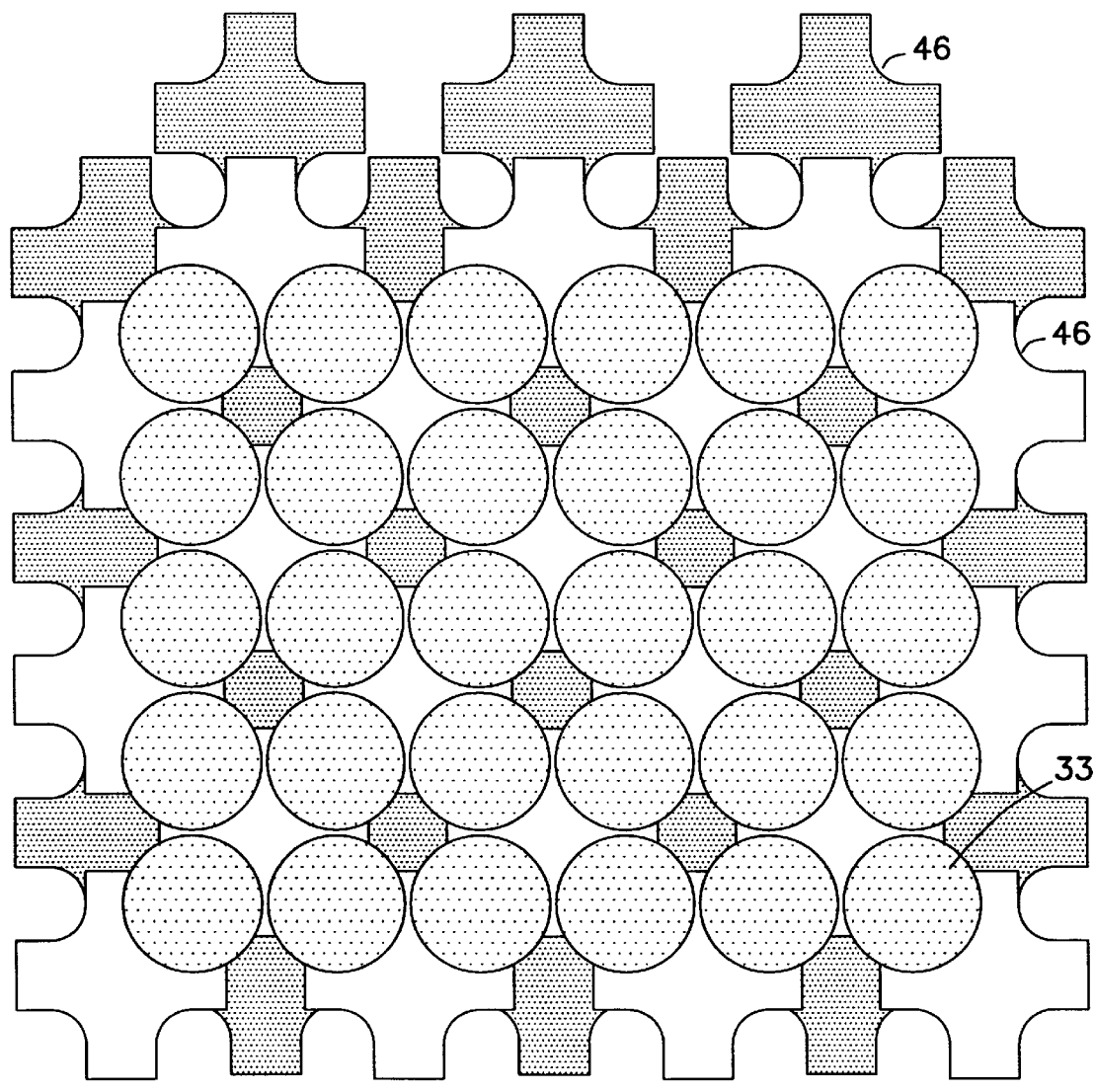
FIG. 34A is a plan view of two sheets of planar platelets arranged in a stack with rivets in a comprised configuration.
Figure 34B:
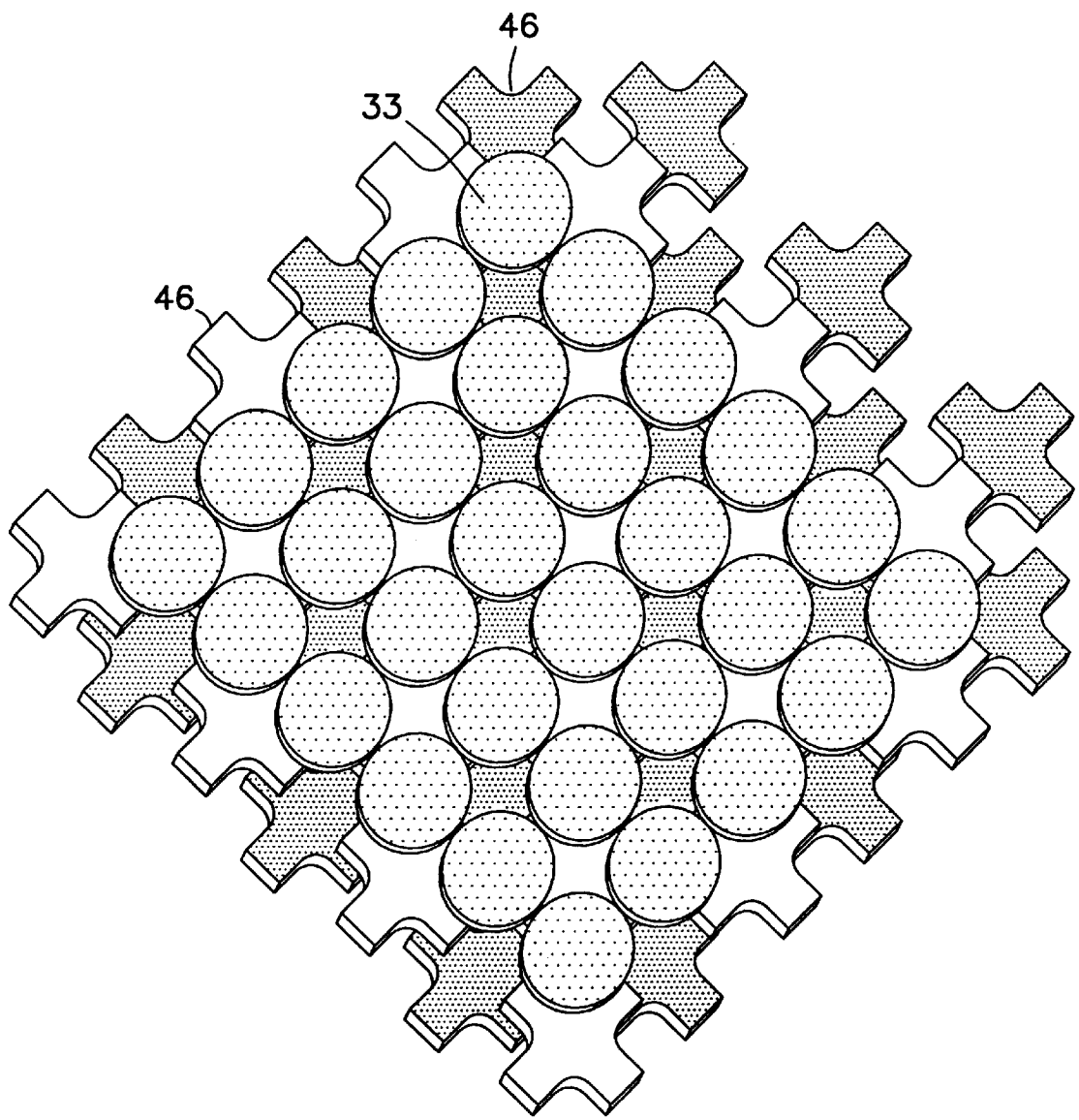
FIG. 34B is a perspective view of two sheets of planar platelets arranged in a stack with rivets in a compressed configuration.
Figure 35A:
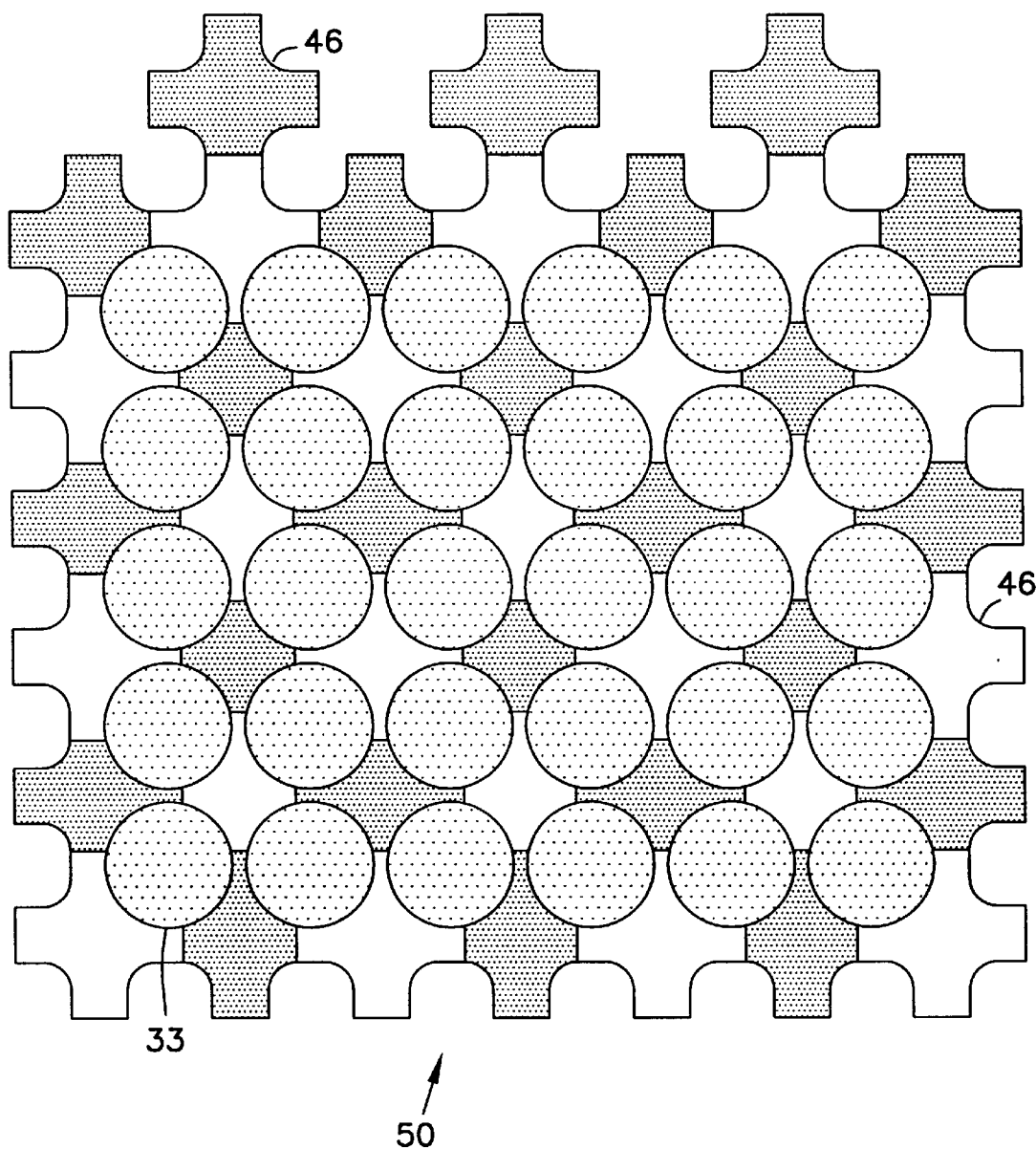
FIG. 35A is a plan view of two sheets of planar platelets arranged in a stack with rivets in a stretched configuration.
Figure 35B:
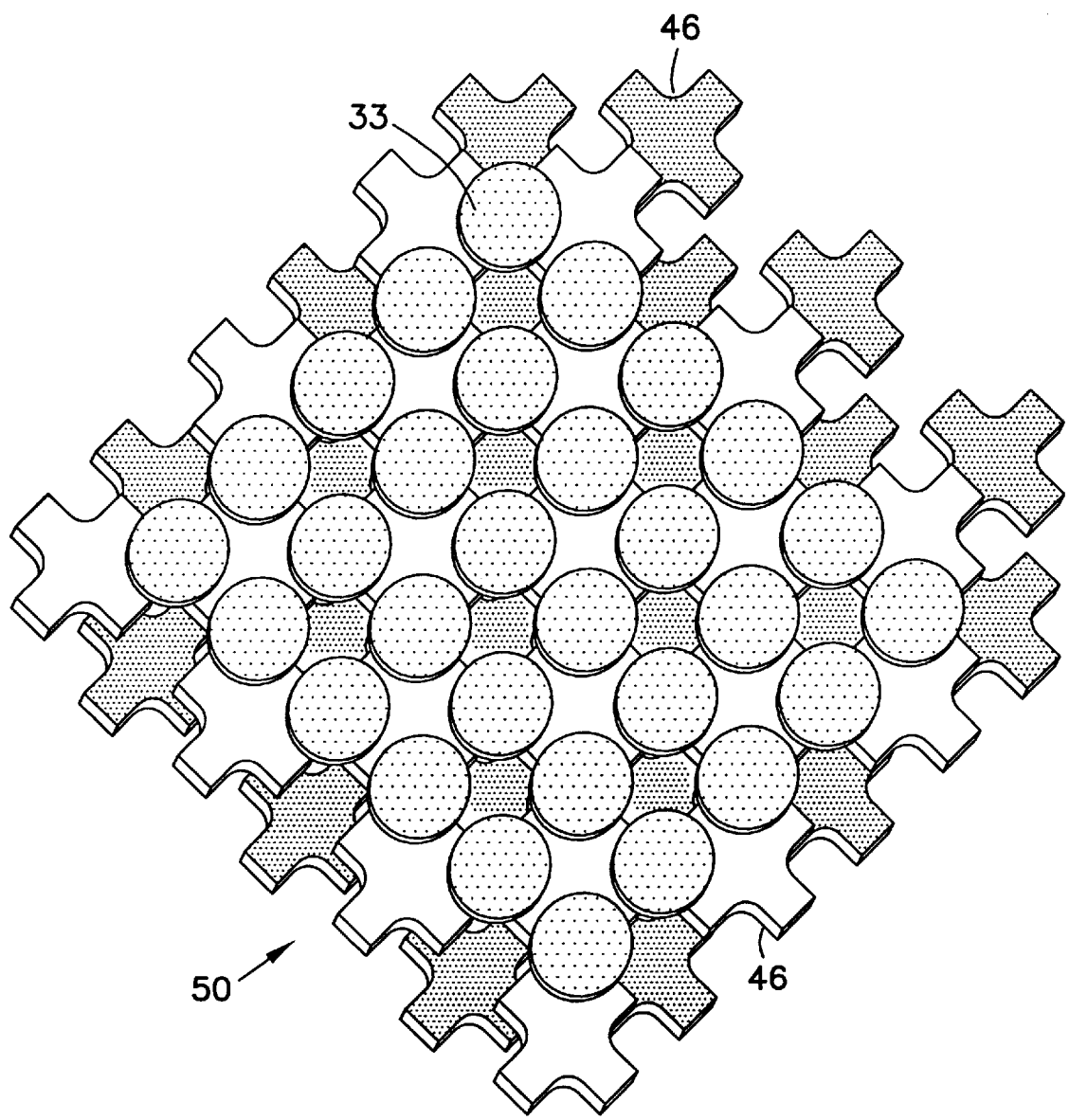
FIG. 35B is a perspective view of two sheets of planar platelets arranged in a stack with rivets in a stretched configuration.

FIG. 34A and 34B depict the alternative embodiment fabric 11 in the compressed configuration with rivets 13 inserted perpendicular to the plane of the fabric 11 through each of the apertures 26 formed by opposing edges of tabs 15 of adjacent planar platelets 46 and opposing base edges 17 of adjacent planar platelets 46. FIGS. 35A and 35B depict the fabric 11 with rivets 13 in the stretched configuration. In FIG. 34A, 34B, 35A, and 35B, the lightest gray planar platelets 46 make up the upper sheet 47 of the fabric 11. The darker gray planar platelets 46 make up the lower sheet 47. The rivets 13 are illustrated in black.

The planar platelets 46 used in the fabric 11 for differing applications will have a thickness designed to be sufficient to resist the piercing or cutting force for which the fabric 11 is designed. All of the planar platelets 46 of this preferred embodiment are identical. The rivets 13 are all identical. Both the planar platelets 46 and the rivets 13 can be formed of material such as a metal, metal alloy, plastic, composite material or ceramic, depending upon the intended application. It may be that the application will be best implemented having planar platelets 46 made of one type of material while the rivets 13 are made of another.

Figure 36A:
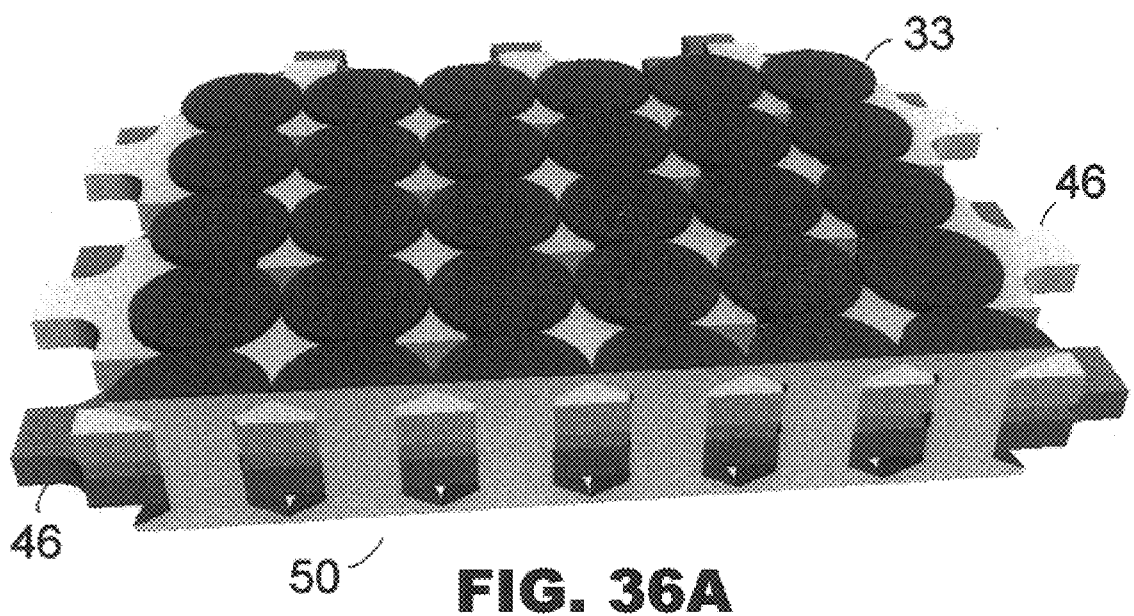
FIG. 36A is a cross-sectional perspective view of two sheets of planar platelets arranged in a stack with rivets in a compressed configuration.
Figure 36B:
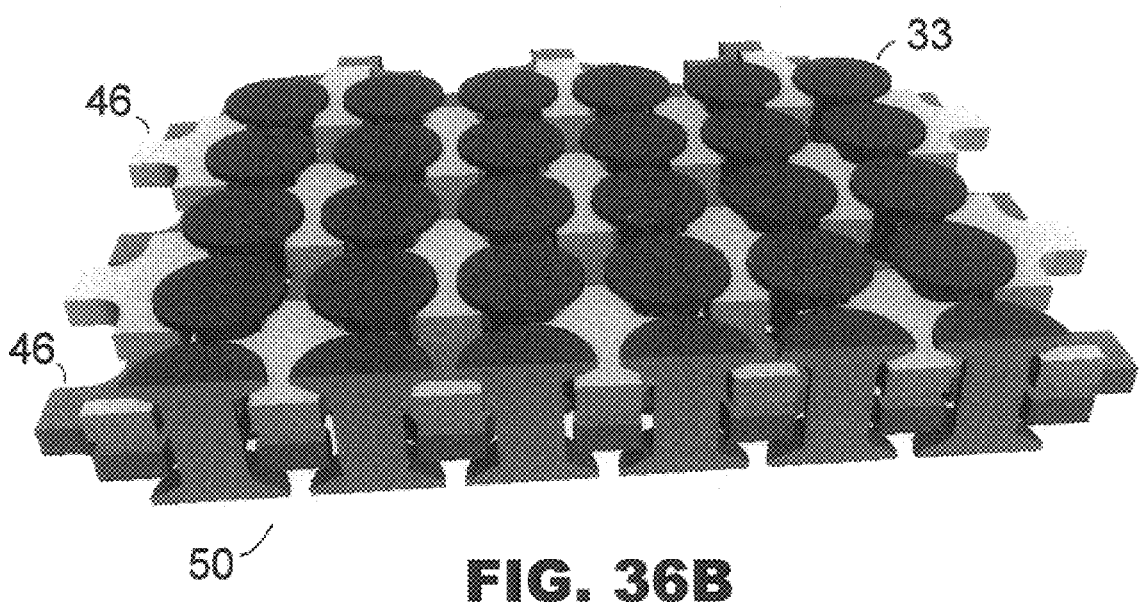
FIG. 36B is a cross-sectional perspective view of two sheets of planar platelets arranged in a stack with rivets in a stretched configuration.

FIG. 36A is a cross sectional perspective of the alternative embodiment fabric 11 using planar platelets 46. The lightest gray planar platelets 46 is the upper sheet 47, the darker gray planar platelets 46 is the lower sheet 47, and the rivets 13 are shown in black. FIG. 36B is a cross sectional perspective in the stretched configuration. FIG. 36A shows the fabric in the compressed configuration. As can be seen from FIGS. 36A and 36B, the rivets 13 hold the multi-sheet 46 fabric together. The planar platelets 46 are able to move up to the rivet heads and also at an angle relative to the plane of the fabric 11, allowing the fabric 11 to be flexible. The planar platelets 46 may also move a distance away from the rivet pin 23 to allow the fabric 11 to be stretched and compressed. As with the embodiment of the fabric 11 using platelets 12 with hooks 16, the amount of stretch and compression allowable by the fabric 11 is determined by the interrelationship of the apertures 26 of the planar platelets 46 and the rivets 13. In summary the planar platelets 46, in similar fashion to the platelets 12, are adapted to move in a range of directions and distances represented by the vertical and horizontal components of a vector.

Without the hooks 16 on the planar platelets 46, a fabric 11 can easily be torn apart. To avoid this, an interconnecting material is used to perform the function of the hooks 16. An interconnecting material is any type of material, which when interconnected between the solid objects of the fabric, maintains a predetermined spatial relationship of the solid objects within the fabric within a prescribed range of motion of the solid objects relative to one another. To do so, the connecting material should be flexible. An elastomeric material is an example of a flexible material suitable for performing this function. However, a non stretchable material is suitable for certain applications. Such a material may be constructed of fiber manufactured from man-made materials, naturally existing materials, or blends thereof. The interconnecting material may be affixed to, embedded in, or an integral part of the solid objects of the fabric 11.

Figure 37A:
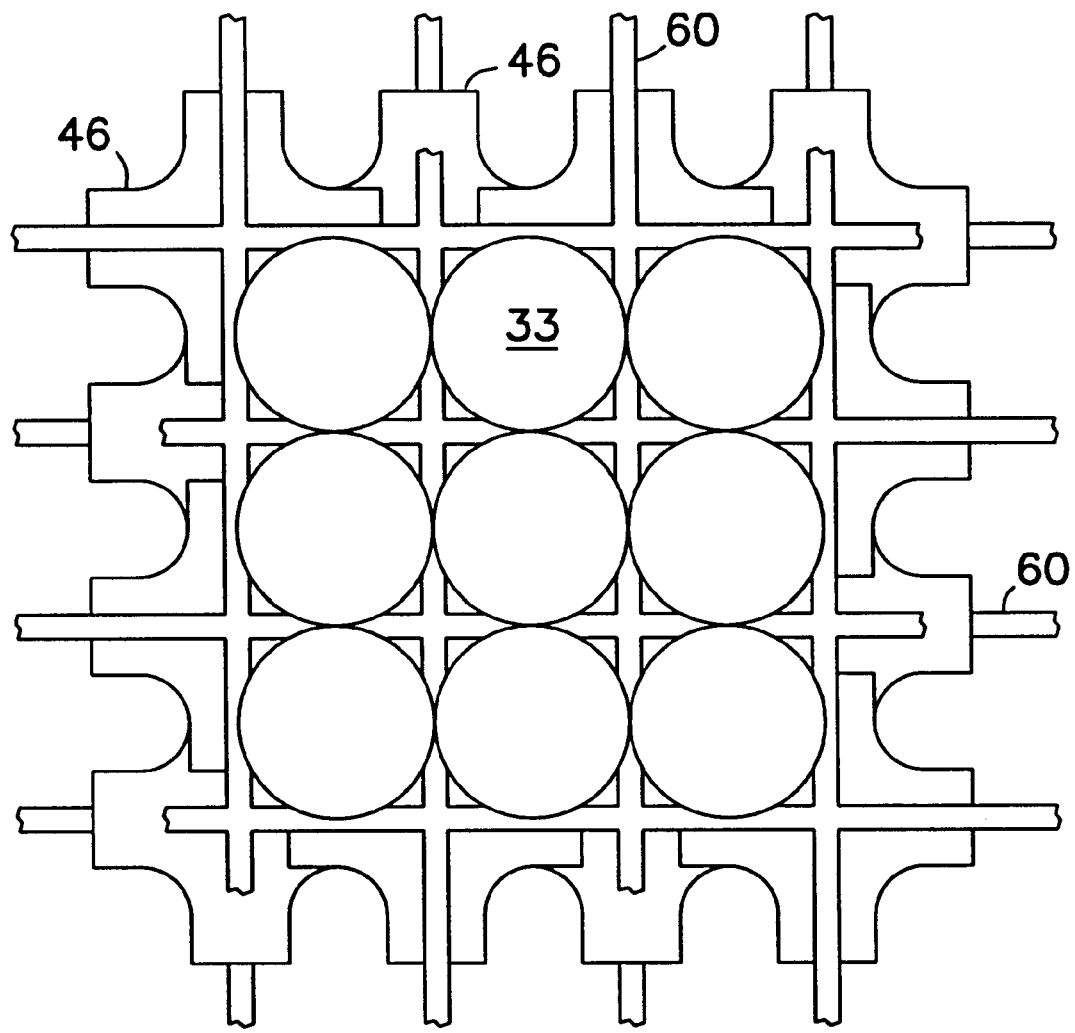
FIG. 37A is a fabric constructed with planar platelets having a net of elastomeric material affixed to the planar platelets in a compressed configuration.
Figure 37B:
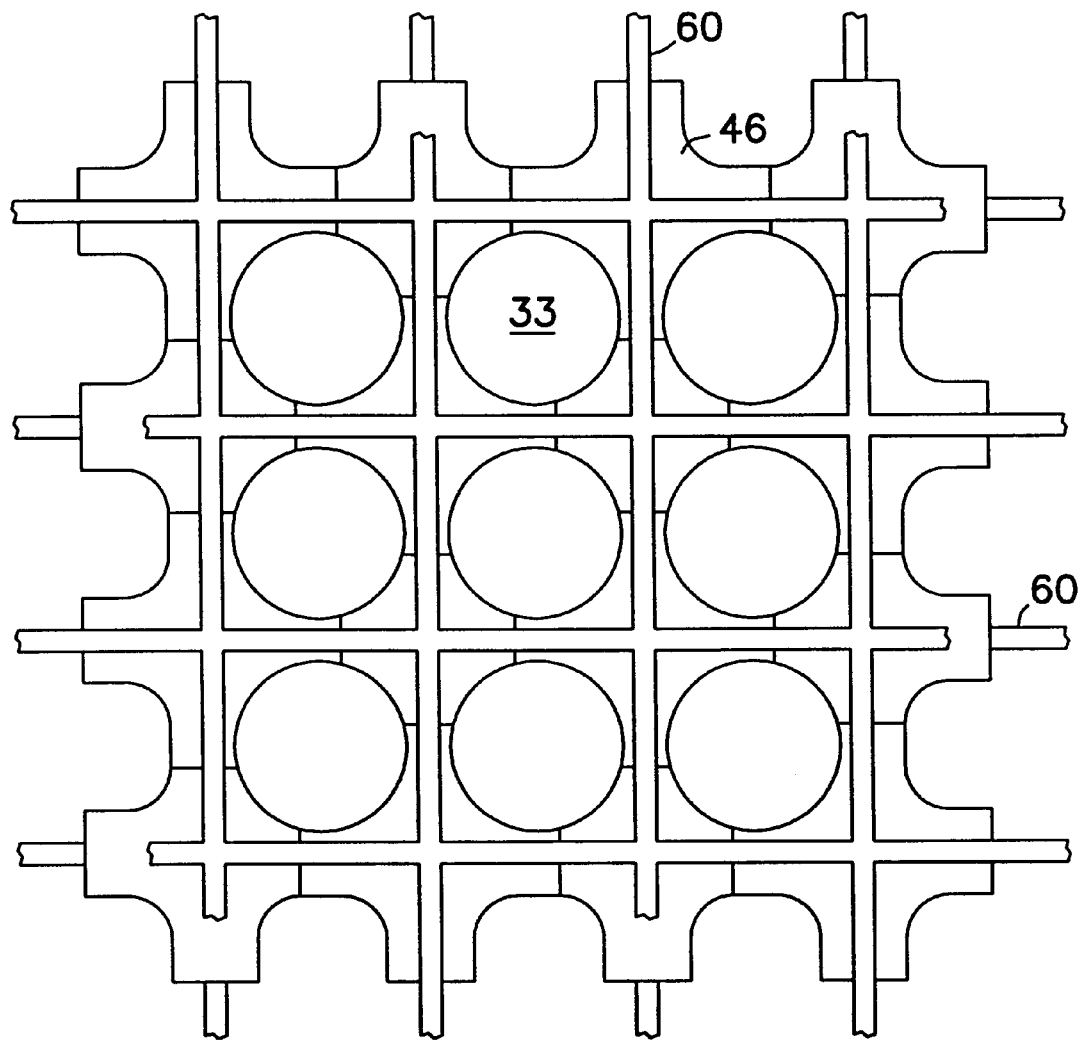
FIG. 37B is a fabric constructed with planar platelets having a net of elastomeric material affixed to the planar platelets in a stretched configuration.
Figure 38A:
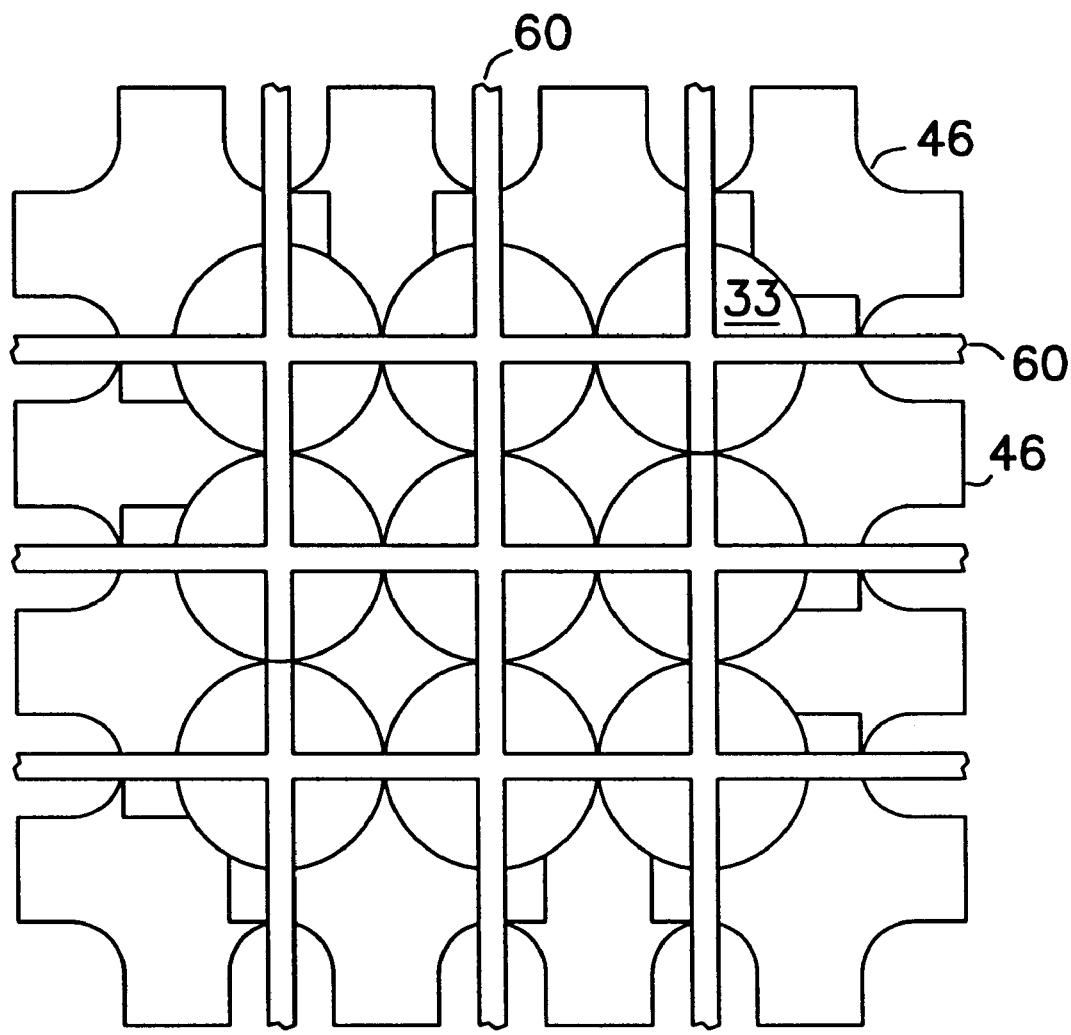
FIG. 38A is a fabric constructed with planar platelets having a net of elastomeric material affixed to the rivets in a compressed configuration.
Figure 38B:
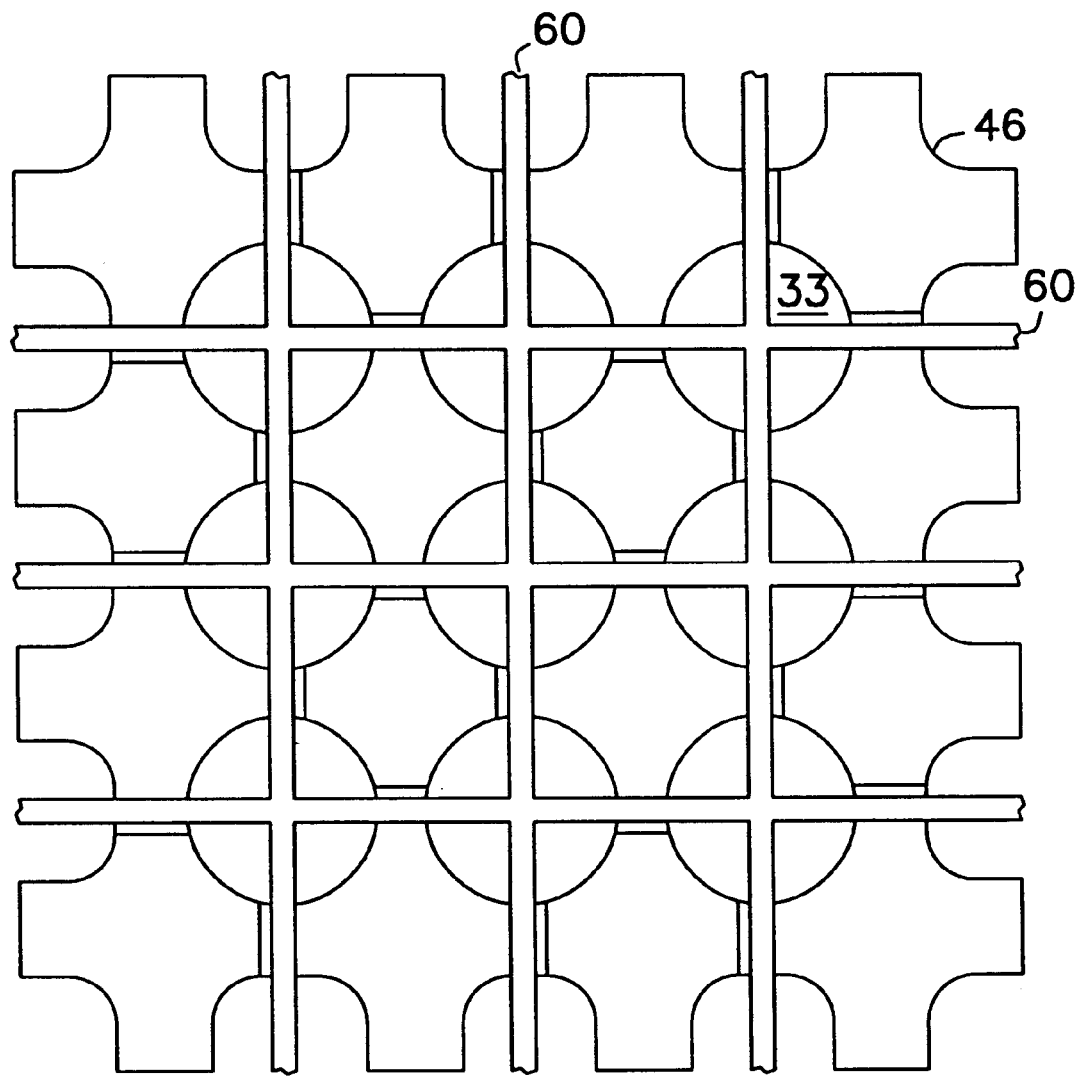
FIG. 38B is a fabric constructed with planar platelets having a net of elastomeric material affixed to the rivets in a stretched configuration.
Figure 39:
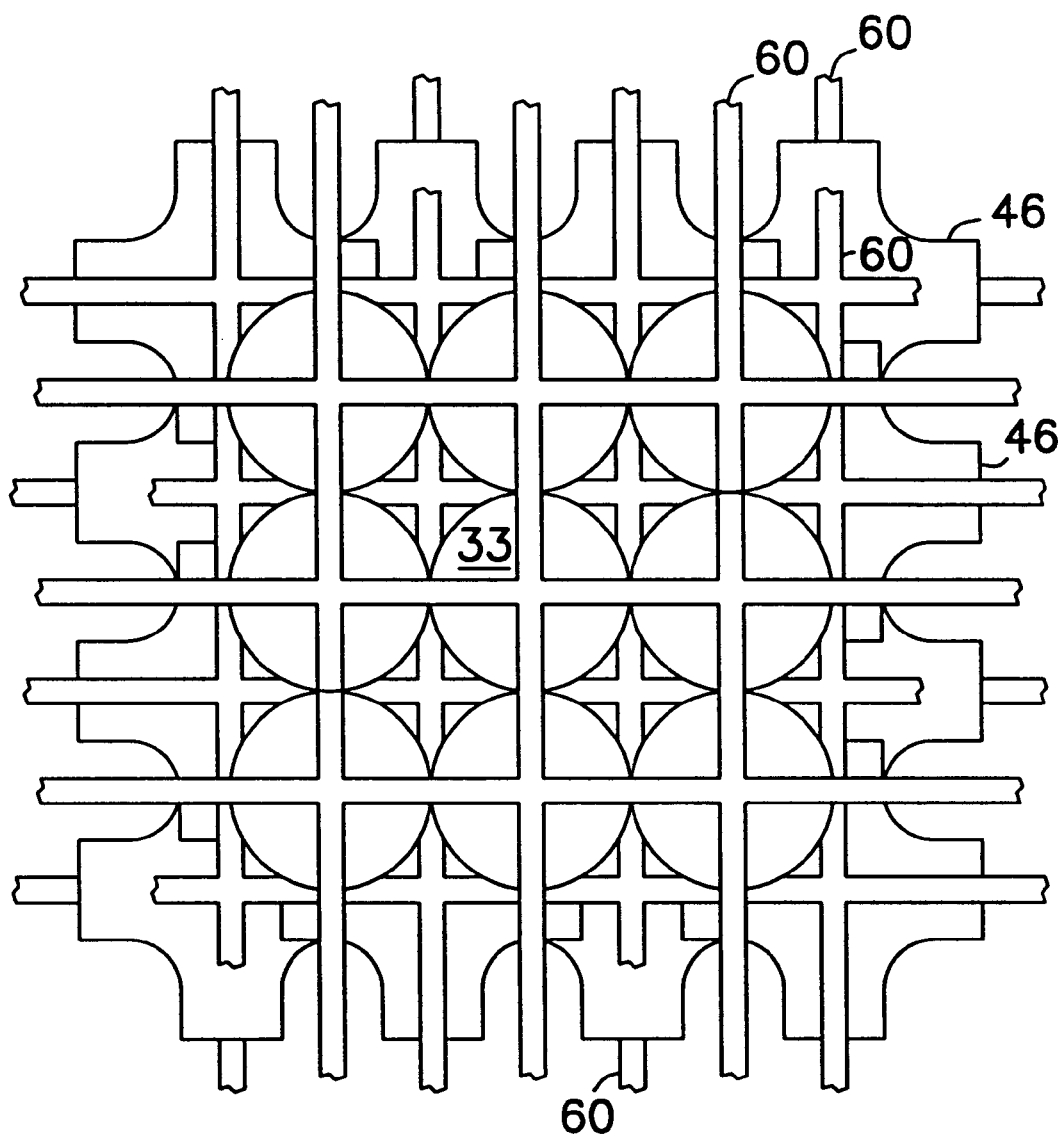
FIG. 39 is a fabric constructed with planar platelets having nets of elastomeric material affixed to both of the rivets' heads and the surfaces of both planar platelets facing the rivet heads.
Figure 40:
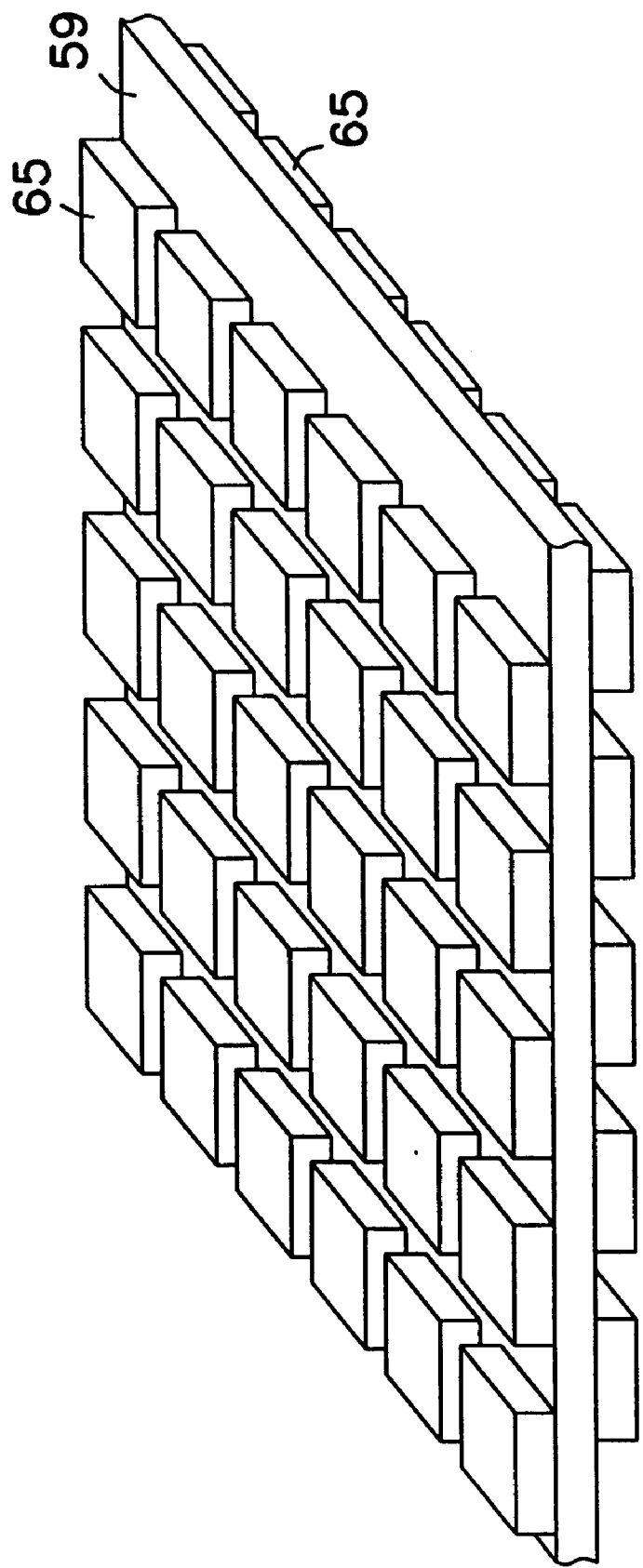
FIG. 40 illustrates a perspective view of sheets of plates with an elastomeric membrane sandwiched between the sheets.

An interconnecting material of elastomer in the form of a net 60 as shown in FIGS. 37A and 37B interconnects the surface of the planar platelets 46. In FIG. 37A, the alternative embodiment is shown in a fully compressed configuration. With the elastomeric net 60 interconnecting the nonadjacent surfaces of both sheets 47 of the planar platelets 46, the planar platelets 46 are held together along the X and Y axis of the fabric. However, since the net 60 is made of an elastomeric material, the fabric can be stretched as shown in FIG. 37B. The elastomeric material can also interconnect the tops of the heads 33 of the rivets 13 as shown in FIGS. 38A and 38B. Interconnecting the heads 33 of the rivets 13 with the elastomeric material accomplishes the same purpose as interconnecting the planar platelets 46 with the elastomeric material. It allows the fabric 11 to be stretched, but not torn apart. FIG. 38A shows the fabric 11 in the compressed state and FIG. 38B shows the fabric 11 in the stretched state. FIG. 39 shows yet another configuration with the elastomeric material covering the heads 33 of the rivets and the planar platelets 46. FIG. 39 illustrates the elastomeric net 60 interconnecting the non-adjacent surfaces of the planar platelets 46 of each sheet 47 and to only one rivet 13 head. Depending upon the application, it may be advisable to interconnect both heads 33 of each rivet 13 with the elastomeric net 60. It may also be desirable to interconnect the surfaces of adjacent planar platelets 46 between adjacent sheets 47 with a single elastomeric net. In this manner two sheets may be interconnected by the elastomeric material without rivets 13. FIG. 40 shows such a configuration using solid objects in the form of plates 65 with an elastomeric membrane 59 interconnecting the plates 65. Such a configuration may be suitable for resisting cutting forces, but not needle punctures or bullets.

Figure 41:
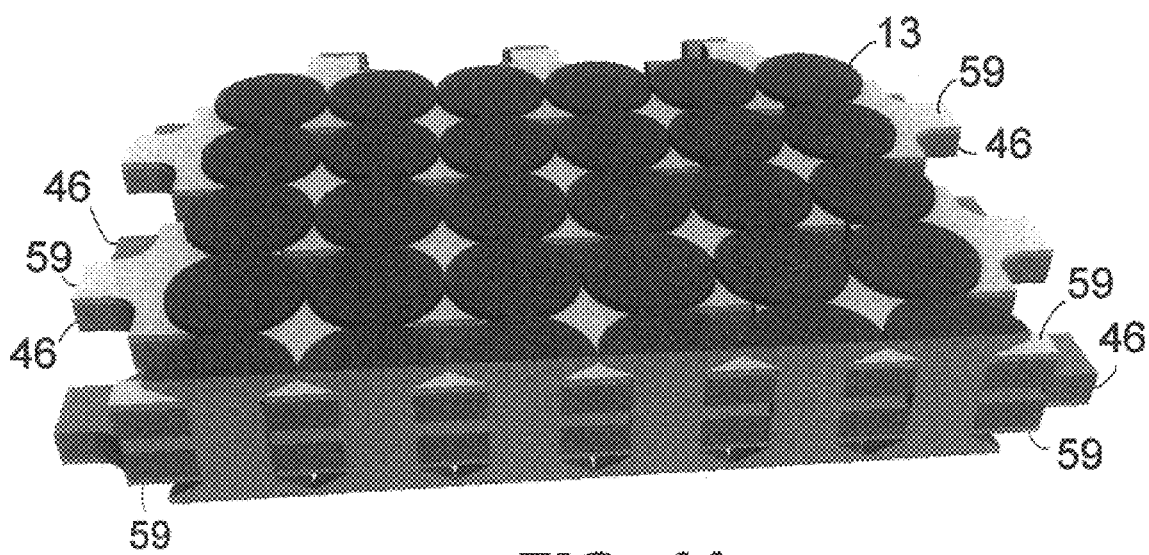
FIG. 41 illustrates a cross-sectional perspective view of two sheets of planar platelets arranged in a stack with rivets in a compressed configuration having a membrane of elastomeric material affixed to the planar platelets.

FIG. 41 is another configuration of the fabric 11 constructed with planar platelets 46 with an elastomeric membrane 59 affixed to the surfaces of the planar platelets 46. The outer surfaces being those surfaces of the planar platelets 46 in a sheet 47 that are not adjacent to the surfaces of the planar platelets 46 in an adjacent sheet 47 in a stack 50.

Figure 42:
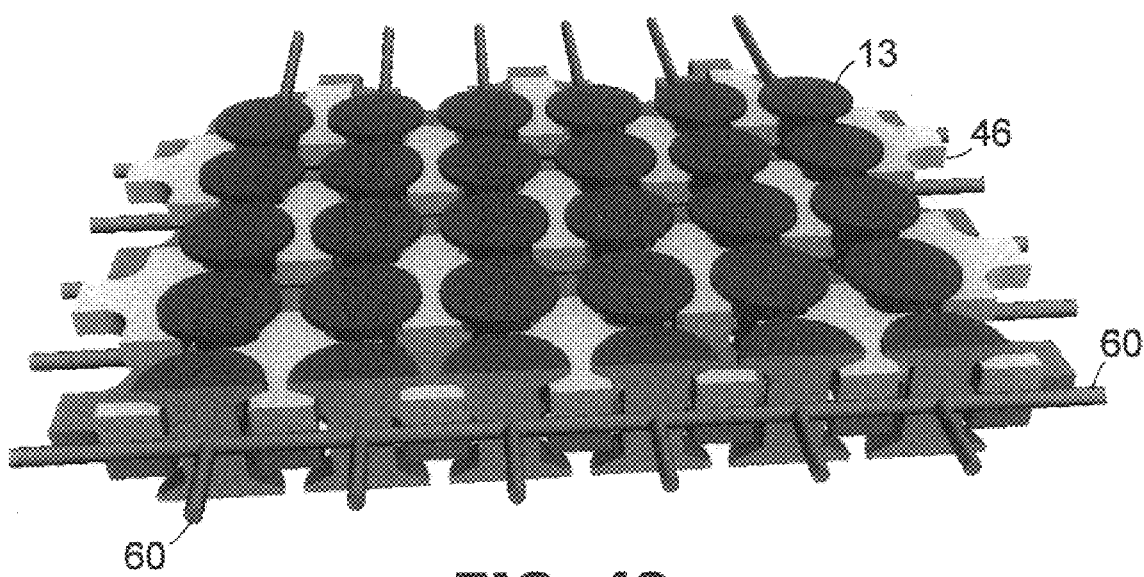
FIG. 42 illustrates a perspective cut-away view of an alternative embodiment of the fabric using interconnecting material to connect the pins of each rivet.

FIG. 46 illustrates a stack 50 of two sheets 47 of planar platelets 46 held together by rivets 13. The upper sheet 47 of planar platelets 46 is shown in lighter gray and the lower sheet 47 of planar platelets 46 is shown in dark gray. The top of the rivet 13 heads 33 are shown in black. The interconnecting material is in the form of a net 60. In this case the net 60 is an integral part of the rivet 13. One method of accomplishing this is to mold together the array of rivets 13 with the interconnection net 60 molded to the pins 23 of each rivet 13. Such a technique obviates affixing, by some bonding technique, the net 60 between each rivet 13. As shown in FIG. 42, the net 60 is affixed to the rivets 13 by threading a continuous fiber of the net 60 through a transverse hole in pin 23 of each rivet 13. A second fiber is discontinuous. It is inserted in a second hole in each rivet 13 at right angles to the first hole and at the same point on the axis of the rivit. Each portion of the net 60 passing into or through the pin 23 of a rivet 13 is bonded in its respective holes such as by an adhesive product. This latter method of forming the net 60 may seem to require a more costly fabrication method than the former. But with current automated production methods, this may be the preferred and more economical method of construction of fabric 11 as illustrated in FIG. 42.

Net 60 as depicted in FIG. 42 may be constructed of an interconnecting material that is stretchable to a limited degree and resilient. Such an interconnection material allows the fabric 11 of FIG. 42 to achieve its preferred properties. The fabric 11 is manufactured to be in its compressed state by having the length of the interconnecting material equal to the required distance between the pins 23 of the rivets 13 in the compressed state. The fabric 11 can then be stretched to a predetermined distance equivalent to the maximum stretch of the fabric 11 allowable without causing the configuration of the planar platelets 46 and rivets 13 to be unalterably changed. The interconnecting material forming the net 60 is preferably chosen so that it is stretchable when a normally expected stretching force is exerted on the fabric 11. If a stretching force in excess of the normally expected force is exerted, the interconnecting net 60 material will break or be deformed. Such a break or deformation will not allow the fabric 11 to return to its original compressed state when the stretching force is removed.

Figure 43:
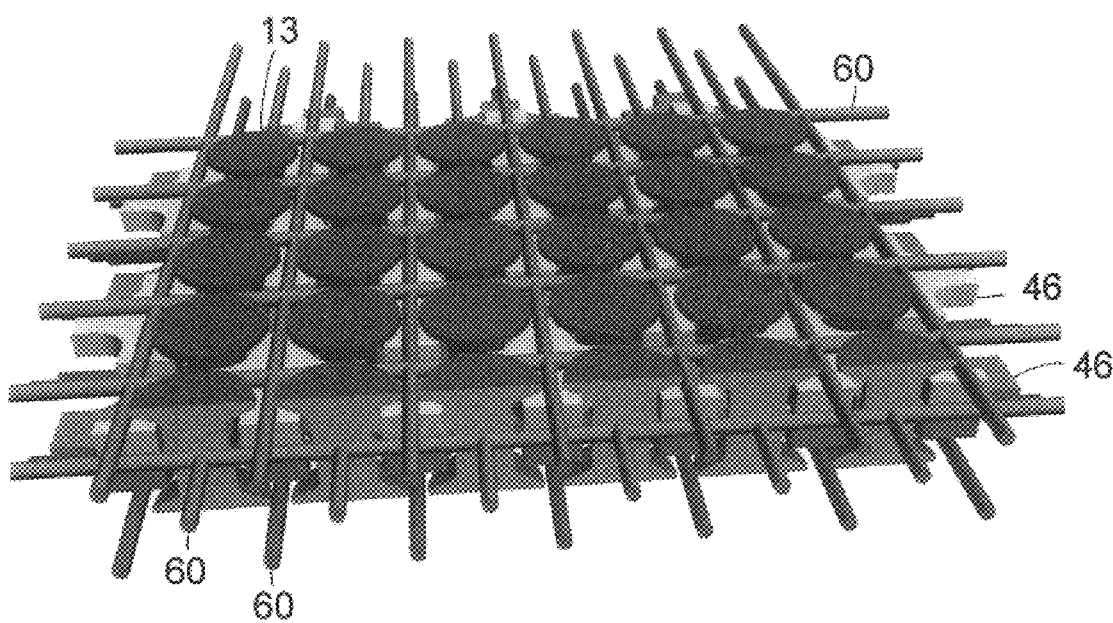
FIG. 43 illustrates a perspective cut-away view of an alternative embodiment of the fabric using interconnecting material to connect the pins of each rivet and to connect the platelets in each sheet.

FIG. 43 illustrates the interconnecting material net 60 integral to the rivets 13, but also affixed to the tops of the planar platelets 46 of both sheets 47 of the fabric 11.

As with other embodiments set forth in this specification, there are variations other than those shown in FIGS. 42 and 43 that are appropriate to meet the design needs of the application. Such variants are mere design choices and come within the spirit and scope of this invention.

In all of the configurations previously discussed an elastomeric membrane 59 may be substituted for the net 60. An elastomeric membrane 59 interconnecting a surface of platelets 12 or planer platelets 46 would completely cover the platelets leaving perforations over the apertures formed by the planar platelets. With the elastomeric membrane 59 interconnecting the heads 33 of the rivets 13, the membrane 59 can be continuous so that it completely covers the entire surface of the fabric 11. A membrane may interconnect both heads 33 of the rivets 13 and the planar platelets 46.

Yet another variation of the fabric 11 of the alternative embodiment is to have an elastomeric material sandwiched between two sheets 47. Elastomeric material in this case will interconnect both the adjacent surfaces of the sheets 47 of planar platelets 46. In this configuration, rivets 13 can be eliminated. The elastomeric material will allow the sheets 47 of planar platelets 46 to maintain a relatively fixed configuration relative to one another and yet allow them to be stretched and to be bendable relative to one another.

The elastomeric material serves the function of slideably interconnecting the planar platelets 46. It is this slideable interconnection that allows the fabric to be flexible and bendable.

The elastomeric material imparts stretchability to the alternative embodiment planar platelet 46 fabric 11. It also limits the range of motion of the upper sheet 47 relative to the lower sheet 47 in the configuration where rivets are not used. An elastomeric material may be chosen with the inherent property that it will not stretch beyond a predetermined distance. A limit on the stretchability is an important factor in avoidance of the fabric becoming disjoined if stretched beyond a predetermined distance. For example, in a configuration using rivets 13, if the planar platelets 46 are stretched to the point where the tabs 15 do not overlap, the fabric 11 may not be able to return to its compressed state due to the distal ends of adjacent tabs butting up against one another or overriding one another in a position opposite to the original configuration. Also, the distal end of the planar platelet tabs may be stretched beyond the heads of the rivets allowing the planar platelets 46 to pop up above the rivet 13 heads 33. Therefore, it is preferred to use an elastomeric material with an inherent maximum stretch.

Another method of limiting the stretch is to have non-stretchable fiber 61 material embedded in the elastomer or affixed to a surface of elastomer. The non-stretchable fiber 61 will have a predetermined length of slack when the fabric is compressed so that the maximum stretch of the fabric is a distance equal to the predetermined length of slack. Therefore, when the intended maximum stretch of the fabric 11 is reached, all the slack in the non-stretchable fiber will be taken up and the fabric 11 will not be capable of stretching beyond that point. As with the elastomeric material, the means for limiting the maximum stretch may be affixed to, embedded into, or an integral part of the planar platelets or the rivet heads.

What has been described and illustrated in this specification are various embodiments of the invention. It must be understood that these are not the only possible embodiments encompassed by this invention. This invention is capable of modification and therefore the invention is not limited to the precise details set forth in this specification. For example, instead of platelets 12 or planar platelets 46, the fabric 11 can be comprised of a sheet of solid objects of any shape.

Various arrangements of the platelets 12 and planar platelets 46 in a plane have been described. However, those arrangements of the platelets 12, planar platelets 46 other shapes of solid objects are not intended to be the only arrangements for implementing and achieving the objects of the present invention. There are many combinations of shapes of solid objects and arrangements thereof that will effectively accomplish the objects of the present invention. The limits of combinations of shapes of solid objects and the arrangements thereof is best described by the mathematics of "tessellation". Tessellation is the art of filling a plane with objects, such as the solid objects of this invention, that border each other without gaps. Mathematicians would refer to the solid objects of this invention as "tiles". Tessellations are used for floor and wall coverings and as patterns for furniture, rugs, tapestries, quilts, clothing and other objects. A tile that tessellates can have an infinite variety of shapes. Tessellation with regular convex polygonal tiles is the most common form of tessellation. However, tessellation with other shapes can yield more complex patterns that may serve artistic or utilitarian goals not achievable by regular convex polygonal tiles. The general theory of tessellation is described in a series of three articles, written by Martin Gardner, in the Mathematical Games section of the Scientific American magazine. The first article is entitled, "On tessellating the plane with convex polygon tiles"; July 1975. The second article is entitled, "More about tiling the plane: the possibilities of polyominoes, polyiamonds and polyhexes"; August 1975. The third article is entitled, "Extraordinary nonperiodic tiling that enriches the theory of tiles"; January 1977. Each of these articles is incorporated herein by reference.

The solid objects including the planar platelets 46 or platelets 12 are to be slideably interconnected to allow each sheet of the fabric to stretch. The stretchability of each sheet 47 of the fabric 11 allows the sheet 47 to be bendable, stretchable, and flexible. Means have been presented to provide for the slideable interconnection. It is to be understood that other means of slideable interconnection are within the ambit of the present invention. Likewise, the present invention has described means of slideably interconnecting sheets 47 to form a stack 50. One such means uses a rivet 13 and another means uses an elastomeric material interconnecting both of the sheets 47. In both cases, the means for interconnecting the sheets 47 provides for slideable interconnection to maintain the flexibility of the fabric. Slideable interconnection of the sheets 47 is more generally described as a means of allowing the sheets 47 to move relative to one another in a limited or bounded space. The rivets 13 allow the tabs 15 of the platelets 12 to move towards or away from the bottom of the rivet head a predetermined distance. The bottom of the rivet heads limit the movement, thereby holding the sheets together while allowing slideable movement. The connecting material also allows for slideable, but limited movement of adjacent sheets relative to one another. The connecting material is also usually adapted to allow limited slideable interconnection of the solid objects in the individual sheets. The hooks of platelets 12 serve the same function as connecting material. Both the hooks and the connecting material limit the movement of platelets 12 relative to one another. The hooks of the platelets act as stops. The hooks also allow rotational movement about adjacent hooks so that the platelets are able to move at an angle to the plane of the fabric 11. Each of these methods are designed to achieve a fabric that is flexible, bendable, and stretchable.

It is also useful to have a means for returning the solid objects, the platelets 12, or the planar platelets 46 from a stretched position to a compressed position. While the use of an elastomeric material accomplishes this function, any other method whereby the elements of the fabric are returned to a compressed position falls within the ambit of the present invention.

The rivet 13 of the present invention is one embodiment for holding the sheets together in a stack 50 while allowing the solid objects, platelets 12, or planar platelets 46 to move in the plane of the sheet 47 or in a direction at an angle to the plane of the sheet 47 to provide flexibility. Other means to allow flexibility and movement of the solid objects also falls within the concept of the present invention.

The present invention also contemplates a means of limiting the stretching of the solid objects, the platelets 12, or the planar platelets 46. Two embodiments of the means for limiting the stretching to a predetermined distance have been presented, but other means that perform the same function will also fall within the invention.

This invention includes such changes and alterations as fall within the purview of the following claims.

What is claimed as the invention is:

1. A fabric comprised of a sheet of a plurality of solid objects arranged in a tessellation pattern having means for interconnecting adjacent solid objects.

2. The fabric of claim 1, wherein the means for interconnecting the solid objects is adapted for slideable interconnection.

3. The fabric of claim 1 further comprised of a plurality of sheets arranged in a stack.

4. The fabric of claim 3, further comprising a means for interconnecting the sheets.

5. The fabric of claim 4, wherein the means for interconnecting the sheets is adapted for slideable interconnection.

6. The fabric of claim 5, also comprising a means for returning solid objects within a sheet from a stretched position to a compressed position.

7. The fabric of claim 6, wherein the means for slideably interconnecting the sheets is adapted to limit the movement of the sheets relative to one another a predetermined distance.

8. The fabric of claim 7, wherein the means for slideably interconnecting the solid objects is adapted to limit stretching of the solid objects relative to one another a predetermined distance.

9. The fabric of claim 8, wherein the solid objects are planar platelets.

10. The fabric of claim 9, wherein the tessellation pattern of the planar platelets is a repeating pattern of planar platelets arranged in a plane so that the distal end of each tab of the planar platelet forms a right angle with the distal end of adjacent tabs of adjacent planar platelets with a corner of the distal end of each adjacent tab forming the apex of a right angle.

11. The fabric of claim 10, wherein each sheet is shifted parallel to the adjacent sheet.

12. The fabric of claim 11, wherein all sheets in the stack are identical and each sheet is shifted parallel to the adjacent sheet a distance whereby the tab of each planar platelet in one sheet is in line with and overlapping the tab of each planar platelet in the adjacent sheet.

13. The fabric of claim 12, wherein a plurality of rivets are inserted perpendicular to the plane of the fabric through each of the apertures formed by opposing edges of tabs of adjacent planar platelets and opposing base edges of adjacent planar platelets.

14. The fabric of claim 13, wherein all of the planar platelets are substantially identical and all of the rivets are substantially identical.

15. The fabric of claim 14, wherein the means for slideably interconnecting the planar platelets is an interconnecting material.

16. The fabric of claim 15, wherein the interconnecting material is elastomeric.

17. The fabric of claim 15, wherein the interconnecting material interconnects the planar platelets.

18. The fabric of claim 15, wherein the interconnecting material interconnects the rivets on at least one side of the fabric.

19. The fabric of claim 17, wherein the interconnecting material is a membrane.

20. The fabric of claim 18, wherein the interconnecting material is a net.

21. The fabric of claim 15, wherein the means for limiting the maximum stretch allowed by the slideable interconnection means is an interconnecting material inherently stretchable to a predetermined limit.

22. The fabric of claim 15, wherein the means for limiting the maximum stretch allowed by the slideable interconnection means is a non-stretchable flexible material having a predetermined length of slack when the fabric is compressed so that the maximum stretch of the fabric is a distance equal to the predetermined length of slack.

23. The fabric of claim 21, wherein the means for limiting the maximum stretch allowed by the slideable interconnection means interconnects the planar platelets.

24. The fabric of claim 21, wherein the means for limiting the maximum stretch allowed by the slideable interconnection means interconnects the rivets.

25. The fabric of claim 15, wherein the interconnecting material interconnects the planar platelets between adjacent sheets.

26. The fabric of claim 19, wherein the membrane has perforations in axial alignment with each aperture.

27. The fabric of claim 15, wherein the interconnecting material is a net interconnecting the tabs of planar platelets between adjacent sheets.

28. The fabric of claim 25, further comprising interconnecting material, which interconnects the top surface of the planar platelets in the stack.

29. The fabric of claim 25, further comprising interconnecting material, which interconnects the bottom surface of the planar platelets in the stack.

30. The fabric of claim 13, wherein the rivets and the platelets are formed of material from the group consisting of a metal, metal alloy, plastic, composite material, ceramic, and glass.

31. The fabric of claim 13, wherein the planar platelet has a thickness sufficient to resist a predetermined piercing or cutting force.

32. A fabric comprised of:
(a) two sheets, each sheet having a plurality of solid objects arranged in a tesselation pattern having (i) means for slideably interconnecting the solid objects, (ii) means for returning the sheet from a stretched position to a compressed position, and (iii) means for limiting the movement of the solid objects relative to one another a predetermined amount; and
(b) each sheet in stacked arrangement with the other sheet having means for slideably interconnecting the sheets and means for limiting the movement of the sheets relative to one another a predetermined amount.

33. A fabric comprised of a plurality of plates arranged in a sheet with a means for slideably interconnecting the plates.

34. The fabric of claim 33, wherein the fabric is comprised of a plurality of sheets arranged in a stack.

35. The fabric of claim 34, wherein each sheet is shifted parallel to the adjacent sheet.

36. The fabric of claim 35, wherein each sheet is shifted so that the center of each plate on one layer is centered over the intersection of the corners of the plates of the adjacent layer.

37. The fabric of claim 33, wherein the means for slideably interconnecting the plates is an interconnecting material affixed to the plates.

38. The fabric of claim 37, wherein the interconnecting material forms a membrane.

39. The fabric of claim 37, wherein the interconnecting material forms a net.

40. The fabric of claim 33, further comprising a means for limiting the maximum stretch allowed by the slideable interconnection means.

41. The fabric of claim 40, wherein the means for limiting the maximum stretch allowed by the slideable interconnection means is an interconnecting material inherently stretchable to a predetermined limit.

42. The fabric of claim 40, wherein the means for limiting the maximum stretch allowed by the slideable interconnection means is a non-stretchable fiber having a predetermined length of slack when the fabric is compressed so that the maximum stretch of the fabric is a distance equal to the predetermined length of slack.

43. The fabric of claim 34, wherein the means for slideably interconnecting the plates is an elastomeric material interposed between adjacent sheets and bonded to the plates of adjacent sheets.

44. The fabric of claim 43, wherein the interconnecting material forms a membrane.

45. The fabric of claim 43, wherein the interconnecting material forms a net.

46. A fabric comprised of:
(a) two sheets, each sheet having a plurality of solid objects arranged in a tessellation pattern having (i) means for slideably interconnecting the solid objects, and (ii) means for limiting the movement of the solid objects relative to one another a predetermined amount; and
(b) each sheet in stacked arrangement with the other sheet having means for slideably interconnecting the sheets and means for limiting the movement of the sheets relative to one another a predetermined amount.

47. The fabric of claim 1, wherein the solid objects are identical solid objects arranged in a tessellation pattern, said tessellation pattern having four solid objects adjacent to each solid object.

48. The fabric of claim 47, wherein the tessellation pattern has six solid objects adjacent to each solid object.

49. The fabric of claim 1 wherein the solid objects are regular polygons.

50. The fabric of claim 18, wherein the interconnecting material is a nets.

51. The fabric of claim 18, wherein the interconnecting material is a membrane.

52. The fabric of claim 22, wherein the means for limiting the maximum stretch allowed by the slideable interconnection means interconnects the planar platelets.

53. The fabric of claim 22, wherein the means for limiting the maximum stretch allowed by the slideable interconnection means interconnects the rivets.

54. A fabric comprised of a sheet of a plurality of solid objects selected from hook-tabbed platelets, tabbed planar platelets, and planar plates, adjacent solid objects interconnected in a flexible, bendable, stretchable, and twistable array without permanent attachment of the solid objects directly to each other.

55. A fabric comprised of a sheet of a plurality of solid objects, adjacent solid objects interconnected by a material that maintains a predetermined spatial relationship of the solid objects within the fabric within a prescribed range of flexible, bendable, stretchable, and twistable motion of the solid objects relative to one another and without mechanical attachment of the solid objects directly to each other.

56. A fabric comprised of:
   (a) two sheets, each sheet having a plurality of solid objects selected from hook-tabbed platelets, tabbed planar platelets, and planar plates and having (i) means for slideably interconnecting the solid objects, (ii) means for returning the sheet from a stretched position to a compressed position, and (iii) means for limiting movement of the solid objects relative to one another a predetermined amount; and
   (b) each sheet in stacked arrangement with the other sheet having means for slideably interconnecting the sheets and means for limiting the movement of the sheets relative to one another a predetermined amount, such that the stacked arrangement is flexible, bendable, stretchable, and twistable, in the absence of permanent attachment of the solid objects directly to each other.

57. A fabric comprised of:
   (a) two sheets, each sheet having a plurality of solid objects having (i) means for slideably interconnecting the solid objects, (ii) means for returning the sheet from a stretched position to a compressed position, and (iii) means for limiting movement of the solid objects relative to one another a predetermined amount; and
   (b) each sheet in stacked arrangement with the other sheet having means for slideably interconnecting the sheets and means for limiting the movement of the sheets relative to one another a predetermined amount, in the absence of mechanical attachment of the solid objects and the sheets directly to each other, by means of a material that maintains a predetermined spatial relationship of the solid objects within the fabric within a prescribed range of flexible, bendable, stretchable, and twistable motion of the solid objects relative to one another.

58. A fabric comprised of a plurality of plates arranged in a sheet with a means for slideably interconnecting the plates, in the absence of mechanical attachment of the plates directly to each other, by means of a material that maintains a predetermined spatial relationship of the plates within the sheet within a prescribed range of flexible, bendable, stretchable, and twistable motion of the plates relative to one another.

59. A fabric comprised of a plurality of sheets arranged in a stack, each sheet comprised of a plurality of plates with a means for slideably interconnecting the plates, wherein a center of each plate of one sheet is over an intersection of plate corners of an adjacent sheet, such that the stack is flexible, bendable, stretchable, and twistable, in the absence of permanent attachment of the plates directly to each other.

60. A fabric comprised of:
   (a) two sheets, each sheet having a plurality of solid objects selected from hook-tabbed platelets, tabbed planar platelets and planar plates having (i) means for slideably interconnecting the solid objects, and (ii) means for limiting movement of the solid objects relative to one another a predetermined amount; and
   (b) each sheet in stacked arrangement with the other sheet having means for slideably interconnecting the sheets and means for limiting the movement of the sheets relative to one another a predetermined amount, such that the interconnecting and limiting means allow flexibility, bendability, stretchability, and twistability, in the absence of permanent attachment of the solid objects directly to each other.

61. A fabric comprised of:
   (a) two sheets, each sheet having a plurality of solid objects arranged in a tessellation pattern having (i) means for slideably interconnecting the solid objects, and (ii) means for limiting movement of the solid objects relative to one another a predetermined amount; and
   (b) each sheet in stacked arrangement with the other sheet having means for slideably interconnecting the sheets and means for limiting the movement of the sheets relative to one another a predetermined amount, in the absence of mechanical attachment of the solid objects to each other by means of a material that maintains a predetermined spatial relationship of the solid objects within the fabric within a prescribed range of motion of the solid objects relative to one another.

62. A glove, at least a portion of which is comprised of a puncture, pierce and cut resistant fabric according to any one of claims 1, 32, 33, 46, 54, 55, 56, 57, 58, 59, 60 and 61.

63. A protection for a substrate comprising a covering for the substrate constructed with a puncture, pierce and cut resistant fabric according to any one of claims 1, 32, 33, 46, 54, 55, 56, 57, 58, 59, 60 and 61.

64. A method of protecting a surface from punctures, pierces and cuts comprising the steps of:
   a) forming a fabric comprised of a plurality of sheets, each sheet having a plurality of solid objects arranged in a tessellation pattern with a means of interconnecting adjacent solid objects; and
   b) covering the surface to be protected with the fabric.

65. A method of protecting a surface from punctures, pierces and cuts comprising the steps of:
   (a) forming a fabric comprised of a plurality of sheets, each sheet having a plurality of solid objects selected from platelets, planar platelets and planar plates with a means of interconnecting adjacent solid objects, in a flexible, bendable, stretchable and twistable array, in the absence of permanent attachment of the solid objects directly to each other; and
   (b) covering the surface to be protected with the fabric.

66. A method of protecting a surface from punctures, pierces and cuts comprising the steps of:
   (a) forming a fabric comprised of a plurality of sheets, each sheet having a plurality of solid objects with a means of interconnecting adjacent solid objects, in the absence of mechanical attachment of the solid objects directly to each other by means of a material that maintains a predetermined spatial relationship of the solid objects within the fabric with a prescribed range of flexible, bendable, stretchable and twistable motion of the solid objects relative to one another; and
   (b) covering the surface to be protected with the fabric.

* * * * *